US011179394B2

(12) United States Patent
Helleday et al.

(10) Patent No.: US 11,179,394 B2
(45) Date of Patent: Nov. 23, 2021

(54) METHOD FOR TREATING CANCER USING A COMBINATION OF CHK1 AND ATR INHIBITORS

(71) Applicant: Vertex Pharmaceuticals Incorporated, Boston, MA (US)

(72) Inventors: Thomas Helleday, Stockholm (SE); Kumar Sanjiv, Stockholm (SE)

(73) Assignee: VERTEX PHARMACEUTICALS INCORPORATED, Boston, MA (US)

( * ) Notice: Subject to any disclaimer, the term of this patent is extended or adjusted under 35 U.S.C. 154(b) by 0 days.

(21) Appl. No.: 14/741,675

(22) Filed: Jun. 17, 2015

(65) Prior Publication Data

US 2015/0359797 A1 Dec. 17, 2015

Related U.S. Application Data

(60) Provisional application No. 62/013,136, filed on Jun. 17, 2014, provisional application No. 62/043,530, filed on Aug. 29, 2014, provisional application No. 62/073,082, filed on Oct. 31, 2014, provisional application No. 62/161,438, filed on May 14, 2015.

(51) Int. Cl.

| | |
|---|---|
| *A61P 35/00* | (2006.01) |
| *A61K 31/519* | (2006.01) |
| *A61K 31/4535* | (2006.01) |
| *A61K 45/06* | (2006.01) |
| *A61K 31/497* | (2006.01) |
| *A61K 31/5377* | (2006.01) |
| *A61K 31/4709* | (2006.01) |
| *A61K 31/551* | (2006.01) |
| *A61N 5/10* | (2006.01) |
| *A61K 31/4985* | (2006.01) |
| *A61K 31/4965* | (2006.01) |

(52) U.S. Cl.
CPC ........ *A61K 31/519* (2013.01); *A61K 31/4535* (2013.01); *A61K 31/4709* (2013.01); *A61K 31/497* (2013.01); *A61K 31/4965* (2013.01); *A61K 31/4985* (2013.01); *A61K 31/5377* (2013.01); *A61K 31/551* (2013.01); *A61K 45/06* (2013.01); *A61N 5/10* (2013.01)

(58) Field of Classification Search
CPC .... A61K 31/519; A61K 31/4535; A61P 35/00
See application file for complete search history.

(56) References Cited

U.S. PATENT DOCUMENTS

| | | | |
|---|---|---|---|
| 4,309,430 | A | 1/1982 | Bock et al. |
| 5,143,824 | A | 9/1992 | Yamakawa et al. |
| 5,902,773 | A | 5/1999 | Benoit et al. |
| 6,060,478 | A | 5/2000 | Gilligan et al. |
| 6,191,131 | B1 | 2/2001 | He et al. |
| 6,235,741 | B1 | 5/2001 | Bilodeau et al. |

(Continued)

FOREIGN PATENT DOCUMENTS

| | | |
|---|---|---|
| CN | 101537007 A | 9/2009 |
| CN | 101671336 A | 3/2010 |

(Continued)

OTHER PUBLICATIONS

Gupta et al., Postgrad. Med. J., vol. 81, pp. 236-242 (2005).*
American Brain Tumor Association (ABTA) http://www.abta.org/brain-tumor-information/types-of-tumors/glioma.html?print=t. Accessed Mar. 9, 2016. 3 pages.*
Johnson et al. (Relationships between drug activity and NCI preclinical in vitro and in vivo models and early clinical trials; British Journal of Cancer; (2001) 84 (10), 1424-1431).*
Voskoglou-Nomikos et al. (Clinical Predictive Value of the in Vitro Cell Line, Human Xenograft, and Mouse Allograft Preclinical Cancer Models; Clinical Cancer Research; vol. 9: 4227-4239; Sep. 15, 2003.).*

(Continued)

*Primary Examiner* — Jeffrey S Lundgren
*Assistant Examiner* — Chris E Simmons
(74) *Attorney, Agent, or Firm* — Dechert LLP; Andrea L. C. Reid; Danielle M. Nihan

(57) ABSTRACT

The present invention relates to methods of treating cancer in a patient by administering a compound useful as an inhibitor of ATR protein kinase in combination with a compound useful as an inhibitor of Chk1 protein kinase. The aforementioned combination displays a surprising synergistic effect in treating cancer despite the targeted protein kinases being within the same biological pathway. Moreover, the present invention also relates to methods of treating cancer by administering a compound useful as an inhibitor of ATR protein kinase; administering a compound useful as an inhibitor of Chk1 protein kinase; as well as administering a DNA damaging agent to a patient.
The compounds utilized in this invention are represented by formula I and formula II:

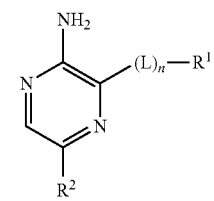

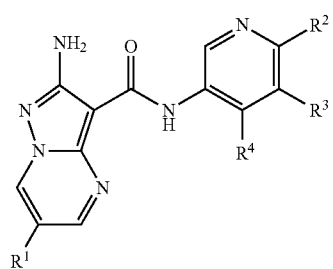

wherein the variables are as defined herein.

17 Claims, 20 Drawing Sheets

(56) References Cited

U.S. PATENT DOCUMENTS

| | | | |
|---|---|---|---|
| 6,420,367 B1 | 7/2002 | Ueda et al. | |
| 6,495,541 B1 | 12/2002 | Webber et al. | |
| 6,605,617 B2 | 8/2003 | Renhowe et al. | |
| 6,660,753 B2 | 12/2003 | Van Wagenen et al. | |
| 6,762,194 B2 | 7/2004 | Renhowe et al. | |
| 6,774,237 B2 | 8/2004 | Renhowe et al. | |
| 6,800,760 B2 | 10/2004 | Renhowe et al. | |
| 6,858,600 B2 | 2/2005 | Hamilton et al. | |
| 6,967,198 B2 | 11/2005 | Benedict et al. | |
| 6,992,087 B2 | 1/2006 | Verhoest et al. | |
| 7,041,672 B2 | 5/2006 | Verhoest et al. | |
| 7,132,533 B2 | 11/2006 | Benedict et al. | |
| 7,199,123 B2 | 4/2007 | Munchhof | |
| 7,429,578 B2 | 9/2008 | Webber et al. | |
| 7,449,464 B2 | 11/2008 | Martin et al. | |
| 7,452,993 B2 | 11/2008 | Arnold et al. | |
| 7,462,713 B2 | 12/2008 | Benedict et al. | |
| 7,528,138 B2 | 5/2009 | Knegtel et al. | |
| 7,550,470 B2 | 6/2009 | Fraley | |
| 7,550,603 B2 | 6/2009 | Zhu et al. | |
| 7,622,583 B2 | 11/2009 | Ungashe et al. | |
| 7,626,021 B2 | 12/2009 | Arnold et al. | |
| 7,700,601 B2 | 4/2010 | Chan et al. | |
| 7,704,995 B2 | 4/2010 | Buhr et al. | |
| 7,829,558 B2 | 11/2010 | Arnold et al. | |
| 7,872,031 B2 | 1/2011 | Lauffer et al. | |
| 7,902,197 B2 | 3/2011 | Elworthy et al. | |
| 7,932,254 B2 | 4/2011 | DuBois et al. | |
| 7,939,531 B2 | 5/2011 | Bamberg et al. | |
| 7,981,893 B2 | 7/2011 | Mortensen et al. | |
| 8,012,976 B2 | 9/2011 | Wang et al. | |
| 8,063,032 B2 | 11/2011 | Chytil et al. | |
| 8,071,623 B2 | 12/2011 | Jones et al. | |
| 8,093,244 B2 | 1/2012 | Diaz et al. | |
| 8,106,197 B2 | 1/2012 | Cui et al. | |
| 8,143,241 B2 | 3/2012 | Ashworth et al. | |
| 8,211,854 B2 | 7/2012 | Guzi et al. | |
| 8,247,416 B2 | 8/2012 | Menear et al. | |
| 8,252,802 B2 | 8/2012 | Foote et al. | |
| 8,410,112 B2 | 4/2013 | Charrier et al. | |
| 8,420,650 B2 | 4/2013 | Wang et al. | |
| 8,436,185 B2 | 5/2013 | Foley et al. | |
| 8,492,582 B2 | 7/2013 | Yokotani et al. | |
| 8,623,869 B2 | 1/2014 | Charrier et al. | |
| 8,822,469 B2 | 9/2014 | MacCormick et al. | |
| 8,957,078 B2 | 2/2015 | Brenchley et al. | |
| 8,962,631 B2 | 2/2015 | Charrier et al. | |
| 8,969,360 B2 | 3/2015 | Charrier et al. | |
| 8,999,632 B2 | 4/2015 | Falcon et al. | |
| 9,096,602 B2 | 8/2015 | Everitt et al. | |
| 9,309,250 B2 | 3/2016 | Storck et al. | |
| 9,340,546 B2 | 5/2016 | Ahmad et al. | |
| 9,365,557 B2 | 6/2016 | Charrier et al. | |
| 9,791,456 B2 | 10/2017 | Falcon et al. | |
| 2002/0041880 A1 | 4/2002 | DeFeo-Jones et al. | |
| 2003/0008882 A1 | 1/2003 | Hamilton et al. | |
| 2003/0028018 A1 | 2/2003 | Renhowe et al. | |
| 2003/0055085 A1 | 3/2003 | Wagenen et al. | |
| 2004/0034037 A1 | 2/2004 | Harbeson et al. | |
| 2004/0043998 A1 | 3/2004 | Kato et al. | |
| 2004/0180905 A1 | 9/2004 | Munchhof | |
| 2005/0261339 A1 | 11/2005 | Ohi et al. | |
| 2006/0156482 A1 | 7/2006 | Lim | |
| 2006/0211709 A1 | 9/2006 | Buhr et al. | |
| 2007/0010556 A1 | 1/2007 | Ashwell et al. | |
| 2007/0037794 A1 | 2/2007 | Ungashe et al. | |
| 2007/0082900 A1 | 4/2007 | Guzi et al. | |
| 2007/0112006 A1 | 5/2007 | Schiemann et al. | |
| 2007/0197389 A1 | 8/2007 | Schwogler et al. | |
| 2007/0254868 A1 | 11/2007 | Lauffer et al. | |
| 2007/0270420 A1 | 11/2007 | Harbeson et al. | |
| 2007/0287711 A1 | 12/2007 | Arnold et al. | |
| 2008/0176892 A1 | 7/2008 | Heinrich et al. | |
| 2008/0287463 A1 | 11/2008 | Herrmann et al. | |
| 2009/0005381 A1 | 1/2009 | Brown et al. | |
| 2009/0156512 A1 | 6/2009 | Umemura et al. | |
| 2009/0215724 A1 | 8/2009 | DuBois et al. | |
| 2009/0215750 A1 | 8/2009 | Bamberg et al. | |
| 2009/0215785 A1 | 8/2009 | DuBois et al. | |
| 2009/0215788 A1 | 8/2009 | Elworthy et al. | |
| 2009/0306087 A1 | 12/2009 | Ibrahim et al. | |
| 2009/0318436 A1 | 12/2009 | Albrecht et al. | |
| 2010/0036118 A1 | 2/2010 | Arnold et al. | |
| 2010/0167931 A1 | 7/2010 | Mueller et al. | |
| 2010/0168138 A1 | 7/2010 | DeGoey et al. | |
| 2010/0204214 A1 | 8/2010 | Chytil et al. | |
| 2010/0222318 A1 | 9/2010 | Charrier et al. | |
| 2010/0233091 A1 | 9/2010 | Neumann et al. | |
| 2011/0015231 A1 | 1/2011 | Al-Abed et al. | |
| 2011/0053923 A1 | 3/2011 | Foote et al. | |
| 2011/0112144 A1 | 5/2011 | Ball et al. | |
| 2011/0275797 A1 | 11/2011 | Yokotani et al. | |
| 2011/0288067 A1 | 11/2011 | Hendricks et al. | |
| 2011/0288097 A1 | 11/2011 | Hendricks et al. | |
| 2012/0027874 A1 | 2/2012 | Charrier et al. | |
| 2012/0035407 A1 | 2/2012 | Charrier et al. | |
| 2012/0035408 A1 | 2/2012 | Charrier et al. | |
| 2012/0040020 A1 | 2/2012 | Charrier et al. | |
| 2012/0046295 A1 | 2/2012 | Charrier et al. | |
| 2012/0065247 A1 | 3/2012 | Thompson et al. | |
| 2012/0115874 A1 | 5/2012 | Wang et al. | |
| 2012/0122884 A1 | 5/2012 | Charrier et al. | |
| 2012/0177748 A1 | 7/2012 | Charrier et al. | |
| 2012/0178756 A1 | 7/2012 | Charrier et al. | |
| 2012/0178915 A1 | 7/2012 | Xu | |
| 2013/0017273 A1 | 1/2013 | Everitt et al. | |
| 2013/0018035 A1 | 1/2013 | MacCormick et al. | |
| 2013/0034616 A1 | 2/2013 | Storck et al. | |
| 2013/0089624 A1 | 4/2013 | Charrier et al. | |
| 2013/0089625 A1 | 4/2013 | Charrier et al. | |
| 2013/0089626 A1* | 4/2013 | Pollard | A61K 31/4965 424/649 |
| 2013/0095193 A1 | 4/2013 | Charrier et al. | |
| 2013/0096139 A1 | 4/2013 | Charrier et al. | |
| 2013/0115310 A1 | 5/2013 | Charrier et al. | |
| 2013/0115311 A1 | 5/2013 | Charrier et al. | |
| 2013/0115312 A1 | 5/2013 | Charrier et al. | |
| 2013/0115313 A1 | 5/2013 | Charrier et al. | |
| 2013/0115314 A1 | 5/2013 | Charrier et al. | |
| 2013/0172273 A1 | 7/2013 | Aizpurua Iparraguirre et al. | |
| 2013/0184292 A1 | 7/2013 | Charrier et al. | |
| 2014/0044802 A1 | 2/2014 | Pollard et al. | |
| 2014/0100229 A1 | 4/2014 | Follmann et al. | |
| 2014/0113005 A1 | 4/2014 | Charrier et al. | |
| 2014/0163000 A1 | 6/2014 | Ahmad et al. | |
| 2014/0249157 A1 | 9/2014 | Ahmad et al. | |
| 2014/0275009 A1 | 9/2014 | Brenchley et al. | |
| 2014/0275021 A1 | 9/2014 | Charrier et al. | |
| 2014/0275130 A1 | 9/2014 | Charrier et al. | |
| 2014/0288347 A1 | 9/2014 | Charrier et al. | |
| 2014/0356456 A1 | 12/2014 | Pollard et al. | |
| 2015/0005263 A1 | 1/2015 | Hart et al. | |
| 2015/0051187 A1 | 2/2015 | Charrier et al. | |
| 2015/0158868 A1 | 6/2015 | Boyall et al. | |
| 2015/0158872 A1 | 6/2015 | Charrier et al. | |
| 2015/0216175 A1 | 8/2015 | Heil et al. | |
| 2015/0274710 A1 | 10/2015 | Charrier et al. | |
| 2015/0291601 A1 | 10/2015 | Brenchley et al. | |
| 2015/0299205 A1 | 10/2015 | Charrier et al. | |
| 2015/0353560 A1 | 12/2015 | Ahmad et al. | |
| 2015/0376187 A1 | 12/2015 | Everitt et al. | |
| 2016/0009723 A1 | 1/2016 | Charrier et al. | |
| 2016/0030424 A1 | 2/2016 | Pollard et al. | |
| 2016/0311809 A1 | 10/2016 | Charrier et al. | |
| 2016/0326180 A1 | 11/2016 | Boyall et al. | |
| 2016/0347754 A1 | 12/2016 | Ahmad et al. | |
| 2017/0349596 A1 | 12/2017 | Ahmad et al. | |
| 2018/0072735 A1 | 3/2018 | Ahmad et al. | |

FOREIGN PATENT DOCUMENTS

| | | |
|---|---|---|
| CN | 103373996 A | 10/2013 |
| EP | 0313724 A2 | 5/1989 |
| EP | 1217000 A1 | 6/2002 |

(56) References Cited

FOREIGN PATENT DOCUMENTS

| | | |
|---|---|---|
| EP | 2157090 A1 | 2/2010 |
| JP | 2001-302666 A | 10/2001 |
| WO | WO 96/35690 A1 | 11/1996 |
| WO | WO 97/43267 A1 | 11/1997 |
| WO | WO 98/003510 A1 | 1/1998 |
| WO | WO 98/33799 A1 | 8/1998 |
| WO | WO 98/42701 A1 | 10/1998 |
| WO | WO 98/54093 A1 | 12/1998 |
| WO | WO 00/04014 A1 | 1/2000 |
| WO | WO 00/53605 A1 | 9/2000 |
| WO | WO 01/040231 A1 | 6/2001 |
| WO | WO 01/44206 A1 | 6/2001 |
| WO | WO 01/92257 A1 | 12/2001 |
| WO | WO 02/09648 A2 | 2/2002 |
| WO | WO 02/040485 A1 | 5/2002 |
| WO | WO 02/066481 A1 | 8/2002 |
| WO | WO 03/000187 A2 | 1/2003 |
| WO | WO 03/004472 A1 | 1/2003 |
| WO | WO 03/004475 A1 | 1/2003 |
| WO | WO 03/037900 A2 | 5/2003 |
| WO | WO 03/045924 A1 | 6/2003 |
| WO | WO 03/076422 A1 | 9/2003 |
| WO | WO 03/080610 A1 | 10/2003 |
| WO | WO 03/087057 A1 | 10/2003 |
| WO | WO 03/092686 A1 | 11/2003 |
| WO | WO 03/093297 A2 | 11/2003 |
| WO | WO 03/101968 A1 | 12/2003 |
| WO | WO 03/101993 A1 | 12/2003 |
| WO | WO 2004/000318 A2 | 12/2003 |
| WO | WO 2004/022559 A1 | 3/2004 |
| WO | WO 2004/022560 A1 | 3/2004 |
| WO | WO 2004/022561 A1 | 3/2004 |
| WO | WO 2004/026229 A2 | 4/2004 |
| WO | WO 2004/033431 A2 | 4/2004 |
| WO | WO 2004/052315 A2 | 6/2004 |
| WO | WO 2004/055005 A1 | 7/2004 |
| WO | WO 2004/055006 A1 | 7/2004 |
| WO | WO 2004/076458 A1 | 9/2004 |
| WO | WO 2004/080982 A1 | 9/2004 |
| WO | WO 2004/084813 A2 | 10/2004 |
| WO | WO 2004/084824 A1 | 10/2004 |
| WO | WO 2004/085409 A2 | 10/2004 |
| WO | WO 2004/103279 A2 | 12/2004 |
| WO | WO 2005/028434 A2 | 3/2005 |
| WO | WO 2005/028475 A2 | 3/2005 |
| WO | WO 2005/051906 A2 | 6/2005 |
| WO | WO 2005/054246 A2 | 6/2005 |
| WO | WO 2005/077954 A2 | 8/2005 |
| WO | WO 2005/079802 A1 | 9/2005 |
| WO | WO 2005/080396 A2 | 9/2005 |
| WO | WO 2005/117909 A2 | 12/2005 |
| WO | WO 2005/123672 A2 | 12/2005 |
| WO | WO 2006/015124 A2 | 2/2006 |
| WO | WO 2006/052913 A1 | 5/2006 |
| WO | WO 2006/053342 A2 | 5/2006 |
| WO | WO 2006/058074 A1 | 6/2006 |
| WO | WO 2006/067462 A1 | 6/2006 |
| WO | WO 2006/071548 A2 | 7/2006 |
| WO | WO 2006/071752 A1 | 7/2006 |
| WO | WO 2006/075152 A1 | 7/2006 |
| WO | WO 2006/087120 A2 | 8/2006 |
| WO | WO 2006/088837 A2 | 8/2006 |
| WO | WO 2006/114180 A1 | 11/2006 |
| WO | WO 2006/120573 A2 | 11/2006 |
| WO | WO 2006/128184 A2 | 11/2006 |
| WO | WO 2007/015632 A1 | 2/2007 |
| WO | WO 2007/041712 A1 | 4/2007 |
| WO | WO 2007/044401 A2 | 4/2007 |
| WO | WO 2007/044407 A2 | 4/2007 |
| WO | WO 2007/044410 A1 | 4/2007 |
| WO | WO 2007/044420 A1 | 4/2007 |
| WO | WO 2007/044426 A2 | 4/2007 |
| WO | WO 2007/044441 A2 | 4/2007 |
| WO | WO 2007/044449 A2 | 4/2007 |
| WO | WO 2007/046548 A1 | 4/2007 |
| WO | WO 2007/048066 A2 | 4/2007 |
| WO | WO 2007/058850 A2 | 5/2007 |
| WO | WO 2007/063012 A1 | 6/2007 |
| WO | WO 2007/066805 A1 | 6/2007 |
| WO | WO 2007/076360 A1 | 7/2007 |
| WO | WO 2007/096151 A2 | 8/2007 |
| WO | WO 2007/096764 A2 | 8/2007 |
| WO | WO 2007/096765 A1 | 8/2007 |
| WO | WO 2007/102770 A1 | 9/2007 |
| WO | WO 2007/111904 A2 | 10/2007 |
| WO | WO 2007/126841 A2 | 11/2007 |
| WO | WO 2007/126964 A2 | 11/2007 |
| WO | WO 2007/139732 A1 | 12/2007 |
| WO | WO 2007/139856 A2 | 12/2007 |
| WO | WO 2007/139860 A2 | 12/2007 |
| WO | WO 2007/147874 A1 | 12/2007 |
| WO | WO 2008/004698 A2 | 1/2008 |
| WO | WO 2008/008539 A2 | 1/2008 |
| WO | WO 2008/037477 A1 | 4/2008 |
| WO | WO 2008/038010 A1 | 4/2008 |
| WO | WO 2008/040651 A1 | 4/2008 |
| WO | WO 2008/045266 A2 | 4/2008 |
| WO | WO 2008/045268 A2 | 4/2008 |
| WO | WO 2008/060907 A2 | 5/2008 |
| WO | WO 2008/063671 A2 | 5/2008 |
| WO | WO 2008/071456 A2 | 6/2008 |
| WO | WO 2008/074997 A1 | 6/2008 |
| WO | WO 2008/079291 A2 | 7/2008 |
| WO | WO 2008/079903 A1 | 7/2008 |
| WO | WO 2008/079906 A1 | 7/2008 |
| WO | WO 2008/103277 A2 | 8/2008 |
| WO | WO 2008/106692 A1 | 9/2008 |
| WO | WO 2008/122375 A2 | 10/2008 |
| WO | WO 2008/124850 A1 | 10/2008 |
| WO | WO 2008/130569 A1 | 10/2008 |
| WO | WO 2008/130570 A1 | 10/2008 |
| WO | WO 2008/141065 A1 | 11/2008 |
| WO | WO 2008/144463 A1 | 11/2008 |
| WO | WO 2008/144464 A1 | 11/2008 |
| WO | WO 2008/151735 A2 | 12/2008 |
| WO | WO 2008/157191 A2 | 12/2008 |
| WO | WO 2009/006580 A1 | 1/2009 |
| WO | WO 2009/007390 A2 | 1/2009 |
| WO | WO 2009/012482 A2 | 1/2009 |
| WO | WO 2009/014637 A2 | 1/2009 |
| WO | WO 2009/016460 A2 | 2/2009 |
| WO | WO 2009/017954 A1 | 2/2009 |
| WO | WO 2009/024825 A1 | 2/2009 |
| WO | WO 2009/037247 A1 | 3/2009 |
| WO | WO 2009/053737 A2 | 4/2009 |
| WO | WO 2009/070567 A1 | 6/2009 |
| WO | WO 2009/075790 A1 | 6/2009 |
| WO | WO 2009/088986 A1 | 7/2009 |
| WO | WO 2009/091374 A2 | 7/2009 |
| WO | WO 2009/095254 A1 | 8/2009 |
| WO | WO 2009/106885 A1 | 9/2009 |
| WO | WO 2009/117157 A1 | 9/2009 |
| WO | WO 2010/002483 A1 | 1/2010 |
| WO | WO 2010/006086 A2 | 1/2010 |
| WO | WO 2010/015803 A1 | 2/2010 |
| WO | WO 2010/017047 A1 | 2/2010 |
| WO | WO 2010/034738 A2 | 4/2010 |
| WO | WO 2010/048131 A1 | 4/2010 |
| WO | WO 2010/051549 A1 | 5/2010 |
| WO | WO 2010/054398 A1 | 5/2010 |
| WO | WO 2010/059836 A1 | 5/2010 |
| WO | WO 2010/063634 A1 | 6/2010 |
| WO | WO 2010/068483 A2 | 6/2010 |
| WO | WO 2010/071837 A1 | 6/2010 |
| WO | WO 2010/086040 A1 | 8/2010 |
| WO | WO 2010/091409 A1 | 8/2010 |
| WO | 2011006074 | 1/2011 |
| WO | WO 2011/003065 A2 | 1/2011 |
| WO | WO 2011/008830 A1 | 1/2011 |
| WO | WO 2011/022439 A1 | 2/2011 |
| WO | WO 2011/025706 A2 | 3/2011 |
| WO | WO 2011/068667 A1 | 6/2011 |
| WO | WO 2011/113606 A1 | 9/2011 |
| WO | WO 2011/117145 A2 | 9/2011 |

(56) References Cited

FOREIGN PATENT DOCUMENTS

| | | |
|---|---|---|
| WO | WO 2011/121096 A1 | 10/2011 |
| WO | WO 2011/124998 A1 | 10/2011 |
| WO | WO 2011/130689 A1 | 10/2011 |
| WO | WO 2011/143399 A1 | 11/2011 |
| WO | WO 2011/143419 A1 | 11/2011 |
| WO | WO 2011/143422 A1 | 11/2011 |
| WO | WO 2011/143423 A2 | 11/2011 |
| WO | WO 2011/143425 A2 | 11/2011 |
| WO | WO 2011/143426 A1 | 11/2011 |
| WO | WO 2011/144584 A1 | 11/2011 |
| WO | WO 2011/144585 A1 | 11/2011 |
| WO | WO 2011/163518 A1 | 12/2011 |
| WO | WO 2012/007375 A1 | 1/2012 |
| WO | WO 2012/022045 A1 | 2/2012 |
| WO | WO 2012/027236 A1 | 3/2012 |
| WO | WO 2012/067822 A1 | 5/2012 |
| WO | WO 2012/074754 A1 | 6/2012 |
| WO | WO 2012/078855 A1 | 6/2012 |
| WO | WO 2012/100342 A1 | 8/2012 |
| WO | WO 2012/138938 A1 | 10/2012 |
| WO | WO 2012/143510 A1 | 10/2012 |
| WO | WO 2012/143796 A2 | 10/2012 |
| WO | WO 2012/158785 A1 | 11/2012 |
| WO | WO 2012/177997 A1 | 12/2012 |
| WO | WO 2012/178124 A1 | 12/2012 |
| WO | WO 2013/010136 A2 | 1/2013 |
| WO | 2013049859 A1 | 4/2013 |
| WO | WO 2013/049720 A1 | 4/2013 |
| WO | WO 2013/049726 A2 | 4/2013 |
| WO | WO 2013/052263 A2 | 4/2013 |
| WO | WO 2013/059587 A1 | 4/2013 |
| WO | WO 2013/138436 A1 | 9/2013 |
| WO | WO 2013/151930 A1 | 10/2013 |
| WO | WO 2013/151938 A1 | 10/2013 |
| WO | WO 2013/154878 A1 | 10/2013 |
| WO | WO 2013/171470 A1 | 11/2013 |
| WO | WO 2013/174930 A2 | 11/2013 |
| WO | WO 2013/174931 A1 | 11/2013 |
| WO | WO 2014/011911 A2 | 1/2014 |
| WO | WO 2014/015523 A1 | 1/2014 |
| WO | WO 2014/023691 A1 | 2/2014 |
| WO | WO 2014/025850 A1 | 2/2014 |
| WO | WO 2014/025852 A1 | 2/2014 |
| WO | WO 2014/025854 A1 | 2/2014 |
| WO | WO 2014/026984 A1 | 2/2014 |
| WO | WO 2014/029723 A1 | 2/2014 |
| WO | WO 2014/035140 A2 | 3/2014 |
| WO | WO 2014/039831 A1 | 3/2014 |
| WO | WO 2014/042433 A2 | 3/2014 |
| WO | WO 2014/044691 A1 | 3/2014 |
| WO | WO 2014/047648 A1 | 3/2014 |
| WO | WO 2014/066435 A1 | 5/2014 |
| WO | WO 2014/066552 A1 | 5/2014 |
| WO | WO 2014/089379 A1 | 6/2014 |

OTHER PUBLICATIONS

Amiri-Kordestani et al. JNCI J Natl Cancer Inst. vol. 104, Issue 8. (2012): 2 pages.*
Albert et al. (Clin Cancer Res 2007;13(10) May 15, 2007).*
Zabludoff et al. (Mol Cancer Ther. 2008;7:2955-2966).*
Bartucci et al. ("Therapeutic targeting of Chk1 in NSCLC stem cells during chemotherapy." Cell Death and Differentiation (2012); 19:768-778). (Year: 2012).*
Voskoglou-Nomikos et al. "Clinical Predictive Value of the in Vitro Cell Line, Human Xenograft, and Mouse Allograft Preclinical Cancer Models." vol. 9, 4227-4239, Sep. 15, 2003 (Year: 2003).*
International Search Report and Written Opinion, dated Sep. 24, 2015, in connection with Application No. PCT/US2015/036137.
International Search Report, dated Feb. 6, 2014, in connection with Application No. PCT/US2013/073482.
International Search Report and Written Opinion in connection with Application No. PCT/US2012/043897, dated Jul. 20, 2012.
International Search Report and Written Opinion in connection with Application No. PCT/US2012/043896, dated Oct. 9, 2012.
International Search Report and Written Opinion in connection with Application No. PCT/US2012/043895, dated Aug. 28, 2012.
International Search Report and Written Opinion, dated Oct. 1, 2015, in connection with Application No. PCT/US2015/032879.
International Search Report and Written Opinion, dated Jan. 29, 2014, in connection with Application No. PCT/US2013/073457.
International Search Report, dated Jan. 30, 2014, in connection with Application No. PCT/US2013/073477.
Office Communication, dated Jun. 27, 2014, for U.S. Appl. No. 14/098,640.
International Search Report, dated Feb. 17, 2014, in connection with Application No. PCT/US2013/073471.
International Search Report and Written Opinion, dated Jan. 29, 2015, in connection with Application No. PCT/US2014/068713.
International Search Report, dated Apr. 1, 2014, in connection with Application No. PCT/US2013/073468.
International Search Report and Written Opinion in connection with Application No. PCT/US2011/041705, dated Aug. 23, 2011.
International Search Report and Written Opinion in connection with Application No. PCT/US2016/054996, dated Jan. 19, 2017.
[No Author Listed], Guidance for Industry: Estimating the Maximum Safe Starting Dose in Initial Clinical Trials for Therapeutics in Adult Healthy Volunteers. U.S. Department of Health and Human Services, Food and Drug Administration, Center for Drug Evaluation and Research. Jul. 2005. 29 pages.
Abdel-Magid, Inhibitors of ATR Kinase for Treatment of Cancer. ACS Med Chem Lett. Jun. 13, 2013;4(8):688-9. doi: 10.1021/ml4002198. eCollection 2013.
Ahmed et al., Synthesis and anti-tumor activities of some new pyridines and pyrazolo[1,5-a]pyrimidines. Eur J Med Chem. Sep. 2009;44(9):3519-23. doi: 10.1016/j.ejmech.2009.03.042. Epub Apr. 8, 2009.
Ahmed et al., Synthesis of some Pyrazolopyrimidines as Purine Analogues. J Heterocyclic Chem. 2007;44(4):803-10.
Ammar et al., 3-Ethoxycarbonylmethylenequinoxalin-2-one in heterocyclic synthesis. Part 1: Synthesis of new substituted and condensed quinoxalines. Afinidad. 2005;62(516):151-60.
Bhattacharya et al., Polymorphism in Pharmaceutical Solids. Brittain, ed. CRC Press. Jul. 27, 2009. p. 334.
Boylan et al., Parenteral Products. Chapter 12. In: Modern Pharmaceuticals. Fourth Edition. 1997:34 pages.
Cerami et al., The cBio cancer genomics portal: an open platform for exploring multidimensional cancer genomics data. Cancer Discov. May 2012;2(5):401-4. doi: 10.1158/2159-8290.CD-12-0095.
Charrier et al, Discovery of potent and selective inhibitors of ataxia telangiectasia mutated and Rad3 related (ATR) protein kinase as potential anticancer agents. J Med Chem. Apr. 14, 2011;54(7):2320-30. doi: 10.1021/jm101488z. Epub Mar. 17, 2011. E-pub version.
Charrier et al., Discovery of Potent and Selective Inhibitors of ATR (Ataxia Telangiectasia Mutated and Rad3 Related) as Potential AntiCancer Agents. Supplementary Information, Apr. 14, 2011: 47 pages.
Charrier, Discovery of potent and selective inhibitors of Ataxia Telangiectasia mutated and Rad3 related (ATR) protein kinase as potential anticancer agents. Presentation, ACS Denver 2011. Aug. 28, 2011. 21 pages.
Chawla et al., Challenges in Polymorphism of Pharmaceuticals. CRIPS. 2004;5(1):9-12.
Clark et al., Mass spectrometry of pyrrolo [2, 3-13] pyrazines and pyrazino [2, 3- b]indole. Organic Mass Spectrometry. 1977;12(7):421-3.
Cliby et al., Overexpression of a kinase-inactive ATR protein causes sensitivity to DNA-damaging agents and defects in cell cycle checkpoints. EMBO J. Jan. 2, 1998;17(1):159-69.
Cortez, Caffeine inhibits checkpoint responses without inhibiting the ataxia-telangiectasia-mutated (ATM) and ATM- and Rad3-related (ATR) protein kinases. J Biol Chem. Sep. 26, 2003;278(39):37139-45.
Curtin, Inhibiting the DNA damage response as a therapeutic manoeuvre in cancer. Br J Pharmacol. Aug. 2013;169(8):1745-65. doi: 10.1111/bph.12244.

(56) References Cited

OTHER PUBLICATIONS

El-Emary, Synthesis and Biological Activity of Some New Pyrazolo[3,4-b]pyrazines. J Chinese Chem Soc (Taipei, Taiwan). 2006;53(2): 391-401.

Elnagdi et al., Synthesis of Substituted Azaindenes: Synthesis of New Pyrazolo[1,5-a]pyrimidine Derivatives. Bull Chem Soc Jpn. 1990;63(6):1854-56.

Fernandes et al., Synthesis and Biological Activity of Heterocyclic Derivatives derived from Ethyl-2-hydroxy-quinoxaline-3-carboxylate. J Indian Chem Soc. 1986;63(4):427-9.

Finlay et al., Modulation of DNA repair by pharmacological inhibitors of the PIKK protein kinase family. Bioorg Med Chem Lett. Sep. 1, 2012;22(17):5352-9. doi: 10.1016/j.bmcl.2012.06.053. Epub Jul. 1, 2012.

Flynn et al., Alternative lengthening of telomeres renders cancer cells hypersensitive to ATR inhibitors. Science. Jan. 16, 2015;347(6219):273-7. doi: 10.1126/science.1257216.

Fokas et al., Targeting ATR in DNA damage response and cancer therapeutics. Cancer Treat Rev (2013), http://dx.doi.org/10.1016/j.ctrv.2013.03.002.

Fokas et al., Targeting ATR in vivo using the novel inhibitor VE-822 results in selective sensitization of pancreatic tumors to radiation. Cell Death Dis. Dec. 6, 2012;3:e441. doi: 10.1038/cddis.2012.181.

Foote et al., Discovery of 4-{4-[(3R)-3-Methylmorpholin-4-yl]-6-[1-(methylsulfonyl)cyclopropyl]pyrimidin-2-yl}-1H-indole (AZ20): a potent and selective inhibitor of ATR protein kinase with monotherapy in vivo antitumor activity. J Med Chem. Mar. 14, 2013;56(5):2125-38. doi: 10.1021/jm301859s.

Foote et al., Drugging ATR: progress in the development of specific inhibitors for the treatment of cancer. Future Med Chem. 2015;7(7):873-91. doi: 10.4155/fmc.15.33.

Gentili et al., Alpha2-adrenoreceptors profile modulation. 4. From antagonist to agonist behavior. J Med Chem. Jul. 24, 2008;51(14):4289-99. doi: 10.1021/jm800250z. Epub Jun. 25, 2008.

Guichard et al., The pre-clinical in vitro and in vivo activity of AZD6738: A potent and selective inhibitor of ATR kinase. [abstract]. In: Proceedings of the 104th Annual Meeting of the American Association for Cancer Research; Apr. 6-10, 2013; Washington, DC. Philadelphia (PA): AACR; Cancer Res 2013;73(8 Suppl):Abstract nr 3343. doi:10.1158/1538-7445.AM2013-3343.

Hackam et al., Translation of research evidence from animals to humans. JAMA. Oct. 11, 2006;296(14):1731-2.

Hall et al., Potentiation of tumor responses to DNA damaging therapy by the selective ATR inhibitor VX-970. Oncotarget. Jul. 30, 2014;5(14):5674-85.

Hall-Jackson et al., ATR is a caffeine-sensitive, DNA-activated protein kinase with a substrate specificity distinct from DNA-PK. Oncogene. Nov. 18, 1999;18(48):6707-13.

Hickson et al., Identification and characterization of a novel and specific inhibitor of the ataxia-telangiectasia mutated kinase ATM. Cancer Res. Dec. 15, 2004;64(24):9152-9.

Hilton et al., Identification and characterisation of 2-aminopyridine inhibitors of checkpoint kinase 2. Bioorg Med Chem. Jan. 15, 2010;18(2):707-18. doi: 10.1016/j.bmc.2009.11.058. Epub Dec. 6, 2009.

Ho, Studies on the Synthesis of New 3-(3,5-Diamino-1-substituted-pyrazol-4-yl)azo-thieno[2,3-b]pyridines and 3-(2-Amino-5,7-disubstituted-pyrazolo[1,5-a]pyrimidine-3-yl)azo-thieno[2,3-b]pyridines. Journal of the Chinese Chemical Society. 1999; 46:955-62.

Hocke et al., A synthetic lethal screen identifies ATR-inhibition as a novel therapeutic approach for POLD1-deficient cancers. Oncotarget. Feb. 9, 2016;7(6):7080-95. doi: 10.18632/oncotarget.6857.

Hubackova et al., Regulation of the PML tumor suppressor in drug-induced senescence of human normal and cancer cells by JAK/STAT-mediated signaling. Cell Cycle. Aug. 1, 2010;9(15):3085-99. doi: 10.4161/cc.9.15.12521. Epub Aug. 26, 2010.

Huntoon et al., ATR inhibition broadly sensitizes ovarian cancer cells to chemotherapy independent of BRCA status. Cancer Res. Jun. 15, 2013;73(12):3683-91. doi: 10.1158/0008-5472.CAN-13-0110. Epub Apr. 2, 2013.

Hussein, Novel Synthesis of Some New Pyrimido[1,6-a]pyrimidine and Pyrazolo[1,5-a]pyrimidine Derivatives. J Heterocyclic Chem. 2012;49(2):446-51.

Jiang et al., Synthesis and cytotoxicity evaluation of novel indolylpyrimidines and indolylpyrazines as potential antitumor agents. Bioorg Med Chem. May 2001;9(5):1149-54.

Jones et al., Discovery of AZD6738, a potent and selective inhibitor with the potential to test the clinical efficacy of ATR kinase inhibition in cancer patients. [abstract]. In: Proceedings of the 104th Annual Meeting of the American Association for Cancer Research; Apr. 6-10, 2013; Washington, DC. Philadelphia (PA): AACR; Cancer Res 2013;73(8 Suppl):Abstract nr 2348. doi:10.1158/1538-7445.AM2013-2348.

Jordan et al., Tamoxifen: a most unlikely pioneering medicine. Nat Rev Drug Discov. Mar. 2003;2(3):205-13.

Josse et al., ATR inhibitors VE-821 and VX-970 sensitize cancer cells to topoisomerase i inhibitors by disabling DNA replication initiation and fork elongation responses. Cancer Res. Dec. 1, 2014;74(23):6968-79. doi: 10.1158/0008-5472.CAN-13-3369.

Katritzky et al., Efficient synthesis of 3,5-functionalized isoxazoles and isoxazolines via 1,3-dipolar cycloaddition reactions of 1-propargyl- and 1- allylbenzotriazoles. J Heterocyclic Chem. 2000;37(6):1505-10.

Kedar et al., Interaction between PARP-1 and ATR in mouse fibroblasts is blocked by PARP inhibition. DNA Repair (AMST). Nov. 1, 2008;7(11):1787-98. doi: 10.1016/j.dnarep.2008.07.006.

Kim et al., Substrate specificities and identification of putative substrates of ATM kinase family members. J Biol Chem. Dec. 31, 1999;274(53):37538-43.

Klicnar et al., Studien in der chinoxalinreihe III. Synthese, reaktionen und ir-spektren einiger 3-hydroxy-2-carboxymethylchinoxalin-derivate. Collection of Czechoslovak Chemical Communications. 1965;30(9):3092-101.

Knight et al., A pharmacological map of the PI3-K family defines a role for p110alpha in insulin signaling. Cell. May 19, 2006;125(4):733-47.

Krajewska et al., ATR inhibition preferentially targets homologous recombination-deficient tumor cells. Oncogene. Jun. 2015;34(26):3474-81. doi: 10.1038/onc.2014.276.

Kumpaty et al., Synthesis of N-methyl secondary amines. Synth Commun. 2003;33(8):1411-6.

Kurasawa et al., Revised Structure for the Product from the Reaction of 3-Hydrazinocarbonylmethylene-2-oxo-1,2,3,4-tetrahydroquinoxaline with Nitrous Acid. Chem. Pharm. Bull. 1984;32(10):4140-3.

Kwok et al., ATR inhibition induces synthetic lethality and overcomes chemoresistance in TP53- or ATM-defective chronic lymphocytic leukemia cells. Blood. Feb. 4, 2016;127(5):582-95. doi: 10.1182/blood-2015-05-644872.

Lau et al., Pre-clinical efficacy of the ATR inhibitor AZD6738 in combination with the PARP inhibitor olaparib. [abstract]. In: Proceedings of the AACR-NCI-EORTC International Conference: Molecular Targets and Cancer Therapeutics; Nov. 5-9, 2015; Boston, MA. Philadelphia (PA): AACR; Mol Cancer Ther 2015;14(12 Suppl 2):Abstract nr C60.

Luo et al., Molecular dynamics-based self-organizing molecular field analysis on 3-amino-6-arylpyrazines as the ataxia telangiectasia mutated and Rad3 related (ATR) protein kinase inhibitors. Med Chem Res. Published online: Jun. 19, 2013. 12 pages.

McKenna et al., Evaluation of a potent and highly selective inhibitor of ATR kinase: an approach to selectively sensitize cancer cells to genotoxic drugs. Abstract. Mar. 31, 2012. 1page.

McKenna et al., Evaluation of the first potent and highly selective inhibitor of ATR inhibitor, VE-821: an approach to selectively sensitize cancer cells to ionizing radiation and hypoxia. Poster. Mar. 31, 2012. 1 page.

McMahon, VEGF Receptor Signaling in Tumor Angiogenesis. The Oncologist. 2000;5(suppl 1):3-10.

(56) References Cited

OTHER PUBLICATIONS

Menezes et al., A synthetic lethal screen reveals enhanced sensitivity to ATR inhibitor treatment in mantle cell lymphoma with ATM loss-of-function. Mol Cancer Res. Jan. 2015;13(1):120-9. doi: 10.1158/1541-7786.MCR-14-0240.

Middleton et al., ATR as a Therapeutic Target. In: Advances in DNA Repair in Cancer Therapy. Cancer Drug Discovery and Development. 2013;72:211-28.

Mohni et al., A Synthetic Lethal Screen Identifies DNA Repair Pathways that Sensitize Cancer Cells to Combined ATR Inhibition and Cisplatin Treatments. PLoS One. May 12, 2015;10(5):e0125482. doi: 10.1371/journal.pone.0125482.

Mohni et al., ATR pathway inhibition is synthetically lethal in cancer cells with ERCC1 deficiency. Cancer Res. May 15, 2014;74(10):2835-45. doi: 10.1158/0008-5472.CAN-13-3229.

Montano et al., Sensitization of human cancer cells to gemcitabine by the Chk1 inhibitor MK-8776: cell cycle perturbation and impact of administration schedule in vitro and in vivo. BMC Cancer. Dec. 21, 2013;13:604. doi: 10.1186/1471-2407-13-604.

Nakamura et al., Bimodal Chemiluminescence of 8-Chlorostyryl-6-phenylethynylimidazopyrazinone: Large Bathochromic Shift Caused by a Styryl Group at 8-Position. Tetrahedron Letters. 1998;39:301-4.

Nghiem et al., ATR is not required for p53 activation but synergizes with p53 in the replication checkpoint. J Biol Chem. Feb. 8, 2002;277(6):4428-34.

Otero et al., Synthesis of Acyclo-C-nucleoside Analogs from 2,3:4,5-Di-Oisopropylidene-D-xylose. J Carbohydrate Chem. 2005;24:809-29.

Otero et al., Synthesis of Iso-C-nucleoside Analogues from I-(Methyl 2-0-benzyl-4,6-O-benzylidene-3-deoxy-et-D-altropyranosid-3-yl)but-3-yn-2-ones. Z. Naturforsch. 2005; 60b:1175-85.

Peasland et al., Identification and evaluation of a potent novel ATR inhibitor, NU6027, in breast and ovarian cancer cell lines. British Journal of Cancer. Jul. 2011; 105(3):372-81.

Pinedo et al., Translational Research: The Role of VEGF in Tumor Angiogenesis. The Oncologist. 2000;5(suppl 1):1-2.

Pires et al., Targeting radiation-resistant hypoxic tumour cells through ATR inhibition. Br J Cancer. Jul. 10, 2012;107(2):291-9. doi: 10.1038/bjc.2012.265. Epub Jun. 19, 2012.

Pollard et al. Defining optimal dose schedules for ATR inhibitors in combination with DNA damaging drugs: Informing clinical studies of VX-970, the first-in-class ATR inhibitor. Proceedings: AACR Annual Meeting. Apr. 16-20, 2016.

Pollard, Inhibition of the DNA Damage Response Kinase, ATR, as a Promising Anti-Cancer Approach. Presentation, Mar. 8, 2012. 28 pages.

Prevo et al., The novel ATR inhibitor VE-821 increases sensitivity of pancreatic cancer cells to radiation and chemotherapy. Cancer Biol Ther. Sep. 2012;13(11):1072-81. doi: 10.4161/cbt.21093. Epub Jul. 24, 2012.

Qi et al., Chemi- and Bio-Iuminescence of Coelenterazine Analogues with Phenyl Homologues at the C-2 Position. J Chem Soc. Perkin Trans 1. 1992:1607-11.

Ram et al., Synthesis of bioisosteric pyrazolo[1,5-a ]pyrimidines as leishmanicides. Indian J Chemistry. 1995;34b:514-20.

Reaper et al., Evaluation of a potent and highly selective inhibitor of ATR kinase: an approach to selectively sensitize cancer cells to genotoxic drugs. 102nd AACR Annual Meeting. Orlando, 2011. Abstract.

Reaper et al., Evaluation of a Potent and Highly Selective Inhibitor of ATR Kinase: An Approach to Selectively Sensitize Cancer Cells to Genotoxic Drugs. 102nd AACR Annual Meeting. Orlando, 2011. Poster.

Reaper et al., Selective killing of ATM- or p53-deficient cancer cells through inhibition of ATR. Nat Chem Biol. Apr. 13, 2011;7(7):428-30. doi: 10.1038/nchembio.573. Advance online publication.

Reaper et al., Selective Killing of ATM- or p53-deficient cancer cells through inhibition of ATR. Presentation. Nov. 2011:25 pages.

Reaper et al., Selective Killing of ATM- or p53-deficient cancer cells through inhibition of ATR. Presentation. Nov. 2011:31 pages.

Reaper et al., Selective killing of ATM- or p53-deficient cancer cells through inhibition of ATR. Supplementary Information. Nature Chemical Biology. Apr. 13, 2011. doi:10.1038/nchembio.573. 26 pages.

Reaper et al., Selective killing of ATM- or p53-deficient cancer cells through inhibition of ATR. Nat Chem Biol. Apr. 13, 2011;7(7):428-30. doi: 10.1038/nchembio.573.

Ried et al., Synthese neuer Heterocyclen ausgehend von Aminopyrazolen. Chemiker•Zeilung. 1989;181-3.

Saito et al., Synthesis and in vitro evaluation of botryllazine B analogues as a new class of inhibitor against human aldose reductase. Tetrahedron. 2009;65(15):3019-26.

Sanjiv et al., Cancer-Specific Synthetic Lethality between ATR and CHK1 Kinase Activities. Cell Rep. Jan. 12, 2016;14(2):298-309. doi: 10.1016/j.celrep.2015.12.032.

Sarkaria et al., Inhibition of ATM and ATR kinase activities by the radiosensitizing agent, caffeine. Cancer Res. Sep. 1, 1999;59(17):4375-82.

Sevilla et al., Microwave-assisted synthesis of 1,3-dihydro-[1,2,5]thiadiazolo[3,4-b]pyrazine-2,2-dioxides. Tetrahedron Letters. 2006;47(48):8603-6.

Smith et al., Addition to Carbon-Hetero Multiple Bonds. Chapter 16. In: March's Advanced Organic Chemistry: Reactions, Mechanisms, and Structure, Sixth Edition. John Wiley & Sons, Inc. 2007. 26 pages.

Sugimoto et al., Imidazopteridines. I. Synthesis of Imidazo[1,2-c]pteridine and Its Alkyl Derivatives. Bull Chem Soc Japan. 1977;50(10):2744-7.

Teng et al., Pharmacologic inhibition of ATR and ATM offers clinically important distinctions to enhancing platinum or radiation response in ovarian, endometrial, and cervical cancer cells. Gynecol Oncol. Mar. 2015;136(3):554-61. doi: 10.1016/j.ygyno.2014.12.035.

Toledo et al., A cell-based screen identifies ATR inhibitors with synthetic lethal properties for cancer-associated mutations. Nat Struct Mol Biol. Jun. 2011;18(6):721-7. doi: 10.1038/nsmb.2076.

Vendetti et al., The orally active and bioavailable ATR kinase inhibitor AZD6738 potentiates the anti-tumor effects of cisplatin to resolve ATM-deficient non-small cell lung cancer in vivo. Oncotarget. Dec. 29, 2015;6(42):44289-305. doi: 10.18632/oncotarget.6247.

Vippagunta et al., Crystalline solids. Adv Drug Deliv Rev. May 16, 2001;48(1):3-26.

Ward et al., Histone H2AX is phosphorylated in an ATR-dependent manner in response to replicational stress. J Biol Chem. Dec. 21, 2001;276(51):47759-62. Epub Oct. 22, 2001.

Wilsker et al., Loss of ataxia telangiectasia mutated- and Rad3-related function potentiates the effects of chemotherapeutic drugs on cancer cell survival. Mol Cancer Ther. Apr. 2007;6(4):1406-13.

Wolff, Burger's Medicinal Chemistry and Drug Discovery. Fifth Edition. vol. I: Principles and Practice. 1995;975-7.

Wuts et al., Protection for the Amino Group. Chapter 7. In: Greene's Protective Groups in Organic Synthesis, 4th Edition. John Wiley & Sons, Inc. 2007. 235 pages.

Wuts et al., Protection for the Carbonyl Group. Chapter 4. In: Greene's Protective Groups in Organic Synthesis, 4th Edition. John Wiley & Sons, Inc. 2007. 106 pages.

Schoppy et al., Oncogenic stress sensitizes murine cancers to hypomorphic suppression of ATR, The Journal of Clinical Investigation, Jan. 2012, vol. 122, No. 1, pp. 241-252.

Wang et al., Cancer Research, 1992, vol. 52, p. 4824.

Vavrova et al., Radiation and Environmental Biophysics, 2013, vol. 52, No. 4, pp. 471-479.

Leszczynska et al., Radiotherapy and Oncology, 2016, vol. 121, pp. 232-238.

Bergenske et al., Mayo Foundation Poster, 2016.

Xiao et al., The Journal of Biological Chemistry, 2003, vol. 278, No. 4, pp. 21767-21773.

Wang et al., Molecular and Cellular Biology, 2007, vol. 27, No. 8, pp. 3098-3108.

Cheung-Ong et al., Chemistry and Biology, 2013, vol. 20, pp. 648-659.

(56) References Cited

OTHER PUBLICATIONS

Brunton et al., Goodman & Gillman's Pharmacological Basis of Therapeutics, Twelfth Edition, McGraw Hill, (2011), Chapters 60 and 61.
U.S. Appl. No. 15/967,110 of Charrier et al., filed Apr. 30, 2018.
U.S. Appl. No. 15/608,630 of Charrier et al., filed May 30, 2017.
U.S. Appl. No. 15/849,241 of Charrier et al., filed Dec. 20, 2017.
U.S. Appl. No. 15/633,477 of Ahmad et al., filed Jun. 26, 2017.
U.S. Appl. No. 15/763,366 of Pollard et al., filed Mar. 26, 2018.
U.S. Appl. No. 15/693,521 of Falcon et al., filed Sep. 1, 2017.
Cimprich et al., 2008, "ATR: An Essential Regulator of Genome Integrity," Nat Rev Mol Cell Biol. 9(8):616-627.
Parsels et al., "Assessment of Chk1 phosphorylation as a pharmacodynamic biomarker of Chk1 inhibition," Clin Cancer Res. 17(11): 3706-3715 (2011).
Liu et al., "Chk1 is an essential kinase that is regulated by ATR and required for the G2/M DNA damage checkpoint," Genes Dev. 14:1448-1459 (2000).
Day et al., "Approaches to modernize the combination drug development paradigm," 2016; Volume No. 8 (Issue No. 115): pp. 1-14.

* cited by examiner

METHOD FOR TREATING CANCER USING A COMBINATION OF CHK1 AND ATR INHIBITORS

CROSS-REFERENCE TO RELATED APPLICATIONS

The present application claims the benefit under 35 U.S.C. § 119 of U.S. Provisional Application No. 62/013,136, filed Jun. 17, 2014; U.S. Provisional Application No. 62/043,530, filed Aug. 29, 2014; U.S. Provisional Application No. 62/073,082, filed Oct. 31, 2014; and U.S. Provisional Application No. 62/161,438, filed May 14, 2015.

BACKGROUND OF THE INVENTION

ATR ("ATM and Rad3 related") is a key mediator of cellular responses to a DNA damage structure that is characterized by tracts of single stranded DNA coated by replication protein A (RPA). RPA coated single stranded DNA commonly arises as a result of replication stress, which occurs when a cell attempts to replicate DNA through unresolved DNA damage lesions. Failure to repair replication stress can lead to lethal double strand breaks or deleterious DNA mutation. ATR along with its substrates coordinates multiple cell functions in response to replication stress including cell cycle control, DNA replication and DNA damage repair. Chk1 is a principle substrate for ATR.

Cancer cells typically have high levels of background replicative stress that can arise from oncogene expression, hypoxia or defects in other repair pathways eg base excision repair. This can lead to a reliance on ATR for survival in some cancer cells. Additionally, cells require ATR to resolve replication stressfollowing treatment with many DNA damaging drugs and ionising radiation, or from treatment with agents that block other repair pathways such as PARP inhibitors, which block base excision repair.

Inhibitors of the ATR signaling pathway have been shown to reduce cell survival in some cancer cells that either express oncogenes such as Cyclin E or Myc (See Schoppy et. al., *J Clin Invest*, 2012, vol. 122, pp. 241-52); are under an hypoxic environment (See Pires et. al., *Br J Cancer.* 2012, vol. 107, pp. 291-99); or that carry defects in other DNA repair proteins such as ERCC1 (Mohni et. al., *Cancer Res*, 2014, vol. 74, pp. 2835-45). Additionally, inhibitors of the ATR pathway have been shown to sensitise some cancer cells to the cytotoxic effects of multiple DNA damaging drugs and ionizing radiation, or to inhibitors of other repair pathways for example PARP inhibitors. In contrast, normal cells have been shown to tolerate inhibition of ATR, either as single agents or when used in combination with other agents. This is attributed to activation of compensatory DNA repair signaling in normal cells, which is often not available to cancer cells.

SUMMARY OF THE INVENTION

The present invention relates to methods of treating cancer in a patient by administering a compound useful as an inhibitor of ATR protein kinase in combination with a compound useful as an inhibitor of Chk1 protein kinase. The aforementioned combination displayed a surprising synergistic effect in treating cancer despite the targeted protein kinases being within the same biological pathway. Moreover, the present invention also relates to methods of treating cancer by administering a compound useful as an inhibitor of ATR protein kinase; administering a compound useful as an inhibitor of Chk1 protein kinase; as well as administering one or more DNA damaging agents to a patient.

DETAILED DESCRIPTION OF THE INVENTION

Figure 1:
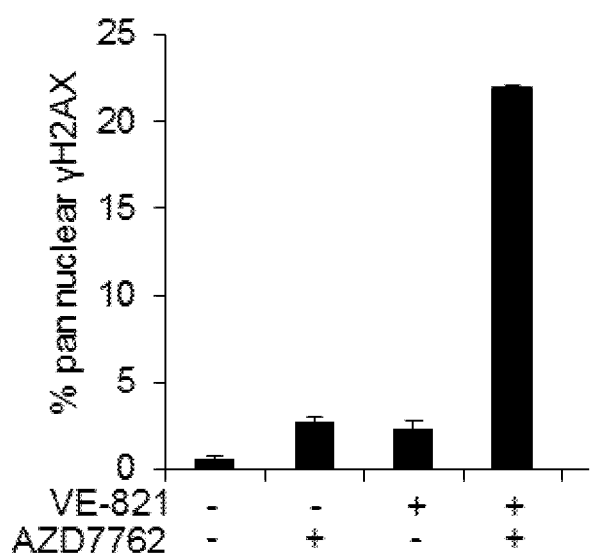
FIG. 1: graph showing pan nuclear γH2AX H2AX induction in an U2OS cell line treated alone and in combination with AZD7762 and VE-821.

One or more aspects of the present invention provides a method of treating cancer in a patient comprising administering a first compound that inhibits ATR protein kinase; and administering a second compound that inhibits Chk1 protein kinase. Another aspect of the present invention provides a method of treating cancer in a patient comprising administering a first compound that inhibits ATR protein kinase; administering a second compound that inhibits Chk1 protein kinase; and administering one or more additional therapeutic agents.

Compounds

In another aspect of the present invention, the compound that inhibits ATR protein kinase is represented by Formula I:

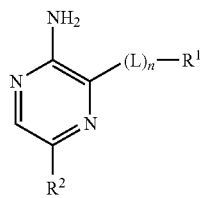

I or a pharmaceutically acceptable salt thereof,
wherein $R^1$ is a 5-6 membered monocyclic aryl or heteroaryl ring having 0-4 heteroatoms independently selected from nitrogen, oxygen, or sulfur, wherein said monocyclic aryl or heteroaryl ring is optionally fused to another ring to form an 8-10 membered bicyclic aryl or heteroaryl ring having 0-6 heteroatoms independently selected from nitrogen, oxygen, or sulfur; each $R^1$ is optionally substituted with 1-5 $J^1$ groups;

$R^2$ is a 5-6 membered monocyclic aryl or heteroaryl ring having 0-3 heteroatoms independently selected from nitrogen, oxygen, or sulfur, wherein said monocyclic aryl or heteroaryl ring is optionally fused to another ring to form an 8-10 membered bicyclic aryl or heteroaryl ring having 0-4 heteroatoms independently selected from nitrogen, oxygen, or sulfur; each $R^2$ is optionally substituted with 1-5 $J^2$ groups;

L is —C(O)NH— or —C(O)N($C_{1-6}$alkyl)-;

n is 0 or 1;

Each $J^1$ and $J^2$ is independently halo, —CN, —$NO_2$, —$V^1$—R, or —$(V^2)_m$—Q;

$V^1$ is a $C_{1-10}$aliphatic chain wherein 0-3 methylene units are optionally and independently replaced with O, NR″, S, C(O), S(O), or S(O)$_2$; $V^1$ is optionally substituted with 1-6 occurrences of $J^{V1}$;

$V^2$ is a $C_{1-10}$aliphatic chain wherein 0-3 methylene units are optionally and independently replaced with O, NR″, S, C(O), S(O), or S(O)$_2$; $V^2$ is optionally substituted with 1-6 occurrences of $J^{V2}$;

m is 0 or 1;

Q is a 3-8 membered saturated or unsaturated monocyclic ring having 0-4 heteroatoms independently selected from nitrogen, oxygen, or sulfur, or a 9-10 membered saturated or unsaturated bicyclic ring having 0-6 heteroatoms independently selected from nitrogen, oxygen, or sulfur; each Q is optionally substituted with 0-5 $J^Q$;

each $J^{V1}$ or $J^{V2}$ is independently halogen, CN, $NH_2$, $NO_2$, $C_{1-4}$aliphatic, NH($C_{1-4}$aliphatic), N($C_{1-4}$aliphatic)$_2$, OH, O($C_{1-4}$aliphatic), $CO_2$H, $CO_2$($C_{1-4}$aliphatic), C(O)$NH_2$, C(O)NH($C_{1-4}$aliphatic), C(O)N($C_{1-4}$aliphatic)$_2$, NHCO ($C_{1-4}$aliphatic), N($C_{1-4}$aliphatic)CO($C_{1-4}$aliphatic), $SO_2$ ($C_{1-4}$aliphatic), $NHSO_2$($C_{1-4}$aliphatic), or N($C_{1-4}$aliphatic)$SO_2$($C_{1-4}$aliphatic), wherein said $C_{1-4}$aliphatic is optionally substituted with halo;

R is H or $C_{1-6}$aliphatic wherein said $C_{1-6}$aliphatic is optionally substituted with 1-4 occurrences of $NH_2$, NH($C_{1-4}$aliphatic), N($C_{1-4}$aliphatic)$_2$, halogen, $C_{1-4}$aliphatic, OH, O($C_{1-4}$aliphatic), $NO_2$, CN, $CO_2$H, $CO_2$($C_{1-4}$aliphatic), CO($C_{1-4}$aliphatic), O(halo$C_{1-4}$aliphatic), or halo$C_{1-4}$aliphatic;

each $J^Q$ is independently halo, oxo, CN, $NO_2$, X—R, or —$(X)_p$-$Q^4$;

p is 0 or 1;

X is $C_{1-10}$aliphatic; wherein 1-3 methylene units of said $C_{1-6}$aliphatic are optionally replaced with —NR, —O—, —S—, C(O), S(O)$_2$, or S(O); wherein X is optionally and independently substituted with 1-4 occurrences of $NH_2$, NH($C_{1-4}$aliphatic), N($C_{1-4}$aliphatic)$_2$, halogen, $C_{1-4}$aliphatic, OH, O($C_{1-4}$aliphatic), $NO_2$, CN, CO($C_{1-4}$aliphatic), $CO_2$H, $CO_2$($C_{1-4}$aliphatic), C(O)$NH_2$, C(O)NH ($C_{1-4}$aliphatic), C(O)N($C_{1-4}$aliphatic)$_2$, SO($C_{1-4}$ aliphatic), $SO_2$($C_{1-4}$aliphatic), $SO_2$NH($C_{1-4}$aliphatic), $SO_2$N($C_{1-4}$aliphatic)$_2$, NHC(O)($C_{1-4}$aliphatic), N($C_{1-4}$aliphatic)C(O)($C_{1-4}$aliphatic), wherein said $C_{1-4}$aliphatic is optionally substituted with 1-3 occurrences of halo;

$Q^4$ is a 3-8 membered saturated or unsaturated monocyclic ring having 0-4 heteroatoms independently selected from nitrogen, oxygen, or sulfur, or a 8-10 membered saturated or unsaturated bicyclic ring having 0-6 heteroatoms independently selected from nitrogen, oxygen, or sulfur; each $Q^4$ is optionally substituted with 1-5 $J^{Q4}$;

$J^{Q4}$ is halo, CN, or $C_{1-4}$alkyl wherein up to 2 methylene units are optionally replaced with O, NR*, S, C(O), S(O), or S(O)$_2$;

R is H or $C_{1-4}$alkyl wherein said $C_{1-4}$alkyl is optionally substituted with 1-4 halo;

R', R", and R* are each independently H, $C_{1-4}$alkyl, or is absent; wherein said $C_{1-4}$alkyl is optionally substituted with 1-4 halo.

In some embodiments, L is —C(O)NH—; and $R^1$ and $R^2$ are phenyl.

In another embodiment the compound that inhibits ATR kinase is represented by Formula I-a:

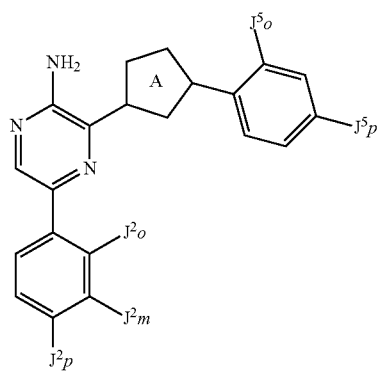

I-a wherein
Ring A is

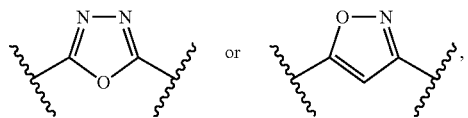 [SMILES: *c1nnc(*)o1 ; *c1cc(*)on1]

$J^5o$ is H, F, Cl, $C_{1-4}$aliphatic, O($C_{1-3}$aliphatic), or OH;
$J^5p$ is

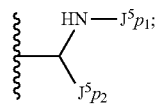

$J^5p_1$ is H, $C_{1-4}$aliphatic, oxetanyl, tetrahydrofuranyl, tetrahydropyranyl; wherein $J^5p_1$ is optionally substituted with 1-2 occurrences of OH or halo;
$J^5p_2$ is H, methyl, ethyl, $CH_2F$, $CF_3$, or $CH_2OH$;
$J^2o$ is H, CN, or $SO_2CH_3$;
$J^2m$ is H, F, Cl, or methyl;
$J^2p$ is —$SO_2(C_{1-6}alkyl)$, —$SO_2(C_{3-6}cycloalkyl)$, —$SO_2(4-6$ membered heterocyclyl), —$SO_2(C_{1-4}alkyl)N(C_{1-4}alkyl)_2$, or —$SO_2(C_{1-4}alkyl)$-(4-6 membered heterocyclyl), wherein said heterocyclyl contains 1 heteroatom selected from oxygen, nitrogen, or sulfur; and wherein said $J^2p$ is optionally substituted with 1-3 occurrences halo, OH, or O($C_{1-4}$alkyl).

In some embodiments, Ring A is

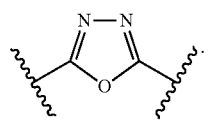 [SMILES: *c1nnc(*)o1]

In other embodiments, Ring A is

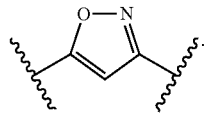 [SMILES: *c1cc(*)on1]

In some embodiments, the compound that inhibits ATR kinase is selected from:

VE-821

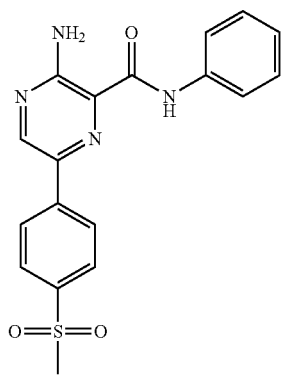

VE-822

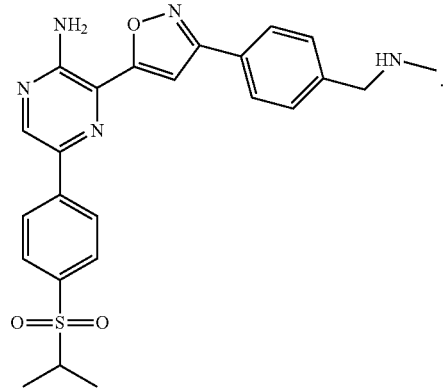

In certain embodiments, the compound that inhibits ATR kinase is:

VE-821

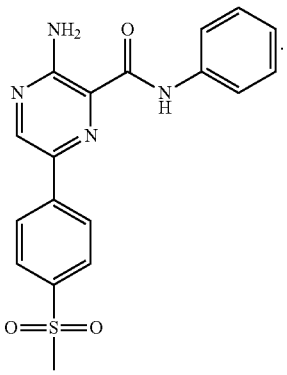

In another embodiment, the compound that inhibits ATR kinase is:

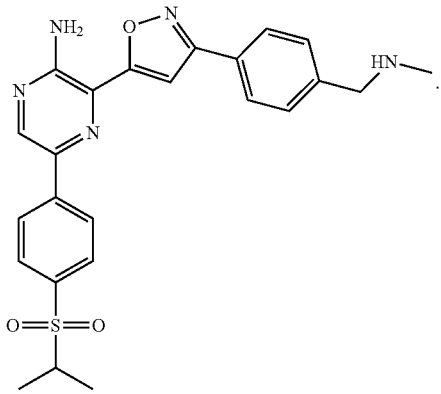

VE-822

In another aspect of the present invention, the compound that inhibits ATR protein kinase is represented by Formula II:

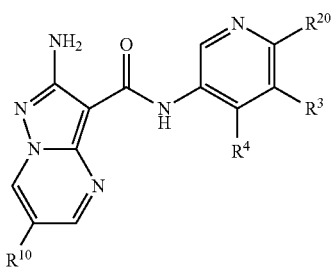

II or a pharmaceutically salt or derivative thereof, wherein:
$R^{10}$ is independently selected from fluoro, chloro, or —C($J^{10}$)$_2$CN;
$J^{10}$ is independently selected from H or $C_{1-2}$alkyl; or
two occurrences of $J^{10}$, together with the carbon atom to which they are attached, form a 3-4 membered optionally substituted carbocyclic ring;
$R^{20}$ is independently selected from H; halo; —CN; NH$_2$; a $C_{1-2}$alkyl optionally substituted with 0-3 occurrences of fluoro; or a $C_{1-3}$aliphatic chain wherein up to two methylene units of the aliphatic chain are optionally replaced with —O—, —NR$^a$—, —C(O)—, or —S(O)$_z$—;
$R^3$ is independently selected from H; halo; $C_{1-4}$alkyl optionally substituted with 1-3 occurrences of halo; $C_{3-4}$cycloalkyl; —CN; or a $C_{1-3}$aliphatic chain wherein up to two methylene units of the aliphatic chain are optionally replaced with —O—, —NR$^a$—, —C(O)—, or —S(O)$_z$;
$R^4$ is independently selected from $Q^1$ or a $C_{1-10}$aliphatic chain wherein up to four methylene units of the aliphatic chain are optionally replaced with —O—, —NR$^a$—, —C(O)—, or —S(O)$_z$—; each $R^4$ is optionally substituted with 0-5 occurrences of $J^{Q1}$; or
$R^3$ and $R^4$, taken together with the atoms to which they are bound, form a 5-6 membered aromatic or non-aromatic ring having 0-2 heteroatoms selected from oxygen, nitrogen or sulfur; the ring formed by $R^3$ and $R^4$ is optionally substituted with 0-3 occurrences of $J^Z$;

$Q^1$ is independently selected from a 3-7 membered fully saturated, partially unsaturated, or aromatic monocyclic ring, the 3-7 membered ring having 0-3 heteroatoms selected from oxygen, nitrogen or sulfur; or an 7-12 membered fully saturated, partially unsaturated, or aromatic bicyclic ring having 0-5 heteroatoms selected from oxygen, nitrogen, or sulfur;
$J^Z$ is independently selected from $C_{1-6}$aliphatic, =O, halo, or →O;
$J^{Q1}$ is independently selected from —CN; halo; =O; $Q^2$; or a $C_{1-8}$aliphatic chain wherein up to three methylene units of the aliphatic chain are optionally replaced with —O—, —NR$^a$—, —C(O)—, or —S(O)$_z$—; each occurrence of $J^{Q1}$ is optionally substituted by 0-3 occurrences of $J^R$; or
two occurrences of $J^{Q1}$ on the same atom, taken together with the atom to which they are joined, form a 3-6 membered ring having 0-2 heteroatoms selected from oxygen, nitrogen, or sulfur; wherein the ring formed by two occurrences of $J^{Q1}$ is optionally substituted with 0-3 occurrences of $J^X$; or
two occurrences of $J^{Q1}$, together with $Q^1$, form a 6-10 membered saturated or partially unsaturated bridged ring system;
$Q^2$ is independently selected from a 3-7 membered fully saturated, partially unsaturated, or aromatic monocyclic ring having 0-3 heteroatoms selected from oxygen, nitrogen, or sulfur; or an 7-12 membered fully saturated, partially unsaturated, or aromatic bicyclic ring having 0-5 heteroatoms selected from oxygen, nitrogen, or sulfur;
$J^R$ is independently selected from —CN; halo; =O; →O; $Q^3$; or a $C_{1-6}$aliphatic chain wherein up to three methylene units of the aliphatic chain are optionally replaced with —O—, —NR$^a$—, —C(O)—, or —S(O)$_z$—; each $J^R$ is optionally substituted with 0-3 occurrences of $J^T$; or
two occurrences of $J^R$ on the same atom, together with the atom to which they are joined, form a 3-6 membered ring having 0-2 heteroatoms selected from oxygen, nitrogen, or sulfur; wherein the ring formed by two occurrences of $J^R$ is optionally substituted with 0-3 occurrences of $J^X$; or
two occurrences of $J^R$, together with $Q^2$, form a 6-10 membered saturated or partially unsaturated bridged ring system;
$Q^3$ is a 3-7 membered fully saturated, partially unsaturated, or aromatic monocyclic ring having 0-3 heteroatoms selected from oxygen, nitrogen, or sulfur; or an 7-12 membered fully saturated, partially unsaturated, or aromatic bicyclic ring having 0-5 heteroatoms selected from oxygen, nitrogen, or sulfur;
$J^X$ is independently selected from —CN; =O; halo; or a $C_{1-4}$aliphatic chain wherein up to two methylene units of the aliphatic chain are optionally replaced with —O—, —NR$^a$—, —C(O)—, or —S(O)$_z$—;
$J^T$ is independently selected from halo, —CN; →O; =O; —OH; a $C_{1-6}$aliphatic chain wherein up to two methylene units of the aliphatic chain are optionally replaced with —O—, —NR$^a$—, —C(O)—, or —S(O)$_z$—; or a 3-6 membered non-aromatic ring having 0-2 heteroatoms selected from oxygen, nitrogen, or sulfur; each occurrence of $J^T$ is optionally substituted with 0-3 occurrences of $J^M$; or
two occurrences of $J^T$ on the same atom, together with the atom to which they are joined, form a 3-6 membered ring having 0-2 heteroatoms selected from oxygen, nitrogen, or sulfur; or two occurrences of $J^T$, together with $Q^3$, form a 6-10 membered saturated or partially unsaturated bridged ring system;

$J^M$ is independently selected from halo or $C_{1-6}$aliphatic;

J is H or Cl;

z is 0, 1 or 2; and $R^a$ is independently selected from H or $C_{1-4}$aliphatic.

In some embodiments, $R^{10}$ and $R^3$ are fluoro.

In other embodiments, $R^4$ is $Q^1$.

In still other embodiments, $Q^1$ is independently selected from piperidinyl and imidazolyl.

In yet another embodiment, the compound that inhibits ATR is represented by the structure:

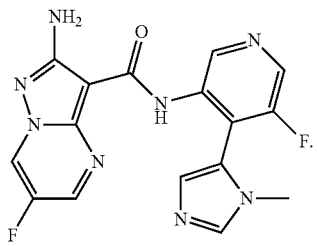 [SMILES: Cn1cncc1-c1c(F)cncc1NC(=O)c1c(N)nn2cc(F)cnc12]

In another embodiment, the compound that inhibits ATR is represented by Formula II-a:

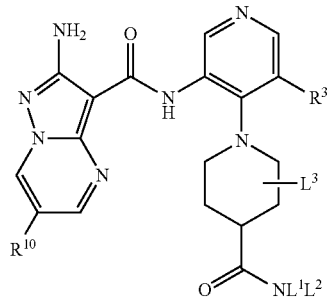

II-a or a pharmaceutically acceptable salt or prodrug thereof, wherein:

$R^{10}$ is independently selected from fluoro, chloro, or —C($J^{10}$)$_2$CN;

$J^{10}$ is independently selected from H or $C_{1-2}$alkyl; or two occurrences of $J^1$, together with the carbon atom to which they are attached, form an optionally substituted 3-4 membered carbocyclic ring;

$R^3$ is independently selected from H; chloro; fluoro; $C_{1-4}$alkyl optionally substituted with 1-3 occurrences of halo; $C_{3-4}$cycloalkyl; —CN; or a $C_{1-3}$aliphatic chain wherein up to two methylene units of the aliphatic chain are optionally replaced with —O—, —NR$^a$—, —C(O)—, or —S(O)$_z$;

$L^1$ is H; a 3-7 membered aromatic or non-aromatic ring having 0-2 heteroatoms selected from oxygen nitrogen or sulfur; or a $C_{1-6}$aliphatic chain wherein up to two methylene units of the aliphatic chain are optionally replaced with —O—, —NR$^a$—, —C(O)—, or —S(O)$_z$; each $L^1$ is optionally substituted with $C_{1-4}$aliphatic; —CN; halo; —OH; or a 3-6 membered non-aromatic ring having 0-2 heteroatoms selected from oxygen, nitrogen, or sulfur;

$L^2$ is H; a 3-7 membered aromatic or non-aromatic ring having 0-2 heteroatoms selected from oxygen nitrogen or sulfur; or a $C_{1-6}$aliphatic chain wherein up to two methylene units of the aliphatic chain are optionally replaced with —O—, —NR$^a$—, —C(O)—, or —S(O)$_z$; each $L^2$ is optionally substituted with $C_{1-4}$aliphatic; —CN; halo; —OH; or a 3-6 membered non-aromatic ring having 0-2 heteroatoms selected from oxygen, nitrogen, or sulfur; or $L^1$ and $L^2$, together with the nitrogen to which they are attached, form a Ring D; Ring D is optionally substituted with 0-5 occurrences of $J^G$;

$L^3$ is H; $C_{1-3}$aliphatic; or CN;

Ring D is independently selected from a 3-7 membered heterocyclyl ring having 1-2 heteroatoms selected from oxygen, nitrogen or sulfur; or an 7-12 membered fully saturated or partially unsaturated bicyclic ring having 1-5 heteroatoms selected from oxygen, nitrogen, or sulfur;

$J^G$ is independently selected from halo; —CN; —N(R$^o$)$_2$; →O; a 3-6 membered carbocycyl; a 3-6 membered heterocyclyl having 1-2 heteroatoms selected from oxygen nitrogen, or sulfur; or a $C_{1-4}$alkyl chain wherein up to two methylene units of the alkyl chain are optionally replaced with —O—, —NR$^a$—, —C(O)—, or —S(O)$_z$; each $J^G$ is optionally substituted with 0-2 occurrences of $J^K$.

two occurrences of $J^G$ on the same atom, together with the atom to which they are joined, form a 3-6 membered ring having 0-2 heteroatoms selected from oxygen, nitrogen, or sulfur; or two occurrences of $J^G$, together with Ring D, form a 6-10 membered saturated or partially unsaturated bridged ring system;

$J^K$ is a 3-7 membered aromatic or non-aromatic ring having 0-2 heteroatoms selected from oxygen, nitrogen, or sulfur;

z is 0, 1, or 2; and $R^a$ and $R^o$ are H or $C_{1-4}$alkyl.

In another embodiment, $R^1$ and $R^3$ are fluoro.

In still other embodiments, the compound that inhibits ATR is represented by the structure:

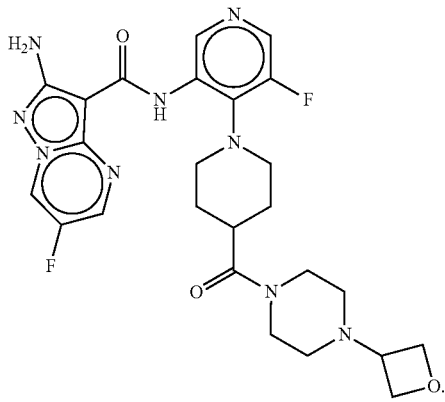

In yet another embodiment, the compound is selected from a compound described in WO 2010/071837 or WO 2014/089379.

In another embodiment, the compound that inhibits Chk1 kinase is independently selected from AZD7762, LY2603618, MK-8776, CHIR-124, and PF-477736. The process for making the Chk1 inhibitors is known to those skilled in the art.

In some embodiments, the variables are as depicted in the compounds of the disclosure including compounds in the tables herein.

For purposes of this application, it will be understood that the terms embodiment, example, and aspect are used interchangeably.

For purposes of this application, it will be understood that when two occurrences of $J^{Q1}$, together with $Q^1$, form a bridged ring system, the two occurrences of $J^{Q1}$ are attached to separate atoms of $Q^1$. Additionally, when two occurrences of $J^R$, together with $Q^2$, form a bridged ring system, the two occurrences of $J^R$ are attached to separate atoms of $Q^2$. Moreover, when two occurrences of $J^T$, together with $Q^3$, form a bridged ring system, the two occurrence of $J^T$ are attached to separate atoms of $Q^3$. Finally, when two occurrences of $J^G$, together with Ring D, form a bridged ring system, the two occurrences of $J^G$ are attached to separate atoms of Ring D.

For purposes of this application, it will be understood that the terms ATR, ATR kinase, and ATR protein kinase are used interchangeably. Similarly, the terms Chk1, Chk1 kinase, and Chk1 protein kinase are used interchangeably.

It will be understood by those skilled in the art that the arrow in →O represents a dative bond.

Compounds of this invention include those described generally herein, and are further illustrated by the classes, subclasses, and species disclosed herein. As used herein, the following definitions shall apply unless otherwise indicated. For purposes of this invention, the chemical elements are identified in accordance with the Periodic Table of the Elements, CAS version, Handbook of Chemistry and Physics, 75$^{th}$ Ed. Additionally, general principles of organic chemistry are described in "Organic Chemistry", Thomas Sorrell, University Science Books, Sausalito: 1999, and "March's Advanced Organic Chemistry", 5$^{th}$ Ed., Ed.: Smith, M. B. and March, J., John Wiley & Sons, New York: 2001, the entire contents of which are hereby incorporated by reference.

As described herein, a specified number range of atoms includes any integer therein. For example, a group having from 1-4 atoms could have 1, 2, 3, or 4 atoms.

As described herein, compounds of the invention may optionally be substituted with one or more substituents, such as are illustrated generally herein, or as exemplified by particular classes, subclasses, and species of the invention. It will be appreciated that the phrase "optionally substituted" is used interchangeably with the phrase "substituted or unsubstituted." In general, the term "substituted", whether preceded by the term "optionally" or not, refers to the replacement of hydrogen radicals in a given structure with the radical of a specified substituent. Unless otherwise indicated, an optionally substituted group may have a substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds.

Unless otherwise indicated, a substituent connected by a bond drawn from the center of a ring means that the substituent can be bonded to any position in the ring. In example i below, for instance, $J^1$ can be bonded to any position on the pyridyl ring. For bicyclic rings, a bond drawn through both rings indicates that the substituent can be bonded from any position of the bicyclic ring. In example ii below, for instance, $J^1$ can be bonded to the 5-membered ring (on the nitrogen atom, for instance), and to the 6-membered ring.

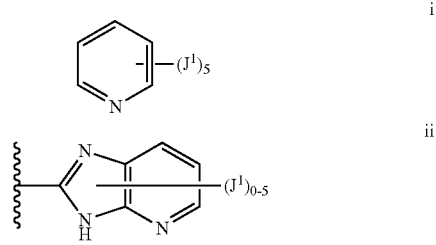

The term "stable", as used herein, refers to compounds that are not substantially altered when patiented to conditions to allow for their production, detection, recovery, purification, and use for one or more of the purposes disclosed herein. In some embodiments, a stable compound or chemically feasible compound is one that is not substantially altered when kept at a temperature of 40° C. or less, in the absence of moisture or other chemically reactive conditions, for at least a week.

The term "dative bond", as used herein, is defined as the coordination bond formed upon interaction between molecular species, one of which serves as a donor and the other as an acceptor of the electron pair to be shared in the complex formed.

The term "aliphatic" or "aliphatic group", as used herein, means a straight-chain (i.e., unbranched), branched, or cyclic, substituted or unsubstituted hydrocarbon chain that is completely saturated or that contains one or more units of unsaturation that has a single point of attachment to the rest of the molecule.

Unless otherwise specified, aliphatic groups contain 1-20 aliphatic carbon atoms. In some embodiments, aliphatic groups contain 1-10 aliphatic carbon atoms. In other embodiments, aliphatic groups contain 1-8 aliphatic carbon atoms. In still other embodiments, aliphatic groups contain 1-6 aliphatic carbon atoms, and in yet other embodiments aliphatic groups contain 1-4 aliphatic carbon atoms. Aliphatic groups may be linear or branched, substituted or unsubstituted alkyl, alkenyl, or alkynyl groups. Specific examples include, but are not limited to, methyl, ethyl, isopropyl, n-propyl, sec-butyl, vinyl, n-butenyl, ethynyl, and tert-butyl. Aliphatic groups may also be cyclic, or have a combination of linear or branched and cyclic groups. Examples of such types of aliphatic groups include, but are not limited to cyclopropyl, cyclobutyl, cyclopentyl, cyclohexyl, cyclohexenyl, —CH$_2$-cyclopropyl, CH$_2$CH$_2$CH(CH$_3$)-cyclohexyl.

The term "cycloaliphatic" (or "carbocycle" or "carbocyclyl") refers to a monocyclic C$_3$-C$_8$ hydrocarbon or bicyclic C$_8$-C$_{12}$ hydrocarbon that is completely saturated or that contains one or more units of unsaturation, but which is not aromatic, that has a single point of attachment to the rest of the molecule wherein any individual ring in said bicyclic ring system has 3-7 members. Examples of cycloaliphatic groups include, but are not limited to, cycloalkyl and cycloalkenyl groups. Specific examples include, but are not limited to, cyclohexyl, cyclopropenyl, and cyclobutyl.

The term "heterocycle", "heterocyclyl", or "heterocyclic" as used herein means non-aromatic, monocyclic, bicyclic, or tricyclic ring systems in which one or more ring members are an independently selected heteroatom. In some embodiments, the "heterocycle", "heterocyclyl", or "heterocyclic" group has three to fourteen ring members in which one or more ring members is a heteroatom independently selected from oxygen, sulfur, nitrogen, or phosphorus, and each ring in the system contains 3 to 7 ring members.

Examples of heterocycles include, but are not limited to, 3-1H-benzimidazol-2-one, 3-(1-alkyl)-benzimidazol-2-one, 2-tetrahydrofuranyl, 3-tetrahydrofuranyl, 2-tetrahydrothiophenyl, 3-tetrahydrothiophenyl, 2-morpholino, 3-morpholino, 4-morpholino, 2-thiomorpholino, 3-thiomorpholino, 4-thiomorpholino, 1-pyrrolidinyl, 2-pyrrolidinyl, 3-pyrrolidinyl, 1-tetrahydropiperazinyl, 2-tetrahydropiperazinyl, 3-tetrahydropiperazinyl, 1-piperidinyl, 2-piperidinyl, 3-piperidinyl, 1-pyrazolinyl, 3-pyrazolinyl, 4-pyrazolinyl, 5-pyrazolinyl, 1-piperidinyl, 2-piperidinyl, 3-piperidinyl, 4-piperidinyl, 2-thiazolidinyl, 3-thiazolidinyl, 4-thiazolidinyl, 1-imidazolidinyl, 2-imidazolidinyl, 4-imidazolidinyl, 5-imidazolidinyl, indolinyl, tetrahydroquinolinyl, tetrahydroisoquinolinyl, benzothiolane, benzodithiane, and 1,3-dihydro-imidazol-2-one.

Cyclic groups, (e.g. cycloaliphatic and heterocycles), can be linearly fused, bridged, or spirocyclic.

The term "heteroatom" means one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or NR$^+$ (as in N-substituted pyrrolidinyl)).

The term "unsaturated", as used herein, means that a moiety has one or more units of unsaturation. As would be known by one of skill in the art, unsaturated groups can be partially unsaturated or fully unsaturated. Examples of partially unsaturated groups include, but are not limited to, butene, cyclohexene, and tetrahydropyridine. Fully unsaturated groups can be aromatic, anti-aromatic, or non-aromatic. Examples of fully unsaturated groups include, but are not limited to, phenyl, cyclooctatetraene, pyridyl, thienyl, and 1-methylpyridin-2(1H)-one.

The term "alkoxy", or "thioalkyl", as used herein, refers to an alkyl group, as previously defined, attached through an oxygen ("alkoxy") or sulfur ("thioalkyl") atom.

The terms "haloalkyl", "haloalkenyl", "haloaliphatic", and "haloalkoxy" mean alkyl, alkenyl or alkoxy, as the case may be, substituted with one or more halogen atoms. This term includes perfluorinated alkyl groups, such as —CF$_3$ and —CF$_2$CF$_3$.

The terms "halogen", "halo", and "hal" mean F, Cl, Br, or I.

The term "aryl" used alone or as part of a larger moiety as in "aralkyl", "aralkoxy", or "aryloxyalkyl", refers to monocyclic, bicyclic, and tricyclic ring systems having a total of five to fourteen ring members, wherein at least one ring in the system is aromatic and wherein each ring in the system contains 3 to 7 ring members. The term "aryl" may be used interchangeably with the term "aryl ring".

The term "heteroaryl", used alone or as part of a larger moiety as in "heteroaralkyl" or "heteroarylalkoxy", refers to monocyclic, bicyclic, and tricyclic ring systems having a total of five to fourteen ring members, wherein at least one ring in the system is aromatic, at least one ring in the system contains one or more heteroatoms, and wherein each ring in the system contains 3 to 7 ring members. The term "heteroaryl" may be used interchangeably with the term "heteroaryl ring" or the term "heteroaromatic". Examples of heteroaryl rings include, but are not limited to, 2-furanyl, 3-furanyl, N-imidazolyl, 2-imidazolyl, 4-imidazolyl, 5-imidazolyl, benzimidazolyl, 3-isoxazolyl, 4-isoxazolyl, 5-isoxazolyl, 2-oxazolyl, 4-oxazolyl, 5-oxazolyl, N-pyrrolyl, 2-pyrrolyl, 3-pyrrolyl, 2-pyridyl, 3-pyridyl, 4-pyridyl, 2-pyrimidinyl, 4-pyrimidinyl, 5-pyrimidinyl, pyridazinyl (e.g., 3-pyridazinyl), 2-thiazolyl, 4-thiazolyl, 5-thiazolyl, tetrazolyl (e.g., 5-tetrazolyl), triazolyl (e.g., 2-triazolyl and 5-triazolyl), 2-thienyl, 3-thienyl, benzofuryl, benzothiophenyl, indolyl (e.g., 2-indolyl), pyrazolyl (e.g., 2-pyrazolyl), isothiazolyl, 1,2,3-oxadiazolyl, 1,2,5-oxadiazolyl, 1,2,4-oxadiazolyl, 1,2,3-triazolyl, 1,2,3-thiadiazolyl, 1,3,4-thiadiazolyl, 1,2,5-thiadiazolyl, purinyl, pyrazinyl, 1,3,5-triazinyl, quinolinyl (e.g., 2-quinolinyl, 3-quinolinyl, 4-quinolinyl), and isoquinolinyl (e.g., 1-isoquinolinyl, 3-isoquinolinyl, or 4-isoquinolinyl).

It shall be understood that the term "heteroaryl" includes certain types of heteroaryl rings that exist in equilibrium between two different forms. More specifically, for example, species such hydropyridine and pyridinone (and likewise hydroxypyrimidine and pyrimidinone) are meant to be encompassed within the definition of "heteroaryl."

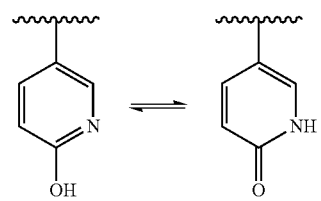 [SMILES: *c1ccc(O)nc1 ; *c1ccc(=O)[nH]c1]

The term "protecting group" and "protective group" as used herein, are interchangeable and refer to an agent used to temporarily block one or more desired functional groups in a compound with multiple reactive sites. In certain embodiments, a protecting group has one or more, or preferably all, of the following characteristics: a) is added selectively to a functional group in good yield to give a protected substrate that is b) stable to reactions occurring at one or more of the other reactive sites; and c) is selectively removable in good yield by reagents that do not attack the regenerated, deprotected functional group. As would be understood by one skilled in the art, in some cases, the reagents do not attack other reactive groups in the compound. In other cases, the reagents may also react with other reactive groups in the compound. Examples of protecting groups are detailed in Greene, T. W., Wuts, P. G in "Protective Groups in Organic Synthesis", Third Edition, John Wiley & Sons, New York: 1999 (and other editions of the book), the entire contents of which are hereby incorporated by reference. The term "nitrogen protecting group", as used herein, refers to an agent used to temporarily block one or more desired nitrogen reactive sites in a multifunctional compound. Preferred nitrogen protecting groups also possess the characteristics exemplified for a protecting group above, and certain exemplary nitrogen protecting groups are also detailed in Chapter 7 in Greene, T. W., Wuts, P. G in "Protective Groups in Organic Synthesis", Third Edition, John Wiley & Sons, New York: 1999, the entire contents of which are hereby incorporated by reference.

In some embodiments, a methylene unit of an alkyl or aliphatic chain is optionally replaced with another atom or group. Examples of such atoms or groups include, but are not limited to, nitrogen, oxygen, sulfur, —C(O)—, —C(=N—CN)—, —C(=NR)—, —C(=NOR)—, —SO—, and —SO₂—. These atoms or groups can be combined to form larger groups. Examples of such larger groups include, but are not limited to, —OC(O)—, —C(O)CO—, —CO₂—, —C(O)NR—, —C(=N—CN), —NRCO—, —NRC(O)O—, —SO₂NR—, —NRSO₂—, —NRC(O)NR—, —OC(O)NR—, and —NRSO₂NR—, wherein R is, for example, H or $C_{1-6}$aliphatic. It should be understood that these groups can be bonded to the methylene units of the aliphatic chain via single, double, or triple bonds. An example of an optional replacement (nitrogen atom in this case) that is bonded to the aliphatic chain via a double bond would be —CH₂CH=N—CH₃. In some cases, especially on the terminal end, an optional replacement can be bonded to the aliphatic group via a triple bond. One example of this would be CH₂CH₂CH₂C≡N. It should be understood that in this situation, the terminal nitrogen is not bonded to another atom.

It should also be understood that, the term "methylene unit" can also refer to branched or substituted methylene units. For example, in an isopropyl moiety [—CH(CH₃)₂], a nitrogen atom (e.g. NR) replacing the first recited "methylene unit" would result in dimethylamine [—N(CH₃)₂]. In instances such as these, one of skill in the art would understand that the nitrogen atom will not have any additional atoms bonded to it, and the "R" from "NR" would be absent in this case.

Unless otherwise indicated, the optional replacements form a chemically stable compound. Optional replacements can occur both within the chain and/or at either end of the chain; i.e. both at the point of attachment and/or also at the terminal end. Two optional replacements can also be adjacent to each other within a chain so long as it results in a chemically stable compound. For example, a $C_3$ aliphatic can be optionally replaced by 2 nitrogen atoms to form —C—N≡N. The optional replacements can also completely replace all of the carbon atoms in a chain. For example, a $C_3$ aliphatic can be optionally replaced by —NR—, —C(O)—, and —NR— to form —NRC(O)NR— (a urea).

Unless otherwise indicated, if the replacement occurs at the terminal end, the replacement atom is bound to a hydrogen atom on the terminal end. For example, if a methylene unit of —CH₂CH₂CH₃ were optionally replaced with —O—, the resulting compound could be —OCH₂CH₃, —CH₂OCH₃, or —CH₂CH₂OH. It should be understood that if the terminal atom does not contain any free valence electrons, then a hydrogen atom is not required at the terminal end (e.g., —CH₂CH₂CH=O or —CH₂CH₂C≡N).

Unless otherwise indicated, structures depicted herein are also meant to include all isomeric (e.g., enantiomeric, diastereomeric, geometric, conformational, and rotational) forms of the structure. For example, the R and S configurations for each asymmetric center, (Z) and (E) double bond isomers, and (Z) and (E) conformational isomers are included in this invention. As would be understood to one skilled in the art, a substituent can freely rotate around any rotatable bonds. For example, a substituent drawn as

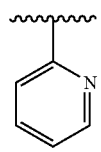

also represents

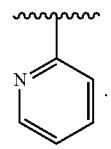

Therefore, single stereochemical isomers as well as enantiomeric, diastereomeric, geometric, conformational, and rotational mixtures of the present compounds are within the scope of the invention.

Unless otherwise indicated, all tautomeric forms of the compounds of the invention are within the scope of the invention.

Additionally, unless otherwise indicated, structures depicted herein are also meant to include compounds that differ only in the presence of one or more isotopically enriched atoms. For example, compounds having the present structures except for the replacement of hydrogen by deuterium or tritium, or the replacement of a carbon by a $^{13}$C- or $^{14}$C-enriched carbon are within the scope of this invention. Such compounds are useful, for example, as analytical tools or probes in biological assays.

Pharmaceutically Acceptable Salts, Solvates, Chlatrates, Prodrugs and Other Derivatives The compounds described herein can exist in free form, or, where appropriate, as salts. Those salts that are pharmaceutically acceptable are of particular interest since they are useful in administering the compounds described below for medical purposes. Salts that are not pharmaceutically acceptable are useful in manufacturing processes, for isolation and purification purposes, and in some instances, for use in separating stereoisomeric forms of the compounds of the invention or intermediates thereof.

As used herein, the term "pharmaceutically acceptable salt" refers to salts of a compound which are, within the scope of sound medical judgment, suitable for use in contact with the tissues of humans and lower animals without undue side effects, such as, toxicity, irritation, allergic response and the like, and are commensurate with a reasonable benefit/risk ratio.

Pharmaceutically acceptable salts are well known in the art. For example, S. M. Berge et al., describe pharmaceutically acceptable salts in detail in J. Pharmaceutical Sciences, 1977, 66, 1-19, incorporated herein by reference. Pharmaceutically acceptable salts of the compounds described herein include those derived from suitable inorganic and organic acids and bases. These salts can be prepared in situ during the final isolation and purification of the compounds.

Where the compound described herein contains a basic group, or a sufficiently basic bioisostere, acid addition salts can be prepared by 1) reacting the purified compound in its free-base form with a suitable organic or inorganic acid and 2) isolating the salt thus formed. In practice, acid addition salts might be a more convenient form for use and use of the salt amounts to use of the free basic form.

Examples of pharmaceutically acceptable, non-toxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, glycolate, gluconate, glycolate, hemisulfate, heptanoate, hexanoate, hydrochloride, hydrobromide, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, palmoate, pectinate, persulfate, 3-phenylpropionate, phosphate, picrate, pivalate, propionate, salicylate, stearate, succinate, sulfate, tartrate, thiocyanate, p-toluenesulfonate, undecanoate, valerate salts, and the like.

Where the compound described herein contains a carboxy group or a sufficiently acidic bioisostere, base addition salts can be prepared by 1) reacting the purified compound in its acid form with a suitable organic or inorganic base and 2) isolating the salt thus formed. In practice, use of the base addition salt might be more convenient and use of the salt form inherently amounts to use of the free acid form. Salts derived from appropriate bases include alkali metal (e.g., sodium, lithium, and potassium), alkaline earth metal (e.g., magnesium and calcium), ammonium and $N^+(C_{1-4}alkyl)_4$ salts. This invention also envisions the quaternization of any basic nitrogen-containing groups of the compounds disclosed herein. Water or oil-soluble or dispersible products may be obtained by such quaternization.

Basic addition salts include pharmaceutically acceptable metal and amine salts. Suitable metal salts include the sodium, potassium, calcium, barium, zinc, magnesium, and aluminum. The sodium and potassium salts are usually preferred. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate and aryl sulfonate. Suitable inorganic base addition salts are prepared from metal bases, which include sodium hydride, sodium hydroxide, potassium hydroxide, calcium hydroxide, aluminium hydroxide, lithium hydroxide, magnesium hydroxide, zinc hydroxide and the like. Suitable amine base addition salts are prepared from amines which are frequently used in medicinal chemistry because of their low toxicity and acceptability for medical use. Ammonia, ethylenediamine, N-methyl-glucamine, lysine, arginine, ornithine, choline, N,N'-dibenzylethylenediamine, chloroprocaine, dietanolamine, procaine, N-benzylphenethylamine, diethylamine, piperazine, tris(hydroxymethyl)-aminomethane, tetramethylammonium hydroxide, triethylamine, dibenzylamine, ephenamine, dehydroabietylamine, N-ethylpiperidine, benzylamine, tetramethylammonium, tetraethylammonium, methylamine, dimethylamine, trimethylamine, ethylamine, basic amino acids, dicyclohexylamine and the like are examples of suitable base addition salts.

Other acids and bases, while not in themselves pharmaceutically acceptable, may be employed in the preparation of salts useful as intermediates in obtaining the compounds described herein and their pharmaceutically acceptable acid or base addition salts.

It should be understood that this invention includes mixtures/combinations of different pharmaceutically acceptable salts and also mixtures/combinations of compounds in free form and pharmaceutically acceptable salts.

The compounds described herein can also exist as pharmaceutically acceptable solvates (e.g., hydrates) and clathrates. As used herein, the term "pharmaceutically acceptable solvate," is a solvate formed from the association of one or more pharmaceutically acceptable solvent molecules to one of the compounds described herein. The term solvate includes hydrates (e.g., hemihydrate, monohydrate, dihydrate, trihydrate, tetrahydrate, and the like).

As used herein, the term "hydrate" means a compound described herein or a salt thereof that further includes a stoichiometric or non-stoichiometric amount of water bound by non-covalent intermolecular forces.

As used herein, the term "clathrate" means a compound described herein or a salt thereof in the form of a crystal lattice that contains spaces (e.g., channels) that have a guest molecule (e.g., a solvent or water) trapped within.

In addition to the compounds described herein, pharmaceutically acceptable derivatives or prodrugs of these compounds may also be employed in compositions to treat or prevent the herein identified disorders.

A "pharmaceutically acceptable derivative or prodrug" includes any pharmaceutically acceptable ester, salt of an ester, or other derivative or salt thereof of a compound described herein which, upon administration to a recipient, is capable of providing, either directly or indirectly, a compound described herein or an inhibitorily active metabolite or residue thereof. Particularly favoured derivatives or prodrugs are those that increase the bioavailability of the compounds when such compounds are administered to a patient (e.g., by allowing an orally administered compound to be more readily absorbed into the blood) or which enhance delivery of the parent compound to a biological compartment (e.g., the brain or lymphatic system) relative to the parent species.

As used herein and unless otherwise indicated, the term "prodrug" means a derivative of a compound that can hydrolyze, oxidize, or otherwise react under biological conditions (in vitro or in vivo) to provide a compound described herein. Prodrugs may become active upon such reaction under biological conditions, or they may have activity in their unreacted forms. Examples of prodrugs contemplated in this invention include, but are not limited to, analogs or derivatives of compounds of the invention that comprise biohydrolyzable moieties such as biohydrolyzable amides, biohydrolyzable esters, biohydrolyzable carbamates, biohydrolyzable carbonates, biohydrolyzable ureides, and biohydrolyzable phosphate analogues. Other examples of prodrugs include derivatives of compounds described herein that comprise —NO, —NO$_2$, —ONO, or —ONO$_2$ moieties. Prodrugs can typically be prepared using well-known methods, such as those described by BURGER'S MEDICINAL CHEMISTRY AND DRUG DISCOVERY (1995) 172-178, 949-982 (Manfred E. Wolff ed., 5th ed).

Therapeutic Uses

One aspect of this invention provides a combination therapy that inhibits the ATR pathway comprising a compound useful for inhibiting ATR kinase, as well as a compound useful for inhibiting Chk1 kinase (a.k.a. "ATR/Chk1 combination therapy"). In some embodiments, the compound useful for inhibiting ATR is selected from the group consisting of a compound of formula I or a compound of formula II. The combination therapy is useful for treating or lessening the severity of a disease, condition, or disorder where the ATR pathway is implicated in the disease, condition, or disorder.

Another aspect of this invention provides a combination therapy useful for the treatment of diseases, disorders, and conditions characterized by excessive or abnormal cell proliferation, including proliferative or hyperproliferative diseases. Examples of proliferative and hyperproliferative diseases include, but are not limited to, cancer and myeloproliferative disorders.

The term "cancer" includes, but is not limited to the following types of cancers: oral, lung, gastrointestinal, genitourinary tract, liver, bone, nervous system, gynecological, skin, thyroid gland, or adrenal gland. More specifically, "cancer" includes, but is not limited to the following cancers: Oral: buccal cavity, lip, tongue, mouth, pharynx; Cardiac: sarcoma (angiosarcoma, fibrosarcoma, rhabdomyosarcoma, liposarcoma), myxoma, rhabdomyoma, fibroma, lipoma and teratoma; Lung: bronchogenic carcinoma (squamous cell or epidermoid, undifferentiated small cell, undifferentiated large cell, adenocarcinoma), alveolar (bronchiolar) carcinoma, bronchial adenoma, sarcoma, lymphoma, chondromatous hamartoma, mesothelioma; Gastrointestinal: esophagus (squamous cell carcinoma, larynx, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel or small intestines (adenocarcinoma, lymphoma, carcinoid tumors, Karposi's sarcoma, leiomyoma, hemangioma, lipoma, neurofibroma, fibroma), large bowel or large intestines (adenocarcinoma, tubular adenoma, villous adenoma, hamartoma, leiomyoma), colon, colon-rectum, colorectal; rectum, Genitourinary tract: kidney (adenocarcinoma, Wilm's tumor [nephroblastoma], lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastoma, angiosarcoma, hepatocellular adenoma, hemangioma, biliary passages; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma [pinealoma], glioblastoma multiform, oligodendroglioma, schwannoma, retinoblastoma, congenital tumors), spinal cord neurofibroma, meningioma, glioma, sarcoma); Gynecological: uterus (endometrial carcinoma), cervix (cervical carcinoma, pre-tumor cervical dysplasia), ovaries (ovarian carcinoma [serous cystadenocarcinoma, mucinous cystadenocarcinoma, unclassified carcinoma], granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), fallopian tubes (carcinoma), breast; Hematologic: blood (myeloid leukemia [acute and chronic], acute lymphoblastic leukemia, chronic lymphocytic leukemia, myeloproliferative diseases, multiple myeloma, myelodysplastic syndrome), Hodgkin's disease, non-Hodgkin's lymphoma [malignant lymphoma] hairy cell; lymphoid disorders; Skin: malignant melanoma, basal cell carcinoma, squamous cell carcinoma, Karposi's sarcoma, keratoacanthoma, moles dysplastic nevi, lipoma, angioma, dermatofibroma, keloids, psoriasis, Thyroid gland: papillary thyroid carcinoma, follicular thyroid carcinoma, undifferentiated thyroid cancer, medullary thyroid carcinoma, multiple endocrine neoplasia type 2A, multiple endocrine neoplasia type 2B, familial medullary thyroid cancer, pheochromocytoma, paraganglioma; and Adrenal glands: neuroblastoma.

In other embodiments, the cancer is selected from lung cancer, head and neck cancer, pancreatic cancer, breast cancer, gastric cancer, or brain cancer. In yet other embodiments, the cancer is selected from non-small cell lung cancer, small cell lung cancer, pancreatic cancer, biliary tract cancer, head and neck cancer, bladder cancer, colorectal cancer, glioblastoma, esophageal cancer, breast cancer, hepatocellular carcinoma, or ovarian cancer. In some embodiments, the cancer is selected from a cancer of the lung or the breast. In still other embodiments the cancer is selected from non-small cell lung cancer, small cell lung cancer, and triple negative breast cancer.

The term "cancer cell" as provided herein, includes a cell afflicted by any one of the above-identified conditions. In some embodiments, the cancer is selected from colorectal, thyroid, lung, or breast cancer.

The term "myeloproliferative disorders", includes disorders such as polycythemia vera, thrombocythemia, myeloid metaplasia with myelofibrosis, hypereosinophilic syndrome, juvenile myelomonocytic leukemia, systemic mast cell disease, and hematopoietic disorders, in particular, acute-myelogenous leukemia (AML), chronic-myelogenous leukemia (CML), acute-promyelocytic leukemia (APL), and acute lymphocytic leukemia (ALL).

Pharmaceutical Compositions

The present invention also provides a combination therapy comprising a compound or composition useful for inhibiting ATR kinase and a compound or composition useful for inhibiting Chk1 kinase.

One aspect of this invention provides a combination therapy comprising a composition useful for inhibiting ATR kinase and a composition useful for inhibiting Chk1 kinase, as described herein. Each composition optionally comprises a pharmaceutically acceptable carrier, adjuvant or vehicle.

The pharmaceutically acceptable carrier, adjuvant, or vehicle, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical Sciences, Sixteenth Edition, E. W. Martin (Mack Publishing Co., Easton, Pa., 1980) discloses various carriers used in formulating pharmaceutically acceptable compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutically acceptable composition, its use is contemplated to be within the scope of this invention.

Some examples of materials which can serve as pharmaceutically acceptable carriers include, but are not limited to, ion exchangers, alumina, aluminum stearate, lecithin, serum proteins, such as human serum albumin, buffer substances such as phosphates, glycine, sorbic acid, or potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, polyacrylates, waxes, polyethylene-polyoxypropylene-block polymers, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol or polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

The ATR and Chk1 kinase inhibitors or pharmaceutical salts thereof may be formulated into pharmaceutical compositions for administration to animals or humans. These pharmaceutical compositions, which comprise a sufficient amount of the ATR and Chk1 inhibitor effective to treat or prevent the diseases or conditions described herein and a pharmaceutically acceptable carrier, are described above.

The exact amount of compound required for treatment will vary from patient to patient, depending on the species, age, and general condition of the patient, the severity of the infection, the particular agent, its mode of administration, and the like. The compounds of the invention are preferably formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of the present invention will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts. The term "patient", as used herein, means an animal, preferably a mammal, and most preferably a human.

In some embodiments, these compositions optionally further comprise one or more additional therapeutic agents. For example, chemotherapeutic agents or other anti-proliferative agents may be combined with the compounds of this invention to treat proliferative diseases and cancer. Examples of known agents with which these compositions can be combined are listed above under the "Additional Therapeutic Agents" section, below, and also throughout the specification. Some embodiments provide a simultaneous, separate or sequential use of a combined preparation.

Additional Therapeutic Agents

Another aspect of this invention is directed towards a method of treating cancer in a patient in need thereof, comprising administration of a compound useful for inhibiting ATR kinase; administration of a compound useful for inhibiting Chk1 kinase, and administration of a one or more additional therapeutic agents. In some embodiments, said method comprises the sequential or co-administration of the compounds or compositions of the ATR/Chk1 combination therapy, and the additional therapeutic agent.

As used herein, the term "in combination" or "co-administration" can be used interchangeably to refer to the use of more than one therapy (e.g., one or more therapeutic agents). The use of the term does not restrict the order in which therapies (e.g., therapeutic agents) are administered to a patient.

In some embodiments, said additional therapeutic agent is an anti-cancer agent. In other embodiments, said additional therapeutic agent is a DNA-damaging agent. It shall be understood that the additional therapeutic agent may comprise one or more therapies. In yet other embodiments, said additional therapeutic agent is selected from radiation therapy, chemotherapy, or other agents typically used in combination with radiation therapy or chemotherapy, such as radiosensitizers and chemosensitizers. In yet other embodiments, said additional therapeutic agent is ionizing radiation. In some embodiments, said additional therapeutic agent comprises ionizing radiation and a DNA-damaging agent.

As would be known by one of skill in the art, radiosensitizers are agents that can be used in combination with radiation therapy. Radiosensitizers work in various different ways, including, but not limited to, making cancer cells more sensitive to radiation therapy, working in synergy with radiation therapy to provide an improved synergistic effect, acting additively with radiation therapy, or protecting surrounding healthy cells from damage caused by radiation therapy. Likewise chemosensitizers are agents that can be used in combination with chemotherapy. Similarly, chemosensitizers work in various different ways, including, but not limited to, making cancer cells more sensitive to chemotherapy, working in synergy with chemotherapy to provide an improved synergistic effect, acting additively to chemotherapy, or protecting surrounding healthy cells from damage caused by chemotherapy.

Examples of DNA-damaging agents that may be used with the ATR/Chk1 combination therapy of this invention include, but are not limited to Platinating agents, such as Carboplatin, Oxaliplatin, Cisplatin, Nedaplatin, Satraplatin, Lobaplatin, Triplatin, Tetranitrate, Picoplatin, Prolindac, Aroplatin and other derivatives; Topo I inhibitors, such as Camptothecin, Topotecan, irinotecan/SN38, rubitecan, Belotecan, and other derivatives; Topo II inhibitors, such as Etoposide (VP-16), Daunorubicin, Doxorubicin, Mitoxantrone, Aclarubicin, Epirubicin, Idarubicin, Amrubicin, Amsacrine, Pirarubicin, Valrubicin, Zorubicin, Teniposide and other derivatives; Antimetabolites, such as Folic family (Methotrexate, Pemetrexed, Raltitrexed, Aminopterin, and relatives); Purine antagonists (Thioguanine, Fludarabine, Cladribine, 6-Mercaptopurine, Pentostatin, clofarabine and relatives) and Pyrimidine antagonists (Cytarabine, Floxuridine, Azacitidine, Tegafur, Carmofur, Capacitabine, Gemcitabine, hydroxyurea, 5-Fluorouracil (5FU), and relatives); Alkylating agents, such as Nitrogen mustards (e.g., Cyclophosphamide, Melphalan, Chlorambucil, mechlorethamine, Ifosfamide, mechlorethamine, Trofosfamide, Prednimustine, Bendamustine, Uramustine, Estramustine, and relatives); nitrosoureas (e.g., Carmustine, Lomustine, Semustine, Fotemustine, Nimustine, Ranimustine, Streptozocin, and relatives); Triazenes (e.g., Dacarbazine, Altretamine, Temozolomide, and relatives); Alkyl sulphonates (e.g., Busulfan, Mannosulfan, Treosulfan, and relatives); Procarbazine; Mitobronitol, and Aziridines (e.g., Carboquone, Triaziquone, ThioTEPA, triethylenemalamine, and relatives); Antibiotics, such as Hydroxyurea, Anthracyclines (e.g., doxorubicin, daunorubicin, epirubicin and other derivatives); Anthracenediones (e.g, Mitoxantrone and relatives); Streptomyces family (e.g., Bleomycin, Mitomycin C, Actinomycin, Plicamycin); and Ultraviolet light.

Other therapies or anticancer agents that may be used in the combination therapy include surgery, radiotherapy (in but a few examples, gamma-radiation, neutron beam radiotherapy, electron beam radiotherapy, proton therapy, brachytherapy, and systemic radioactive isotopes, to name a few), endocrine therapy, biologic response modifiers (interferons, interleukins, and tumor necrosis factor (TNF) to name a few), hyperthermia and cryotherapy, agents to attenuate any adverse effects (e.g., antiemetics), and other approved chemotherapeutic drugs, including, but not limited to, the DNA damaging agents listed herein, spindle poisons (Vinblastine, Vincristine, Vinorelbine, Paclitaxel), podophyllotoxins (Etoposide, Irinotecan, Topotecan), nitrosoureas (Carmustine, Lomustine), inorganic ions (Cisplatin, Carboplatin), enzymes (Asparaginase), and hormones (Tamoxifen, Leuprolide, Flutamide, and Megestrol), Gleevec™, adriamycin, dexamethasone, and cyclophosphamide.

Other combination therapies of the instant invention may utilize any of the following therapeutic agents: abarelix (Plenaxis Depot®); aldesleukin (Prokine®); Aldesleukin (Proleukin®); Alemtuzumabb (Campath®); alitretinoin (Panretin®); allopurinol (Zyloprim®); altretamine (Hexalen®); amifostine (Ethyol®); anastrozole (Arimidex®); arsenic trioxide (Trisenox®); asparaginase (Elspar®); azacitidine (Vidaza®); bevacuzimab (Avastin®); bexarotene capsules (Targretin®); bexarotene gel (Targretin®); bleomycin (Blenoxane®); bortezomib (Velcade®); busulfan intravenous (Busulfex®); busulfan oral (Myleran®); calusterone (Methosarb®); capecitabine (Xeloda®); carboplatin (Paraplatin®); carmustine (BCNU®, BiCNU®); carmustine (Gliadel®); carmustine with Polifeprosan 20 Implant (Gliadel Wafer®); celecoxib (Celebrex®); cetuximab (Erbitux®); chlorambucil (Leukeran®); cisplatin (Platinol®); cladribine (Leustatin®, 2-CdA®); clofarabine (Clolar®); cyclophosphamide (Cytoxan®, Neosar®); cyclophosphamide (Cytoxan Injection®); cyclophosphamide (Cytoxan Tablet®); cytarabine (Cytosar-U®); cytarabine liposomal (DepoCyt®); dacarbazine (DTIC-Dome®); dactinomycin, actinomycin D (Cosmegen®); Darbepoetin alfa (Aranesp®); daunorubicin liposomal (DanuoXome®); daunorubicin, daunomycin (Daunorubicin®); daunorubicin, daunomycin (Cerubidine®); Denileukin diftitox (Ontak®); dexrazoxane (Zinecard®); docetaxel (Taxotere®); doxorubicin (Adriamycin PFS®); doxorubicin (Adriamycin®, Rubex®); doxorubicin (Adriamycin PFS Injection®); doxorubicin liposomal (Doxil®); dromostanolone propionate (Dromostanolone®); dromostanolone propionate (masterone Injection®); Elliott's B Solution (Elliott's B Solution®); epirubicin (Ellence®); Epoetin alfa (Epogen®); erlotinib (Tarceva®); estramustine (Emcyt®); etoposide phosphate (Etopophos®); etoposide, VP-16 (Vepesid®); exemestane (Aromasin®); Filgrastim (Neupogen®); floxuridine (intraarterial) (FUDR®); fludarabine (Fludara®); fluorouracil, 5-FU (Adrucil®); fulvestrant (Faslodex®); gefitinib (Iressa®); gemcitabine (Gemzar®); gemtuzumab ozogamicin (Mylotarg®); goserelin acetate (Zoladex Implant®); goserelin acetate (Zoladex®); histrelin acetate (Histrelin Implant®); hydroxyurea (Hydrea®); Ibritumomab Tiuxetan (Zevalin®); idarubicin (Idamycin®); ifosfamide (IFEX®); imatinib mesylate (Gleevec®); interferon alfa 2a (Roferon A®); Interferon alfa-2b (Intron A®); irinotecan (Camptosar®); lenalidomide (Revlimid®); letrozole (Femara®); leucovorin (Wellcovorin®, Leucovorin®); Leuprolide Acetate (Eligard®); levamisole (Ergamisol®); lomustine, CCNU (CeeBU®); meclorethamine, nitrogen mustard (Mustargen®); megestrol acetate (Megace®); melphalan, L-PAM (Alkeran®); mercaptopurine, 6-MP (Purinethol®); mesna (Mesnex®); mesna (Mesnex Tabs®); methotrexate (Methotrexate®); methoxsalen (Uvadex®); mitomycin C (Mutamycin®); mitotane (Lysodren®); mitoxantrone (Novantrone®); nandrolone phenpropionate (Durabolin-50®); nelarabine (Arranon®); Nofetumomab (Verluma®); Oprelvekin (Neumega®); oxaliplatin (Eloxatin®); paclitaxel (Paxene®); paclitaxel (Taxol®); paclitaxel protein-bound particles (Abraxane®); palifermin (Kepivance®); pamidronate (Aredia®); pegademase (Adagen (Pegademase Bovine)®); pegaspargase (Oncaspar®); Pegfilgrastim (Neulasta®); pemetrexed disodium (Alimta®); pentostatin (Nipent®); pipobroman (Vercyte®); plicamycin, mithramycin (Mithracin®); porfimer sodium (Photofrin®); procarbazine (Matulane®); quinacrine (Atabrine®); Rasburicase (Elitek®); Rituximab (Rituxan®); sargramostim (Leukine®); Sargramostim (Prokine®); sorafenib (Nexavar®); streptozocin (Zanosar®); sunitinib maleate (Sutent®); talc (Sclerosol®); tamoxifen (Nolvadex®); temozolomide (Temodar®); teniposide, VM-26 (Vumon®); testolactone (Teslac®); thioguanine, 6-TG (Thioguanine®); thiotepa (Thioplex®); topotecan (Hycamtin®); toremifene (Fareston®); Tositumomab (Bexxar®); Tositumomab/I-131 tositumomab (Bexxar®); Trastuzumab (Herceptin®); tretinoin, ATRA (Vesanoid®); Uracil Mustard (Uracil Mustard Capsules®); valrubicin (Valstar®); vinblastine (Velban®); vincristine (Oncovin®); vinorelbine (Navelbine®); zoledronate (Zometa®) and vorinostat (Zolinza®).

For a comprehensive discussion of updated cancer therapies see The Merck Manual, Seventeenth Ed. 1999, the entire contents of which are hereby incorporated by reference.

In another embodiment, the additional therapeutic agent may be a compound or composition that inhibits or modulates a base excision repair protein. In some embodiments, the base excision repair protein is selected from UNG, SMUG1, MBD4, TDG, OGG1, MYH, NTH1, MPG, NEIL1, NEIL2, NEIL3 (DNA glycosylases); APE1, APEX2 (AP endonucleases); LIG1, LIG3 (DNA ligases I and III); XRCC1 (LIG3 accessory); PNK, PNKP (polynucleotide kinase and phosphatase); PARP1, PARP2 (Poly(ADP-Ribose) Polymerases); PolB, PolG (polymerases); FEN1 (endonuclease) or Aprataxin. In other embodiments, the base excision repair protein is selected from PARP1, PARP2, or PolB. In yet other embodiments, the base excision repair protein is selected from PARP1 or PARP2. In other embodiments, the agent that inhibits or modulates PARP1 or PARP2 is selected from Olaparib (also known as AZD2281 or KU-0059436), Iniparib (also known as BSI-201 or SAR240550), Veliparib (also known as ABT-888), Rucaparib (also known as PF-01367338), CEP-9722, INO-1001, MK-4827, E7016, BMN673, or AZD2461.

Another embodiment provides a method of treating cancer comprising administering a compound useful for inhibiting Chk1 kinase; administering a compound useful for inhibiting ATR kinase; administering a compound useful for inhibiting or modulating PARP1 or PARP2; and administering a DNA damaging agent. In another embodiment, the DNA damaging agent is selected from ionizing radiation or cisplatin. In some embodiments the DNA-damaging agent is cisplatin. In other embodiments, the DNA damaging agent is ionizing radiation. In some embodiments, the agent that inhibits or modulates PARP1 or PARP2 is selected from Olaparib (also known as AZD2281 or KU-0059436), Iniparib (also known as BSI-201 or SAR240550), Veliparib (also known as ABT-888), Rucaparib (also known as PF-01367338), CEP-9722, INO-1001, MK-4827, E7016, BMN673, or AZD2461. In other embodiments, the agent that inhibits or modulates PARP1 or PARP2 is Veliparib (also known as ABT-888) or Rucaparib.

Modes of Administration and Dosage Forms

The pharmaceutically acceptable compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated. In certain embodiments, the compounds of the invention may be administered orally or parenterally at dosage levels of about 0.01 mg/kg to about 50 mg/kg and preferably from about 1 mg/kg to about 25 mg/kg, of patient body weight per dose to obtain the desired therapeutic effect.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polyethylene glycols and the like.

The active compounds can also be in microencapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, eardrops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

The compositions of the present invention may be administered orally, parenterally, by inhalation spray, topically, rectally, nasally, buccally, vaginally or via an implanted reservoir. The term "parenteral" as used herein includes, but is not limited to, subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously.

Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents which are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

The pharmaceutical compositions of this invention may be orally administered in any orally acceptable dosage form including, but not limited to, capsules, tablets, aqueous suspensions or solutions. In the case of tablets for oral use, carriers commonly used include, but are not limited to, lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, the pharmaceutical compositions of this invention may be administered in the form of suppositories for rectal administration. These can be prepared by mixing the agent with a suitable non-irritating excipient that is solid at room temperature but liquid at rectal temperature and therefore will melt in the rectum to release the drug. Such materials include, but are not limited to, cocoa butter, beeswax and polyethylene glycols.

The pharmaceutical compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, the pharmaceutical compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutical compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutical compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutical compositions may be formulated in an ointment such as petrolatum.

The pharmaceutical compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

The amount of protein kinase inhibitor that may be combined with the carrier materials to produce a single dosage form will vary depending upon the host treated, the particular mode of administration. Preferably, the compositions should be formulated so that a dosage of between 0.01-100 mg/kg body weight/dose of the inhibitor can be administered to a patient receiving these compositions.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated.

The amount of inhibitor will also depend upon the particular compound in the composition.

Biological Samples

As inhibitors of the ATR pathway, the compounds and compositions of this invention are also useful in biological samples. One aspect of the invention relates to inhibiting ATR and Chk1 kinase activity in a biological sample, which method comprises contacting said biological sample with a compound that inhibits ATR kinase activity and a compound that inhibits Chk1 kinase activity. Alternatively, separate compositions comprising these compounds may be utilized. The term "biological sample", as used herein, means an in vitro or an ex vivo sample, including, without limitation, cell cultures or extracts thereof; biopsied material obtained from a mammal or extracts thereof; and blood, saliva, urine, feces, semen, tears, or other body fluids or extracts thereof. The term "compounds" includes compounds of formula I and formula II.

Inhibition of ATR and Chk1 kinase activity in a biological sample is useful for a variety of purposes that are known to one of skill in the art. Examples of such purposes include, but are not limited to, blood transfusion, organ-transplantation, and biological specimen storage.

Study of Protein Kinases

Another aspect of this invention relates to the study of protein kinases in biological and pathological phenomena; the study of intracellular signal transduction pathways mediated by such protein kinases; and the comparative evaluation of new protein kinase inhibitors. Examples of such uses include, but are not limited to, biological assays such as enzyme assays and cell-based assays.

The activity of the compounds as protein kinase inhibitors may be assayed in vitro, in vivo or in a cell line. In vitro assays include assays that determine inhibition of either the kinase activity or ATPase activity of the activated kinase. Alternate in vitro assays quantitate the ability of the inhibitor to bind to the protein kinase and may be measured either by radiolabelling the inhibitor prior to binding, isolating the inhibitor/kinase complex and determining the amount of radiolabel bound, or by running a competition experiment where new inhibitors are incubated with the kinase bound to known radioligands. Detailed conditions for assaying a compound utilized in this invention as an inhibitor of ATR is set forth in the Examples below.

Methods of Treatment

In one aspect, the present invention provides a method for treating cancer in a patient comprising administering a compound that inhibits ATR protein kinase; and administering a compound that inhibits Chk1 protein kinase ("ATR/Chk1 combination therapy").

In another aspect, the present invention provides a method for treating cancer in a patient comprising administering a compound that inhibits ATR protein kinase; administering a compound that inhibits Chk 1 protein kinase; and administering one or more additional therapeutic agent independently selected from a DNA-damaging agent, wherein the additional therapeutic agent is appropriate for the disease being treated; and the additional therapeutic agent is administered together with the compounds as a single dosage form or separately from the compounds as part of a multiple dosage form.

In some embodiments, the DNA-damaging agent is independently selected from chemotherapy or radiation treatment In another embodiment, the DNA-damaging agent is selected from ionizing radiation, radiomimetic neocarzinostatin, a platinating agent, a Topo I inhibitor, a Topo II inhibitor, an antimetabolite, an alkylating agent, an alkyl sulphonates, an antimetabolite, or an antibiotic. In other embodiments, said DNA-damaging agent is selected from ionizing radiation, a platinating agent, a Topo I inhibitor, a Topo II inhibitor, an antimetabolite, an alkylating agent, or an alkyl sulphonate.

In yet another embodiment, said platinating agent is independently selected from Cisplatin, Oxaliplatin, Carboplatin, Nedaplatin, Lobaplatin, Triplatin Tetranitrate, Picoplatin, Satraplatin, ProLindac and Aroplatin; said Topo I inhibitor is selected from Camptothecin, Topotecan, Irinotecan/SN38, Rubitecan and Belotecan; said Topo II inhibitor is selected from Etoposide, Daunorubicin, Doxorubicin, Aclarubicin, Epirubicin, Idarubicin, Amrubicin, Pirarubicin, Valrubicin, Zorubicin and Teniposide; said antimetabolite is selected from Aminopterin, Methotrexate, Pemetrexed, Raltitrexed, Pentostatin, Cladribine, Clofarabine, Fludarabine, Thioguanine, Mercaptopurine, Fluorouracil, Capecitabine, Tegafur, Carmofur, Floxuridine, Cytarabine, Gemcitabine, Azacitidine and Hydroxyurea; said alkylating agent is selected from Mechlorethamine, Cyclophosphamide, Ifosfamide, Trofosfamide, Chlorambucil, Melphalan, Prednimustine, Bendamustine, Uramustine, Estramustine, Carmustine, Lomustine, Semustine, Fotemustine, Nimustine, Ranimustine, Streptozocin, Busulfan, Mannosulfan, Treosulfan, Carboquone, ThioTEPA, Triaziquone, Triethylenemelamine, Procarbazine, Dacarbazine, Temozolomide, Altretamine, Mitobronitol, Actinomycin, Bleomycin, Mitomycin and Plicamycin.

In still other embodiments, said platinating agent is independently selected from Cisplatin, Oxaliplatin, Carboplatin, Nedaplatin, or Satraplatin; said Topo I inhibitor is selected from Camptothecin, Topotecan, irinotecan/SN38, rubitecan; said Topo II inhibitor is selected from Etoposide; said antimetabolite is selected from methotrexate, pemetrexed, Thioguanine, Fludarabine, Cladribine, Cytarabine, gemcitabine, 6-Mercaptopurine, or 5-Fluorouracil; said alkylating agent is selected from nitrogen mustards, nitrosoureas, triazenes, alkyl sulfonates, Procarbazine, or aziridines; and said antibiotic is selected from Hydroxyurea, Anthracyclines, Anthracenediones, or Streptomyces family.

In some embodiments, the DNA-damaging agent is a platinating agent. In other embodiments, the DNA-damaging agent is a platinating agent selected from Cisplatin. In still other embodiments, the DNA-damaging agent is a platinating agent selected from Carboplatin.

In yet another embodiment, the DNA-damaging agent is ionizing radiation.

In still other embodiments, the DNA-damaging agent is an antimetabolite selected from gemcitabine.

In some embodiments, the DNA-damaging agent is a Topo I inhibitor selected from Camptothecin, Topotecan, Irinotecan/SN38, Rubitecan or Belotecan.

In other embodiments, the DNA-damaging agent is a Topo II inhibitor selected from Etoposide.

In still other embodiments, the DNA-damaging agent is an alkylating agent selected from Temozolomide.

In yet other embodiments, the DNA-damaging agent is selected from one or more of the following: Cisplatin, Carboplatin, Gemcitabine, Etoposide, Temozolomide, or ionizing radiation. In other embodiments, the additional therapeutic agent is Cisplatin or Carboplatin.

In some embodiments, the ATR/Chk1 combination therapy is combined with chemoradiation, chemotherapy, and/or radiation therapy. As would be understood by one of skill in the art, chemoradiation refers to a treatment regime that includes both chemotherapy (such as cisplatin) and radiation. In some embodiments, the chemotherapy is cisplatin.

In one or more embodiments, the cancer is a solid tumor selected from the following cancers: oral, lung, gastrointestinal: genitourinary tract, liver, bone, nervous system, gynecological, skin, thyroid gland, or adrenal gland.

In some embodiments, the cancer is a solid tumor selected from the following cancers: Oral: buccal cavity, lip, tongue, mouth, pharynx; Cardiac: sarcoma (angiosarcoma, fibrosarcoma, rhabdomyosarcoma, liposarcoma), myxoma, rhabdomyoma, fibroma, lipoma and teratoma; Lung: bronchogenic carcinoma (squamous cell or epidermoid, undifferentiated small cell, undifferentiated large cell, adenocarcinoma), alveolar (bronchiolar) carcinoma, bronchial adenoma, sarcoma, lymphoma, chondromatous hamartoma, mesothelioma; Gastrointestinal: esophagus (squamous cell carcinoma, larynx, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel or small intestines (adenocarcinoma, lymphoma, carcinoid tumors, Karposi's sarcoma, leiomyoma, hemangioma, lipoma, neurofibroma, fibroma), large bowel or large intestines (adenocarcinoma, tubular adenoma, villous adenoma, hamartoma, leiomyoma), colon, colon-rectum, colorectal; rectum, Genitourinary tract: kidney (adenocarcinoma, Wilm's tumor [nephroblastoma], lymphoma), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastoma, angiosarcoma, hepatocellular adenoma, hemangioma, biliary passages; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma [pinealoma], glioblastoma multiform, oligodendroglioma, schwannoma, retinoblastoma, congenital tumors), spinal cord neurofibroma, meningioma, glioma, sarcoma); Gynecological: uterus (endometrial carcinoma), cervix (cervical carcinoma, pre-tumor cervical dysplasia), ovaries (ovarian carcinoma [serous cystadenocarcinoma, mucinous cystadenocarcinoma, unclassified carcinoma], granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), fallopian tubes (carcinoma), breast; Skin: malignant melanoma, basal cell carcinoma, squamous cell carcinoma, Karposi's sarcoma, keratoacanthoma, moles dysplastic nevi, lipoma, angioma, dermatofibroma, keloids, psoriasis, Thyroid gland: papillary thyroid carcinoma, follicular thyroid carcinoma; medullary thyroid carcinoma, multiple endocrine neoplasia type 2A, multiple endocrine neoplasia type 2B, familial medullary thyroid cancer, pheochromocytoma, paraganglioma; and Adrenal glands: neuroblastoma.

In another embodiment, the cancer is selected from non-small cell lung cancer, small cell lung cancer, pancreatic cancer, biliary tract cancer, head and neck cancer, bladder cancer, colorectal cancer, glioblastoma, esophageal cancer, breast cancer, hepatocellular carcinoma, or ovarian cancer. In other embodiments, the cancer is selected from non-small cell lung cancer, small cell lung cancer, and triple negative breast cancer. In some embodiments, the cancer is selected from non-small cell lung cancer, small cell lung cancer, serous ovarian cancer, and triple negative breast cancer.

Another embodiment provides a method of treating breast cancer using the ATR/Chk1 combination therapy described herein in combination with a platinating agent. In some embodiments, the breast cancer is triple negative breast cancer. In other embodiments, the platinating agent is cisplatin.

Another embodiment provides a method of treating non-small cell lung cancer using the ATR/Chk1 combination therapy described herein in combination with cisplatin and gemcitabine. In some embodiments, the non-small cell lung cancer is squamous non-small cell lung cancer. In some embodiments, the compound is a compound of Formula I. In other embodiments, the compound is VE-822.

In yet another embodiment, the additional therapeutic agent is gemcitabine or cisplatin and the cancer is the squamous subtype of non-small cell lung cancer. Another embodiment provides a method of treating small cell lung cancer using the ATR/Chk1 combination therapy described herein in combination with cisplatin and etoposide.

Another aspect of the present invention provides a method of promoting cell death in cancer cells comprising administering a compound that inhibits ATR protein kinase; and administering a compound that inhibits Chk1 protein kinase. In some embodiments, the cancer cells have defects in the ATM signaling cascade. In another embodiment, the defect is altered expression or activity of one or more of the following: ATM, p53, CHK2, MRE11, RAD50, NBS1, 53BP1, MDC1, H2AX, MCPH1/BRIT1, CTIP, or SMC1. In still other aspects, the defect is altered expression or activity of one or more of the following: ATM, p53, CHK2, MRE11, RAD50, NBS1, 53BP1, MDC1 or H2AX.

In some embodiments, the cancer cell is expressing DNA damaging oncogenes.

In other embodiments, the cancer cell has altered expression or activity of one or more of the following: K-Ras, N-Ras, H-Ras, Raf, Myc, Mos, E2F, Cdc25A, CDC4, CDK2, Cyclin E, Cyclin A and Rb.

In another aspect, this invention provides a method for treating or lessening the severity of a disease, condition, or disorder with a combination therapy that inhibits enzymatic activity by binding a compound to ATR kinase and binding a separate compound to Chk1 kinase.

Another aspect of this invention provides a method for treating, preventing, or lessening the severity of proliferative or hyperproliferative diseases in a patient comprising administering an effective amount of a first compound useful for inhibiting ATR kinase, or a pharmaceutically acceptable composition comprising the first compound; and administering an effective amount of a second compound useful for inhibiting Chk1 kinase, or a pharmaceutically acceptable composition comprising the second compound. The term "patient", as used herein, means an animal, preferably a human.

In certain embodiments, an "effective amount" of the compound or pharmaceutically acceptable composition is that amount effective in order to treat said disease. The compounds and compositions, according to the method of the present invention, may be administered using any amount and any route of administration effective for treating or lessening the severity of said disease.

In some embodiments, the compound useful for inhibiting ATR kinase is a compound of Formula I. In other embodiments, the compound useful for inhibiting ATR kinase is VE-821. In other embodiments, the compound useful for inhibiting ATR kinase is VE-822.

Yet another embodiment provides a method of preventing cell repair of DNA damage in cancer cells comprising administering to a patient a first compound useful as an inhibitor of ATR kinase, or a composition comprising the first compound; and administering to a patient a second compound useful as an inhibitor of Chk1 kinase, or a composition comprising the second compound.

Another embodiment provides a method of sensitizing cells to DNA damaging agents comprising administering to a patient a first compound useful as an inhibitor of ATR kinase, or a composition comprising the first compound; and administering to a patient a second compound useful as an inhibitor of Chk1 kinase, or a composition comprising the second compound.

According to another embodiment, the ATR/Chk1 combination therapy is used on a cancer, cancer cell, or cell that has a defect in a protein involved in base excision repair ("base excision repair protein"). There are many methods known in the art for determining whether a tumor has a defect in base excision repair. For example, sequencing of either the genomic DNA or mRNA products of each base excision repair gene (e.g., UNG, PARP1, or LIG1) can be performed on a sample of the tumor to establish whether mutations expected to modulate the function or expression of the gene product are present (Wang et al., Cancer Research 52:4824 (1992)). In addition to the mutational inactivation, tumor cells can modulate a DNA repair gene by hypermethylating its promoter region, leading to reduced gene expression. This is most commonly assessed using methylation-specific polymerase chain reaction (PCR) to quantify methylation levels on the promoters of base excision repair genes of interest. Analysis of base excision repair gene promoter methylation is available commercially (world wide web site sabiosciences.com/dna_methylation_product/HTML/MEAH-421A.html).

Finally, the expression levels of base excision repair genes can be assessed by directly quantifying levels of the mRNA and protein products of each gene using standard techniques such as quantitative reverse transcriptase-coupled polymerase chain reaction (RT-PCR) and immunohistochemistry (IHC), respectively (Shinmura et al., Carcinogenesis 25: 2311 (2004); Shinmura et al., Journal of Pathology 225:414 (2011)).

In some embodiments, the base excision repair protein is UNG, SMUG1, MBD4, TDG, OGG1, MYH, NTH1, MPG, NEIL1, NEIL2, NEIL3 (DNA glycosylases); APE1, APEX2 (AP endonucleases); LIG1, LIG3 (DNA ligases I and III); XRCC1 (LIG3 accessory); PNK, PNKP (polynucleotide kinase and phosphatase); PARP1, PARP2 (Poly(ADP-Ribose) Polymerases); PolB, PolG (polymerases); FEN1 (endonuclease) or Aprataxin.

In some embodiments, the base excision repair protein is PARP1, PARP2, or PolB. In other embodiments, the base excision repair protein is PARP1 or PARP2.

The methods described above (gene sequence, promoter methylation and mRNA expression) may also be used to characterize the status (e.g., expression or mutation) of other genes or proteins of interesting, such DNA-damaging oncogenes expressed by a tumor or defects in the ATM signaling cascade of a cell.

Manufacture of Medicaments

Another embodiment provides the use of a compounds or compositions described herein for the manufacture of a medicament for treating cancer. In some embodiments, the compound or composition is combined with an additional therapeutic agent, such as a DNA damaging agent, described herein. In another embodiment, the cancer has a defect in a pathway described herein.

Some embodiments provide the use of a first compound for inhibiting ATR kinase in combination with a second compound for inhibiting Chk1 kinase for the manufacture of a medicament for treating cancer in a patient. In another embodiment, the first compound and second compound are combined with one or more additional therapeutic agents selected from an agent in the section entitled "Additional Therapeutic Agents" of the present application. In yet another embodiment, the cancer is selected from a cancer in the section entitled "Therapeutic Uses" of the present application.

In other embodiments, the compound for inhibiting ATR kinase is represented by Formula I:

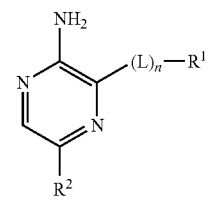

or a pharmaceutically acceptable salt thereof, wherein the variables are as defined in the section entitled "Compounds" in the specification of the present application. Additionally, other Formula I compounds useful for inhibiting ATR kinase are also described in the "Compounds" section of the application.

In still other embodiments, the compound for inhibiting ATR kinase is represented by Formula II:

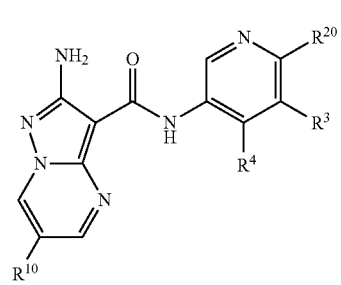

or a pharmaceutically acceptable salt thereof, wherein the variables are as defined in the section entitled "Compounds" of the present application. Additionally, other Formula II compounds useful for inhibiting ATR kinase are also described in the "Compounds" section of the application.

Other embodiments provide the use of a first compound for inhibiting ATR kinase in combination with a second compound for inhibiting Chk1 kinase for the manufacture of a medicament for promoting cell death in cancer cells.

ABBREVIATIONS

The following abbreviations are used:
DMSO dimethyl sulfoxide
ATP adenosine triphosphate
$^1$HNMR proton nuclear magnetic resonance
HPLC high performance liquid chromatography
LCMS liquid chromatography-mass spectrometry
TLC thin layer chromatography
Rt retention time
HATU 1-[Bis(dimethylamino)methylene]-1H-1,2,3-triazolo[4,5-b]pyridinium 3-oxid hexafluorophosphate
TBTU 2-(1H-benzotriazole-1-yl)-1,1,3,3-tetramethyluronium tetrafluoroborate
T3P Propylphosphonic anhydride
COMU 1-[(1-(Cyano-2-ethoxy-2-oxoethylideneaminooxy)-dimethylamino-morpholino)]uroniumhexafluorophosphate
TCTU [(6-chlorobenzotriazol-1-yl)oxy-(dimethylamino)methylene]-dimethyl-ammonium tetrafluoroborate
HBTU O-Benzotriazole-N,N,N',N'-tetramethyl-uronium-hexafluoro-phosphate
DMF dimethylformamide
PTSA p-Toluenesulfonic acid
DIPEA N,N-diisopropylethylamine
DCM dichloromethane
NMP N-methyl-2-pyrrolidone
EDCI 1-Ethyl-3-(3-dimethylaminopropyl)carbodiimide

SCHEMES AND EXAMPLES

The compounds may be prepared according to the schemes and examples described in WO 2010/071837 and WO 2014089379, the contents of which are hereby incorporated by reference. Those compounds may be analyzed by known methods, including but not limited to LCMS (liquid chromatography mass spectrometry) and NMR (nuclear magnetic resonance). The following generic schemes illustrate how to prepare the compounds of the present disclosure. Any examples are for the purpose of illustration only and are not to be construed as limiting the scope of the invention in any way. $^1$H-NMR spectra were recorded at 400 MHz using a Bruker DPX 400 instrument. Mass spec. samples were analyzed on a MicroMass Quattro Micro mass spectrometer operated in single MS mode with electrospray ionization.

Scheme I-A1: Preparation of Compounds wherein —L—R$^1$ is an Aromatic Amide

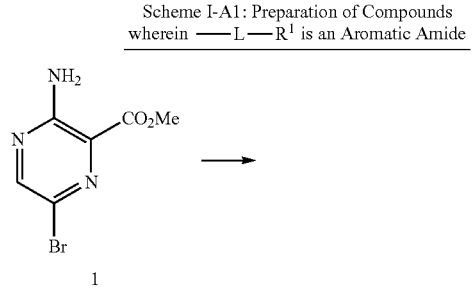

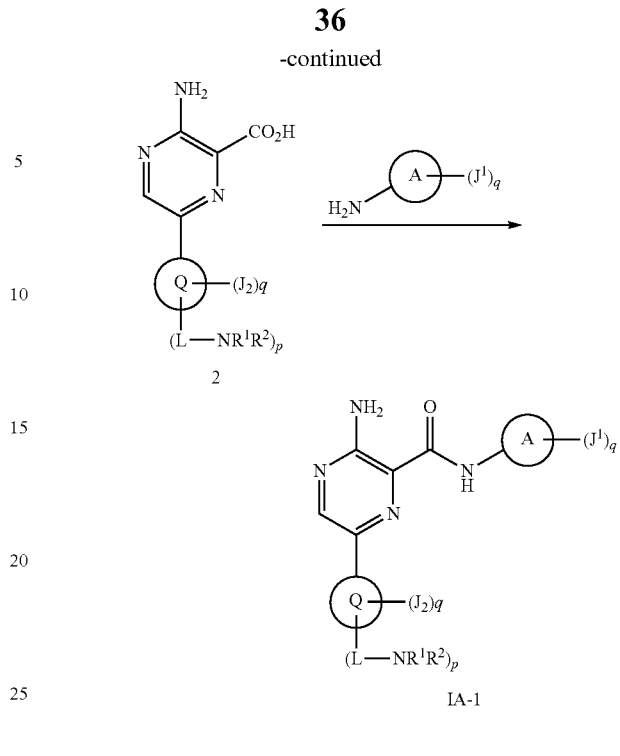

Cyclic amides compounds of the present disclosure wherein -L-R$^1$ is an aromatic amide can be prepared according to methods similar to the one depicted in Scheme I-A1: Commercially available ester 1 is reacted with a boronic acid under Suzuki conditions to give intermediate 2. The carboxylic acid group is engaged in a coupling reaction with an amine to lead to cyclic amide compounds of the Formula IA-1.

Scheme I-A2: Preparation of Compounds wherein —L—R$^1$ is an Aromatic Amide

-continued

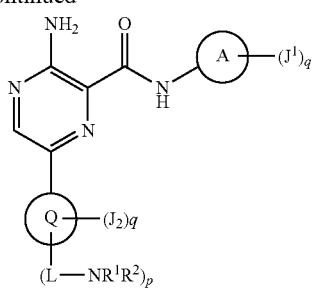

IA-2

-continued

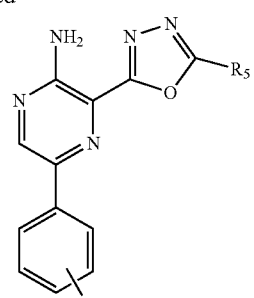

I-B1 wherein R is -(L-NR$^1$R$^2$)$_p$ or -(J$_2$)$_q$

Alternatively, compounds of the present disclosure wherein -L-R$^1$ is an aromatic amide can be prepared according to methods similar to the one depicted in Scheme I-A2, a variation of the synthetic sequence depicted in scheme I-A1 which consists in starting from methyl ester 1. Ester 1 is transformed into carboxylic acid 3 which is engaged in a coupling reaction with an amine to give amide 4. This is reacted with a boronic acid under Suzuki conditions to lead to compounds of formula IA-2.

Compounds of the present disclosure where Ring A is a 1,3,4-oxadiazole can be prepared according to methods similar to the one depicted in Scheme I-B1: methyl ester 3 is reacted with a boronic acid under Suzuki conditions to give intermediate 8. The carboxylic acid in 8 is then engaged into a coupling reaction with an hydrazide (X=O) or thiohydrazide (X=S) to form 9. Finally, the acylhydrazide in 9 undergoes a cyclodehydration to lead to compounds of the present disclosure (formula I in Scheme I-B1). Transformation of intermediate 8 into compounds of formula IB-1 has also been performed in a one-pot procedure using reagents serving two purposes (coupling and cyclodehydration).

Scheme I-B1: preparation of compounds where
Ring A is a 1,3,4-oxadiazole

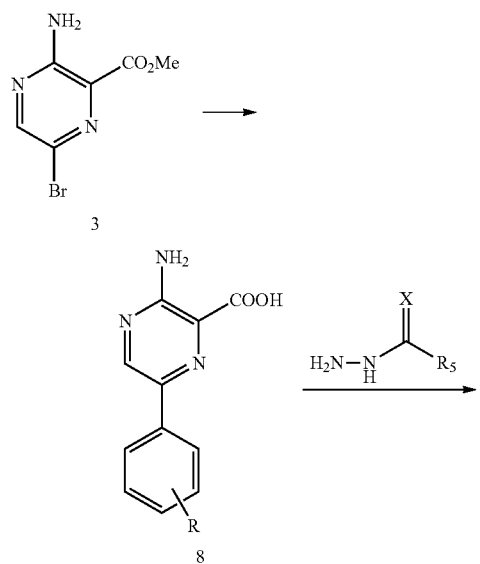

Scheme I-B2: preparation of compounds where
Ring A is a 1,3,4-oxadiazole

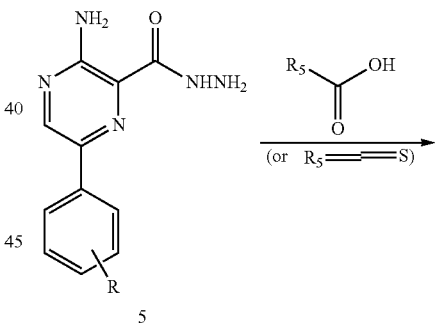

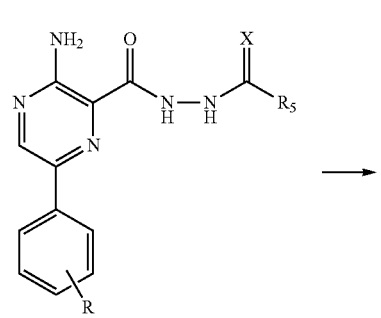

9

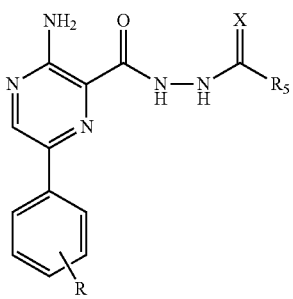

9

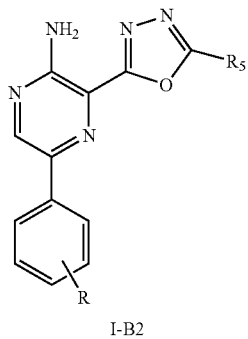

I-B2 wherein R is -(L-NR$^1$R$^2$)$_p$ or -(J$_2$)$_q$

Alternatively, compounds of the present disclosure where Ring A is a 1,3,4-oxadiazole can be prepared according to methods similar to the one depicted in Scheme I-B2, a variation of the synthetic sequence depicted in scheme I-B1. The hydrazide 5 is engaged in a coupling reaction with a carboxylic acid functional group to form intermediate 9 (X=O). As in scheme I-B1 the acylhydrazide then undergoes a cyclodehydration to lead to compounds of formula IB-2. When R5 is a moiety bound to the oxadiazole ring through a C—N bond, then an thioisocyanate can be used to generate intermediate 9 (X=S); the thioacylhydrazide then undergoes a cyclodehydration to lead to compounds of formula IB-2.

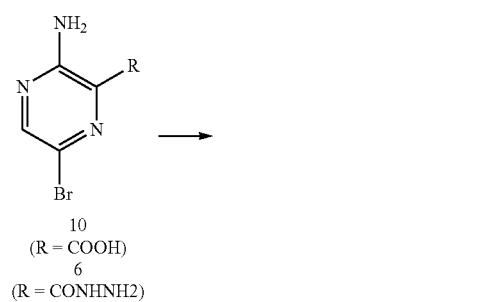

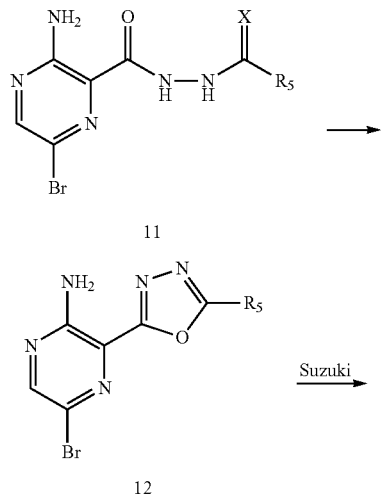

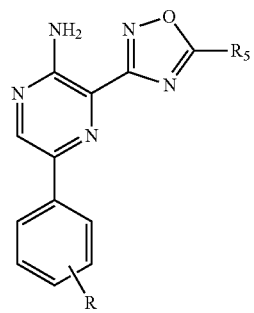

I-B3 wherein R is -(L-NR$^1$R$^2$)$_p$ or -(J$_2$)$_q$

Alternatively, compounds of the present disclosure where Ring A is 1,3,4-oxadiazole can be prepared according to methods similar to the one depicted in Scheme I-B3: the R functional group in 10 or 6 (acid and hydrazide respectively, both prepared from methyl ester 3 through hydrolysis and hydrazinolysis respectively) are engaged into coupling with a suitable partner (R$_5$CXNHNH$_2$ when starting from 10; R$_5$COOH/R$_5$=S when starting from 6) to form acylhydrazide intermediate 11. Subsequent cyclodehydration leads to the compound 12 where the 1,3,4-oxadiazole ring has been constructed. Transformation of starting point 10 or 6 into intermediate 12 has also been performed in a one-pot procedure using reagents serving two purposes (coupling and cyclodehydration). The bromo handle in oxadiazole 12 is then reacted with a boronic acid under Suzuki conditions to give compounds of formula IB-3. When R group in Formula IB-3 contains a carboxylic acid moiety, it can be further transformed (eg into an amide) using conditions known in the art.

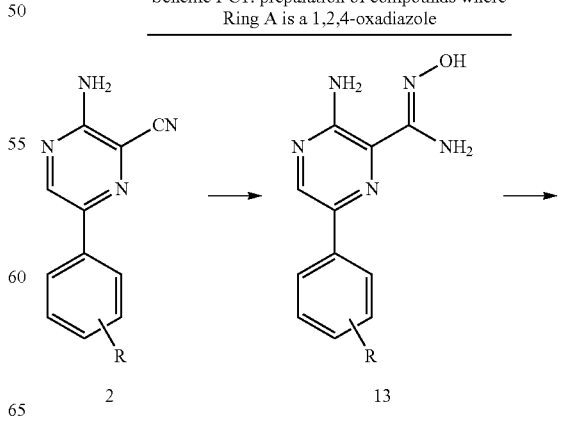

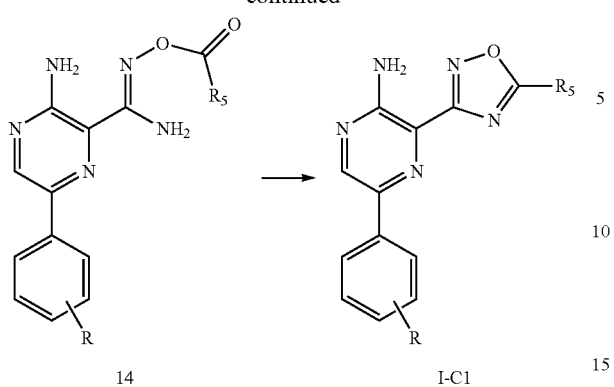

14 → I-C1

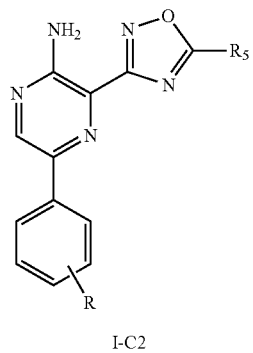

I-C2 wherein R is $-(L-NR^1R^2)_p$ or $-(J_2)_q$

Compounds of the present disclosure where Ring A is a 1,2,4-oxadiazole can be prepared according to methods similar to the one depicted in Scheme I-C1: nitrile 2 reacts with hydroxylamine to give intermediate 13. The hydroxy group in 13 reacts with acid chlorides to lead to intermediate 14 which undergoes cyclodehydration to afford compounds of formula IC-1.

wherein R is $-(L-NR^1R^2)_p$ or $-(J_2)_q$

Alternatively, compounds of the present disclosure where Ring A is a 1,2,4-oxadiazole can be prepared according to methods similar to the one depicted in Scheme I-C2: Commercially available nitrile 1 reacts with hydroxylamine to give intermediate 15. The hydroxy group in 15 reacts with acid chlorides to lead to intermediate 16 which undergoes cyclodehydration to afford intermediate 17. The bromo handle in 17 is then used to perform a Suzuki reaction with a boronic acid coupling partner to give compounds of formula IC-2. When R group in Formula IC-2 contains a carboxylic acid moiety, it can be further transformed (eg into an amide) using conditions known in the art.

Scheme I-C2: preparation of compounds where Ring A is a 1,2,4-oxadiazole

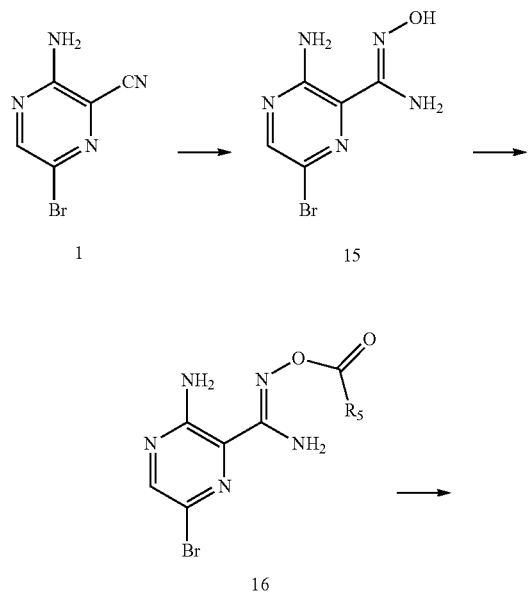

Scheme I-D1: preparation of compounds where Ring A is a 1,3,4-thiadiazole

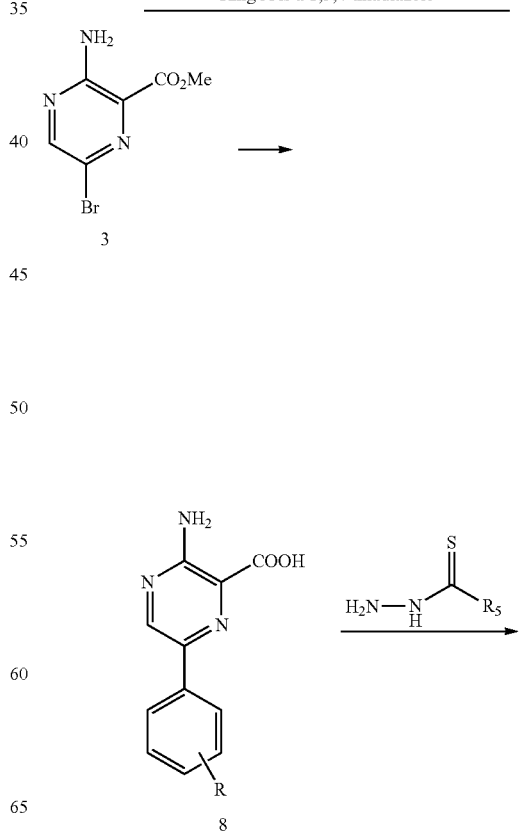

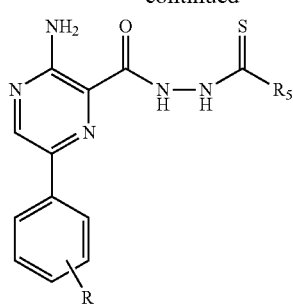

18

I-D1 wherein R is -(L-NR$^1$R$^2$)$_p$ or -(J$_2$)$_q$

Compounds of the present disclosure where Ring A is a 1,3,4-thiadiazole can be prepared according to methods similar to the one depicted in Scheme I-D1: methyl ester 3 is reacted with a boronic acid under Suzuki conditions to give intermediate 8. The carboxylic acid in 8 is then engaged into a coupling reaction with a thiohydrazide to form 18. Finally, the thioacylhydrazide in 18 undergoes a cyclodehydration to lead to compounds of Formula ID-1. Transformation of intermediate 8 into compounds of Formula I-D1 can be performed in a one-pot procedure using reagents serving two purposes (coupling and cyclodehydration)

Scheme I-D2: preparation of compounds where Ring A is a 1,3,4-thiadiazole

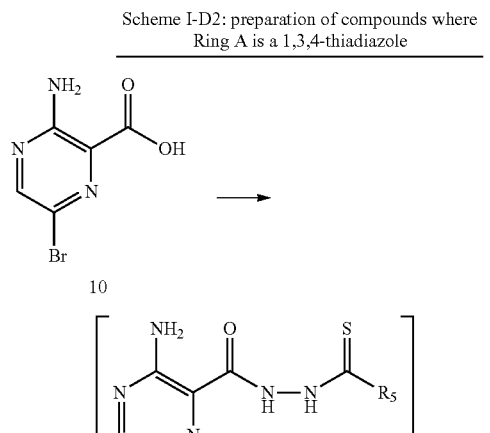

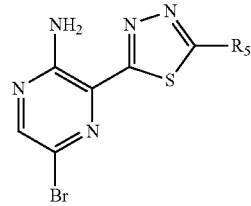

20

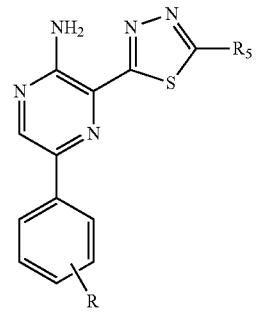

I-D2 wherein R is -(L-NR$^1$R$^2$)$_p$ or -(J$_2$)$_q$

Alternatively, compounds of the present disclosure where Ring A is 1,3,4-thiadiazole can be prepared according to methods similar to the one depicted in Scheme I-D2: the acid functional group in 10 is engaged into coupling with a suitable partner (R$_5$CSNHNH$_2$) to form the thioacylhydrazide intermediate 19. Subsequent cyclodehydration leads to the compound 20 where the 1,3,4-thiadiazole ring has been constructed. Transformation of starting point 10 into 20 has been performed in a one-pot procedure using reagents serving two purposes (coupling and cyclodehydration). The bromo handle in thiadiazole 20 is then reacted with a boronic acid under Suzuki conditions to give compounds of formula I-D2. When R group in Formula I-D2 contains a carboxylic acid moiety, it can be further transformed (eg into an amide) using conditions known in the art.

Scheme I-E1: preparation of compounds where Ring A is an isoxazole

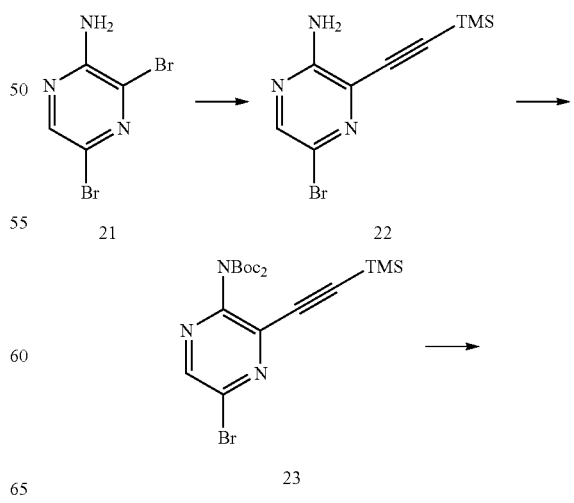

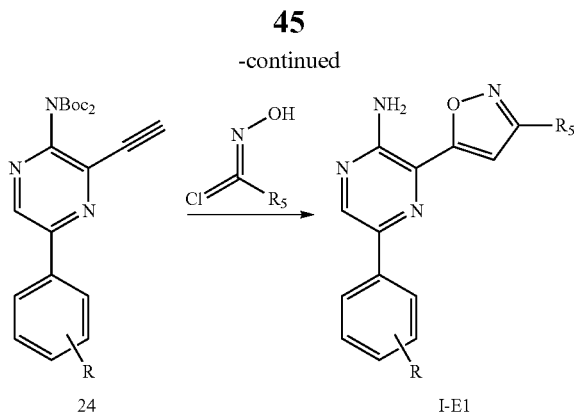

wherein R is -(L-NR$^1$R$^2$)$_p$ or -(J$_2$)$_q$

Compounds of the present disclosure where Ring A is an isoxazole can be prepared according to methods similar to the one depicted in Scheme I-E1: Commercially available 2-amino-3,5-dibromo pyrazine 21 undergoes a Sonogashira coupling with TMS-acetylene to give intermediate 22, the amino group of which can be fully protected as the diBoc species 23. A Suzuki coupling with the remaining bromo handle, with concommitent TMS deprotection affords intermediate 24. The alkyne 24 finally reacts in a cyclocondensation with N-hydroxyaroyl chloride to furnish compounds of Formula I-E1.

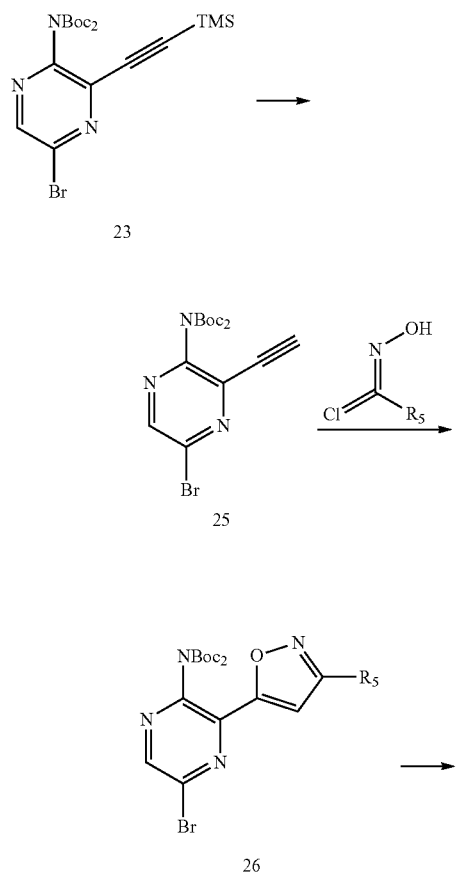

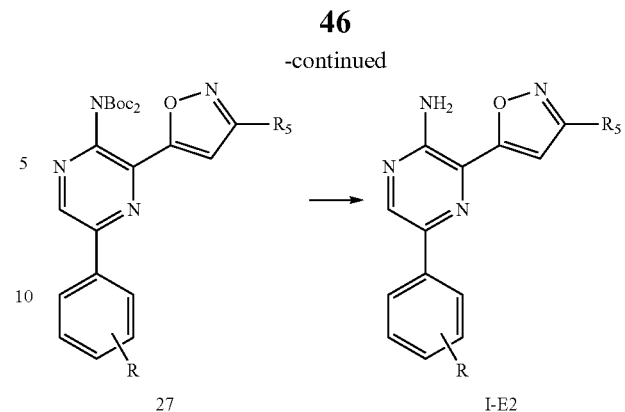

wherein R is -(L-NR$^1$R$^2$)$_p$ or -(J$_2$)$_q$

Alternatively, compounds of the present disclosure where Ring A is an isoxazole can be prepared according to methods similar to the one depicted in Scheme I-E2: The TMS-protected intermediate 23, described in scheme I-E1 can be deprotected to reveal the alkyne compound 25. The alkyne 25 reacts in a cyclocondensation with N-hydroxyaroyl chloride to furnish intermediate 26 where the isoxazole ring has been constructed. The bromo handle in isoxazole 26 is then reacted with a boronic acid under Suzuki conditions to give compounds 27. A final deprotection of N-protecting groups in 27 can reveal compounds of Formula I. When R group in Formula I-E2 contains a carboxylic acid moiety, it can be further transformed (eg into an amide) using conditions known in the art.

Scheme I-E3: preparation of compounds where Ring A is an isoxazole

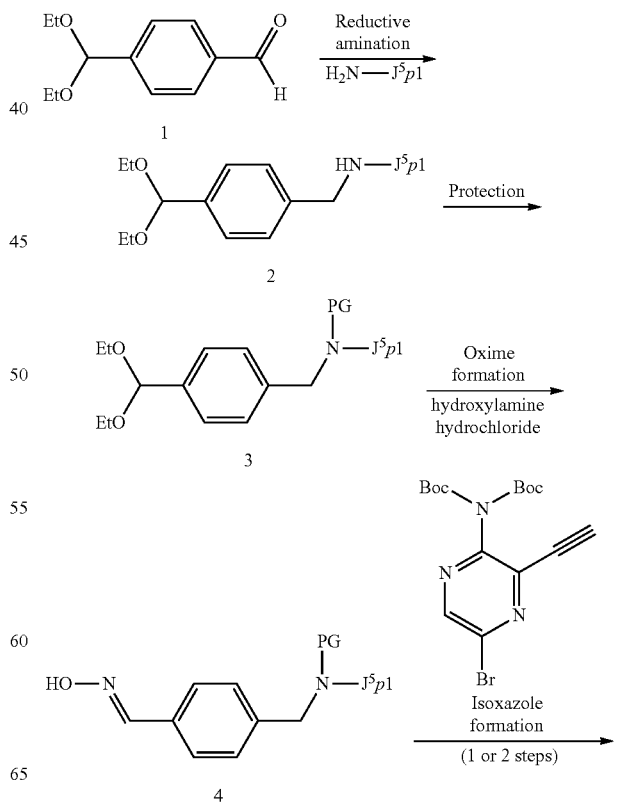

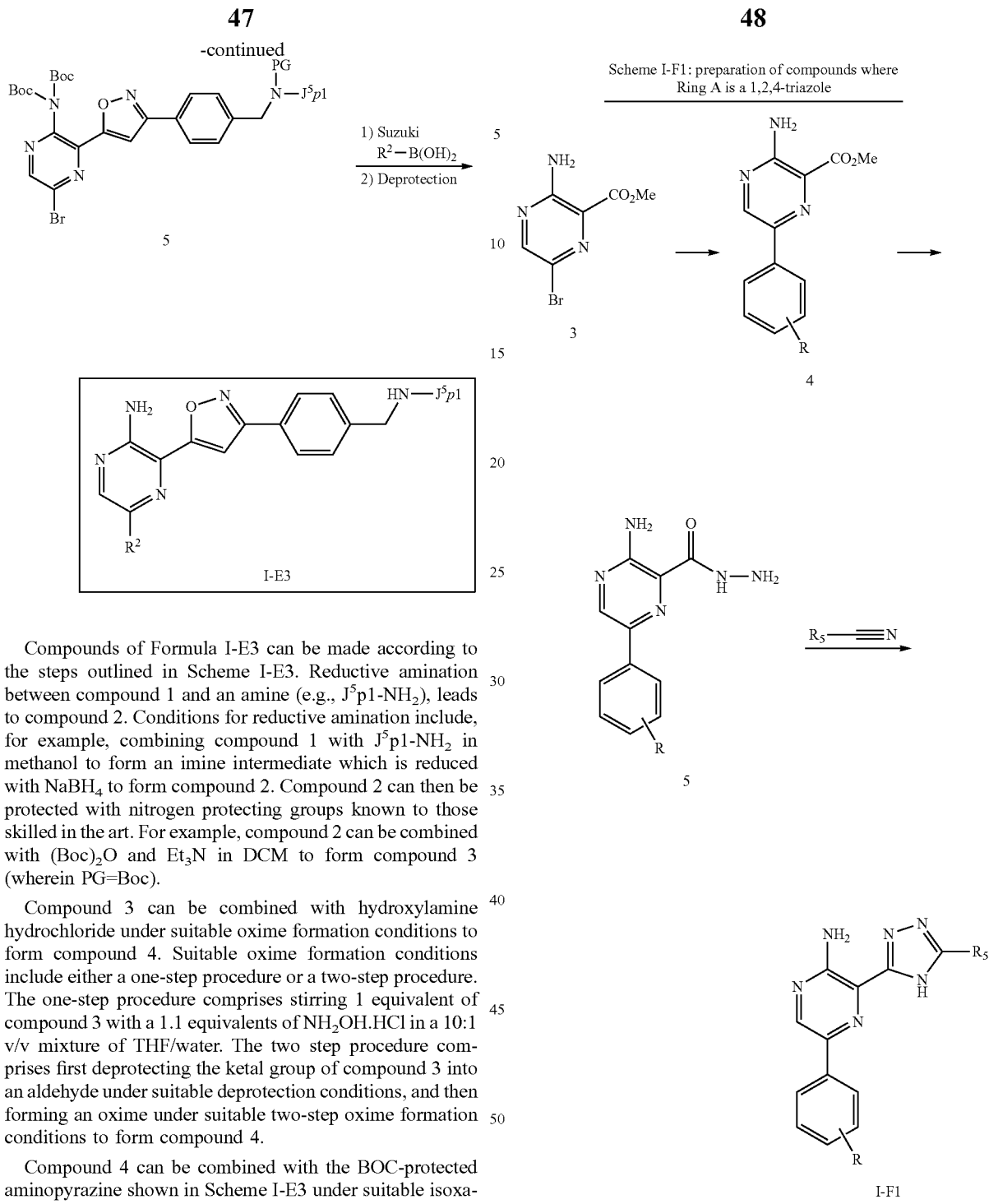

Compounds of Formula I-E3 can be made according to the steps outlined in Scheme I-E3. Reductive amination between compound 1 and an amine (e.g., $J^5p1\text{-}NH_2$), leads to compound 2. Conditions for reductive amination include, for example, combining compound 1 with $J^5p1\text{-}NH_2$ in methanol to form an imine intermediate which is reduced with $NaBH_4$ to form compound 2. Compound 2 can then be protected with nitrogen protecting groups known to those skilled in the art. For example, compound 2 can be combined with $(Boc)_2O$ and $Et_3N$ in DCM to form compound 3 (wherein PG=Boc).

Compound 3 can be combined with hydroxylamine hydrochloride under suitable oxime formation conditions to form compound 4. Suitable oxime formation conditions include either a one-step procedure or a two-step procedure. The one-step procedure comprises stirring 1 equivalent of compound 3 with a 1.1 equivalents of $NH_2OH.HCl$ in a 10:1 v/v mixture of THF/water. The two step procedure comprises first deprotecting the ketal group of compound 3 into an aldehyde under suitable deprotection conditions, and then forming an oxime under suitable two-step oxime formation conditions to form compound 4.

Compound 4 can be combined with the BOC-protected aminopyrazine shown in Scheme I-E3 under suitable isoxazole formation conditions to form compound 5. Compound 4 is transformed and engaged in a [3+2] cycloaddition to form the isoxazole 5. This transformation can be conducted in one pot but requires two distinct steps. The first step is an oxidation of the oxime functional group into a nitrone, or a similar intermediate with the same degree of oxidation, for example a chlorooxime. This reactive species then reacts with an alkyne in a [3+2] cycloaddition to form the isoxazole adduct.

Finally, compound 5 undergoes a metal-assisted coupling reaction to form compound 6. For example, compound 5 can be combined with a boronic acid under Suzuki cross-coupling conditions to form the compound of formula 6.

wherein R is $\text{-}(L\text{-}NR^1R^2)_p$ or $\text{-}(J_2)_q$

Alternatively, compounds of the present disclosure where Ring A is a 1,2,4-triazole can be prepared according to methods similar to the one depicted in Scheme I-F1 starting from methyl ester 3. Ester 3 is reacted with a boronic acid under Suzuki conditions to give intermediate 4. When R group contains a carboxylic acid moiety, it can be further transformed at this stage (eg into an amide) using conditions known in the art. The methyl ester group in 4 is then transformed into an hydrazide by reaction with hydrazine to give 5. Finally, the hydrazide group in 5 is engaged in a coupling reaction with a nitrile and subsequently undergoes a cyclodehydration to lead to compounds of Formula I-F1.

Scheme I-F2: preparation of compounds where Ring A is a 1,2,4-triazole

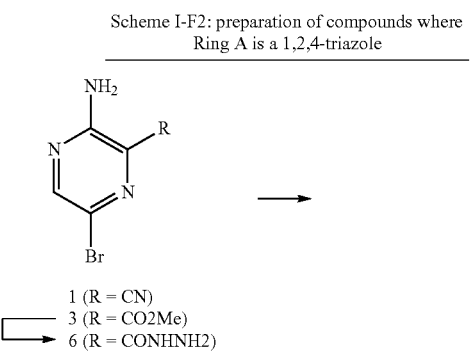

1 (R = CN)
3 (R = CO2Me)
6 (R = CONHNH2)

wherein R is -(L-NR¹R²)$_p$ or -(J$_2$)$_q$

Alternatively, compounds of the present disclosure where Ring A is a 1,2,4-triazole can be prepared according to methods similar to the one depicted in Scheme I-F2: the R functional group in 1 or 3 (nitrile and methyl ester respectively) are engaged into coupling (after appropriate transformation of 3 into hydrazide 6) with a suitable coupling partner (R$_5$CONHNH$_2$ when starting from 1; R$_5$CN if using 6). Subsequent cyclodehydration leads to the intermediate 7 where the 1,2,4-triazole ring has been constructed. The bromo handle in triazole 7 is then reacted with a boronic acid under Suzuki conditions to give compounds of formula I-F2. When R group in Formula I-F2 contains a carboxylic acid moiety, it can be further transformed (eg into an amide) using conditions known in the art.

Scheme I-G1: preparation of compounds where Ring A is a benzoxazole wherein R is -(L-NR¹R²)$_p$ or -(J$_2$)$_q$ Benzoxazole compounds of Formula VI can be prepared according to methods similar to the one depicted in Scheme I-G1: Commercially available nitrile 1 is reacted with a amino phenol to give the benzoxazole which is then reacted with a boronic acid under Suzuki conditions to give compounds of the Formula I-G1.

Scheme I-H1: preparation of compounds where Ring A is a benzothiazole

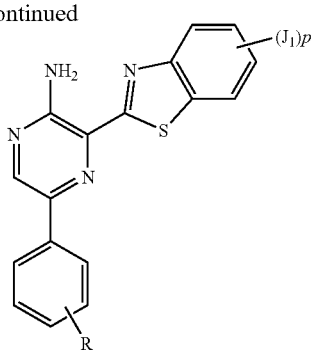

I-H1 wherein R is -(L-NR$^1$R$^2$)$_p$ or -(J$_2$)$_q$

Benzothiazole compounds of Formula VI can be prepared according to methods similar to the one depicted in Scheme I-H1: Commercially available nitrile 1 is reacted with a aminobenzenethiol to give the benzothiazole which is then reacted with a boronic acid under Suzuki conditions to give compounds of the Formula I-H1.

Scheme I-H2: preparation of compounds where benzothiazole

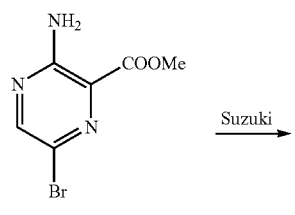

3

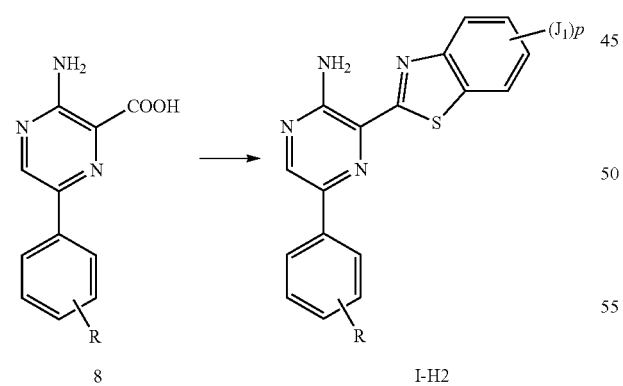

8 → I-H2 wherein R is -(L-NR$^1$R$^2$)$_p$ or -(J$_2$)$_q$

Alternatively, benzothiazole compounds of Formula VI can be prepared according to Scheme I-H2; methyl ester 3 is reacted with a boronic acid under Suzuki conditions to give intermediate 8. Cyclisation of intermediate 8 with an amino benzenethiol will lead to compounds of the Formula I-H2.

Scheme I-I1: preparation of compounds where Ring A is an imidazole

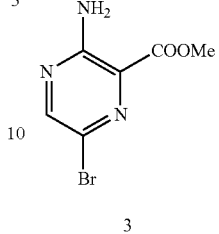

3

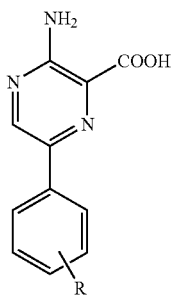

8

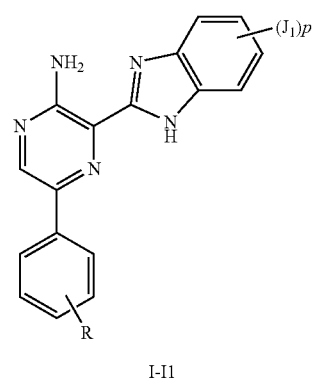

I-I1 wherein R is -(L-NR$^1$R$^2$)$_p$ or -(J$_2$)$_q$

Benzimidazole compounds of Formula I can be prepared according to methods similar to the one depicted in Scheme I-I1: methyl ester 3 is reacted with a boronic acid under Suzuki conditions to give intermediate 8. Cyclisation of intermediate 8 with a benzene 1,2-diamine will lead to compounds of the Formula I-I1.

Scheme I-I2: preparation of compounds where Ring A is a imidiazole

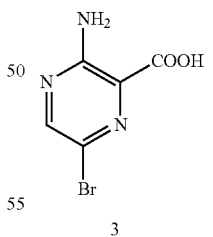

3

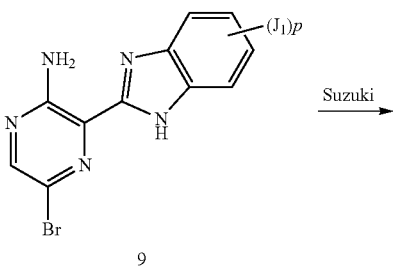

9

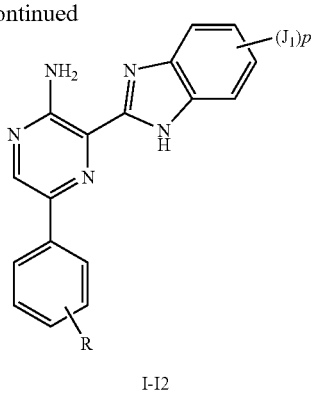

I-I2 wherein R is -(L-NR$^1$R$^2$)$_p$ or -(J$_2$)$_q$

Alternatively, benzimidazole compounds of Formula I can be prepared according to methods similar to the one depicted in Scheme I-I2: Reaction of the acid functional group of 3 is reacted with a benzene 1,2-diamine to give the benzimidazole intermediate 9. Intermediate 9 is then reacted with a boronic acid under Suzuki conditions to give compounds of the Formula I-I2.

The anion of commercially available allyl cyanoacetate 28 can react with trichloroacetonitrile to provide intermediate 29. In the anion condensation step, the anion of commercially available allyl cyanoacetate 28 can be generated with a base such as potassium acetate in an appropriate solvent such as an alcohol (e.g., isopropylalcohol). The anion then reacts with trichloroacetonitrile at room temperature.

Intermediate 29 then reacts with hydrazine to form the diaminopyrazole 30. In the pyrazole formation step, intermediate 29 is reacted with hydrazine (or its hydrate) in an aprotic solvent, such as DMF, to provide the diaminopyrazole 30. The reaction occurs under basic conditions (e.g., in the presence of potassium acetate or AcONa) with heating (e.g., 110° C.) to ensure complete cyclisation.

Intermediate 30 can further be condensed with a dielectrophilic coupling partner to form the pyrimidine 31. In the pyrimidine formation step, intermediate 30 is reacted with a 1,3-dielectrophilic species (e.g., a 1,3-dialdehyde or a 3-(dialkylamino)-prop-2-enal) in various types of solvents (e.g., DMF or DMSO/water) to furnish the bicyclic cores 31. When one or two of the electrophilic centers is protected/masked (e.g., aldehyde masked as a ketal), introduction of a sulfonic acid (e.g., PTSA) is required to liberate the reactive functional group.

Scheme IIa: General approach for the preparation of compounds of formula II

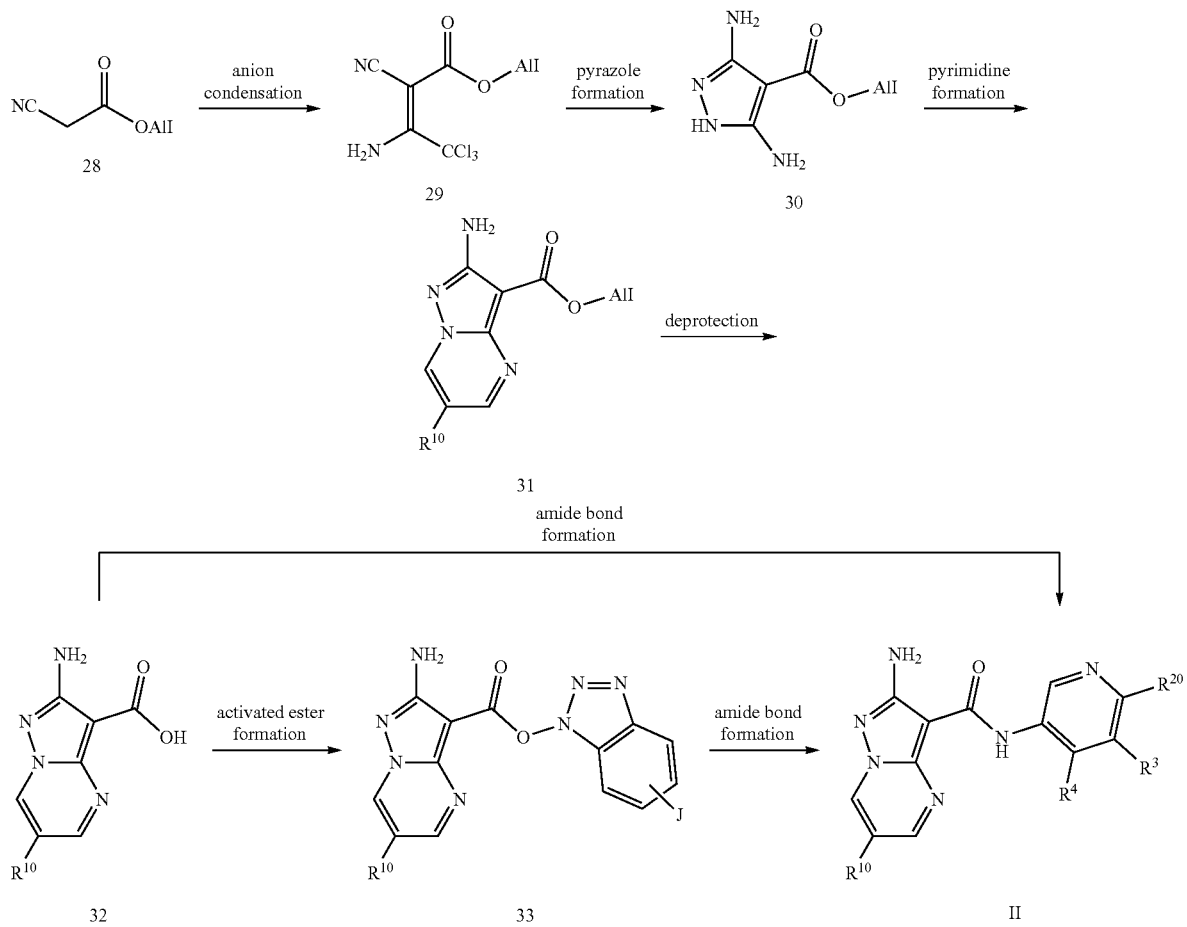

Compounds of this invention can be synthesised according to methods similar to the one depicted in Scheme IIa.

Deprotection, e.g, via hydrolysis, of the allyl ester leads to the carboxylic acids 32. In the deprotection step, compound 31 is subjected to hydrolytic conditions that are known to those skilled in the art. For example, treatment of 31 with phenylsilane or 4-methylbenzenesulfinate in the presence of a catalytic amount of palladium (e.g., Pd(PPh$_3$)$_4$) leads to the formation of the corresponding carboxylic acid 32. Alternatively, compounds 31 could be treated with aqueous alkali (e.g., NaOH, LiOH, or KOH) to produce acids 32.

In the activated ester formation step, the carboxylic acids 32 are reacted with amide coupling agents known to those skilled in the art. Suitable amide coupling partners include, but are not limited to TBTU, TCTU, HATU, T3P, and COMU. When the coupling agent is chosen appropriately, the reactions can proceed rapidly (~1 h) at room temperature in the presence of an organic base (e.g., triethylamine, DIPEA) to provide the activated esters 33. For example, when the amide coupling agents TBTU [J=H] or TCTU [J=Cl] are used, compounds 33 are obtained readily by filtration of the reaction mixture.

Formation of the activated esters 33 prior to the amide bond formation to prepare II is generally preferred, although a direct conversion of 32 into the compounds of formula II of this invention is also possible. Alternative activated esters can also be utilised (isolated or formed in situ) and will be known to those skilled in the art (e.g., using TBTU, TCTU, HATU, T3P, COMU coupling agents).

In the amide bond formation step, activated esters 33 can react with a substituted 3-aminopyridine to provide compounds of formula II of this invention. The reaction conditions for the amide coupling are generally in an aprotic solvent (e.g., NMP, pyridine, DMF, etc. . . . ) with heating (e.g., ≥90° C.). The 3-aminopyridine may be further functionalized following amide bond formation.

Alternatively, the two steps described above can be combined: carboxylic acids 32 can be used as starting points for the amide bond formation, the activated esters being generated in situ, using the same amide couplings agents as those described above. Compounds II of this invention are isolated in a similar manner to the one described above.

Scheme IIb: Alternative approach for the preparation of compounds of formula II

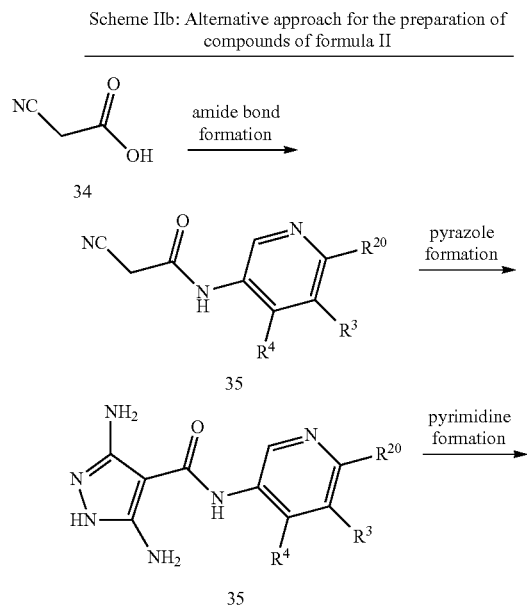

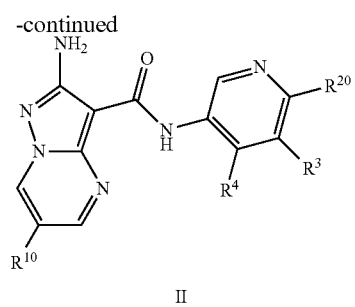

II

Alternatively, compounds of the present disclosure can be prepared according to methods similar to the one depicted in Scheme IIb.

Step 1

The amide 35 can readily be prepared from commercially available cyanoacetic acid 34. In the amide bond formation step, cyanoacetic acid 34 can react with a substituted 3-aminopyridine to provide compounds 35 of this invention. The reaction conditions for the amide coupling are generally in an aprotic solvent (e.g., DCM, NMP, DMF, etc), in the presence of an organic base, such as an aliphatic amine, (e.g., triethylamine or DIPEA) and an amide coupling agent known to those skilled in the art: for example EDCI, TBTU, COMU, T3P, etc. . . .

Step 2

In the pyrazole formation step, the anion of cyanoamide 35 can be generated with a base (such as potassium or sodium acetate) in an appropriate solvent such as an alcohol (e.g., ethanol). The anion then reacts with trichloroacetonitrile at room temperature. The resulting solid, which can be collected by filtration, is then reacted with hydrazine (or its hydrate) in an aprotic solvent, such as DMF or NMP, to provide the diaminopyrazole 36, the latter being further condensed with a dielectrophilic coupling partner to form the pyrimidine portion of the compounds of formula II of this invention.

Step 3

In the pyrimidine formation step, intermediate 36 is reacted with a 1,3-dielectrophilic species (e.g., a 1,3-dialdehyde or a 3-(dialkylamino)-prop-2-enal) in various types of solvents (e.g., iPrOH/water, DMF, or DMSO/water) to furnish the desired products II. When one or two of the electrophilic centers is protected/masked (e.g., aldehyde masked as a ketal), introduction of a sulfonic acid (e.g., PTSA) is required to liberate the reactive functional group.

ATR/Chk1 Combination Therapy

Example 1

Inhibition of Chk1 and ATR Inhibition Leads to High Levels of DNA Damage

As shown in FIG. 1, the impact of Chk1 inhibition by AZD7762 on DNA damage levels from treatment of cancer cells with the ATR inhibitor VE-821 was assessed by measuring the accumulation of pan nuclear γH2AX, a widely used marker of DNA damage. γH2AX was detected by western blot. U2OS cancer cells were incubated overnight in 96 well plates and treated for 8 hr. with DMSO AZD7762(60 nM) and/or VE-821 (10 uM). Cells were stained with anti phosphor (serin 139) histone H2AX antibody as primary and Alexa 555 as secondary. Operetta was used to take images, which were analyzed using Columbus software. Intensity ≥2000 AU was consider as pan nuclear γH2AX cell positive. Data are presented as mean±S.E.M.

Treatment of U2OS cancer cells with either the ATR inhibitor VE-821 or the Chk1 inhibitor AZD7762 alone had minimal impact on the percentage of cells positive for pan nuclear γH2AX (<5% cells were positive for pan nuclear γH2AX). In contrast treatment with both agents led to >20% cells staining positive for pan nuclear γH2AX. This is consistent with increased DNA damage. This data supports that combination of Chk1 inhibitors and ATR inhibitors can lead to increased DNA damage in cancer cells.

Example 2a

Figure 2A:
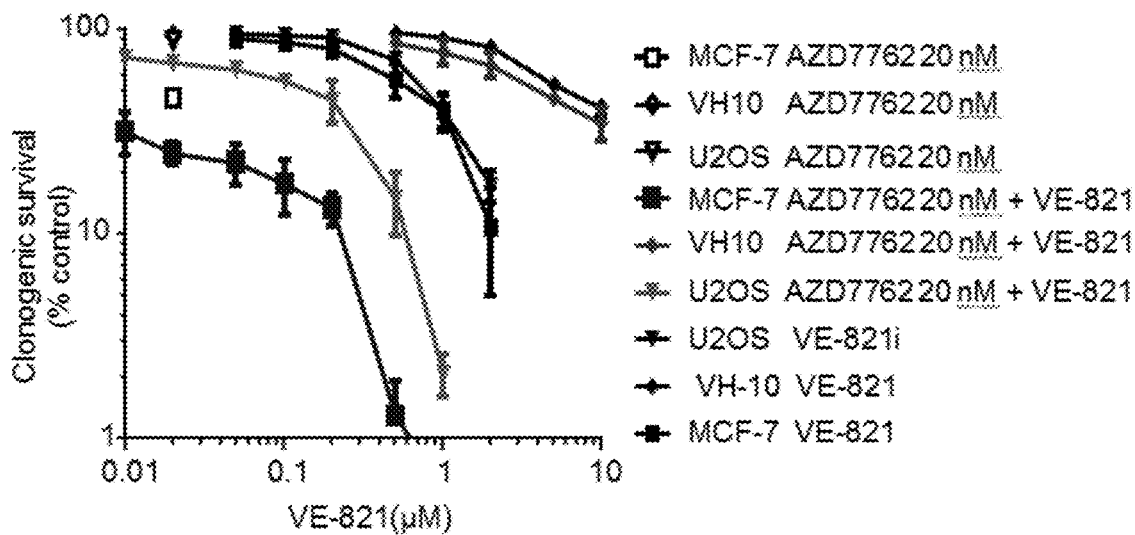
FIG. 2A: graph showing the clonogenic survival of a panel of cell lines treated alone and in combination with AZD7762 and VE-821.
Figure 2B:
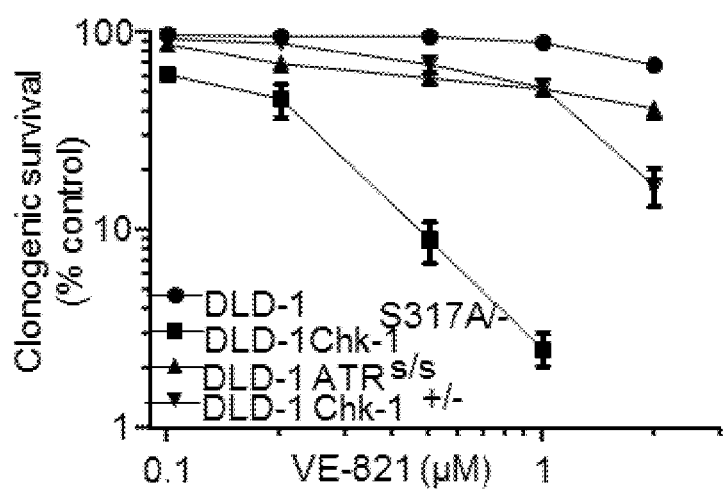
FIG. 2B: graph showing the clonogenic survival of a panel of cell lines treated with VE-821.

Inhibition of Chk1 or Expression of Inactive Mutant Forms of Chk1 Sensitise Cancer Cells to ATR Inhibition Referring to FIG. 2A and FIG. 2B, the impact of Chk1 inhibition or expression of inactive Chk1 mutant on cell response to the ATR inhibitor VE-821 was assessed using a clonogenic survival assay in a variety of cancer cells. 500 cells of U2OS, MCF-7, DLD-1, DLD-1 Chk-1$^{S317A/-}$, DLD-1 Chk-1$^{+/-}$, DLD-1 ATR$^{S/S}$ and 1000 cells of VH-10 were plated on 10 cm plate. After 5 hr. of incubation (5% CO2 at 37° C.) vehicle (0.05% DMSO max) various concentration of ATR inhibitor VE-821 were directly added to the media containing plate and incubated for 72 hr. At the end of 72 hr. of incubation, vehicle and drug containing media was replaced with fresh media and further incubated for another 5-8 days before plates were fixed and stained with 4% methylene blue in MeOH and colonies were counted manually. Each data point represents a triplicate data set±SEM.

Inhibition of Chk1 by AZD7762 (20 nM) resulted in increased sensitivity to the ATR inhibitor VE-821 in MCF-7 and U2OS cancer cells, but had no impact on VH10 non-cancer cells. For example, treatment of MCF-7 and U2OS cells with 1 μM VE-821 alone (a concentration shown previously to inhibit about 50% of ATR activity {ref NCB paper}) resulted in 10-20% clonogenic survival. Additional treatment with the Chk1 inhibitor, AZD7762, led to 2% or less clonogenic survival in both cell systems. Expression of an inactive mutant form of Chk1 equally sensitized cells to the ATR inhibitor VE-821. Parental DLD-1 cells were not affected by treatment with VE-822 (~100% cell viability at 1 μM VE-821), in contrast of treatment of DLD-1 cells expressing the inactive mutant form of Chk1 (S317A/-) with 1 μM VE-821 led to less than 3% viable cells remaining. This data supports that inhibition of Chk1 (or expression of inactive Chk1) can sensitise cancer cells to inhibition of ATR, resulting in reduced cell survival, but that non-cancer cells can tolerate the combination.

Example 2b

Figure 2C:
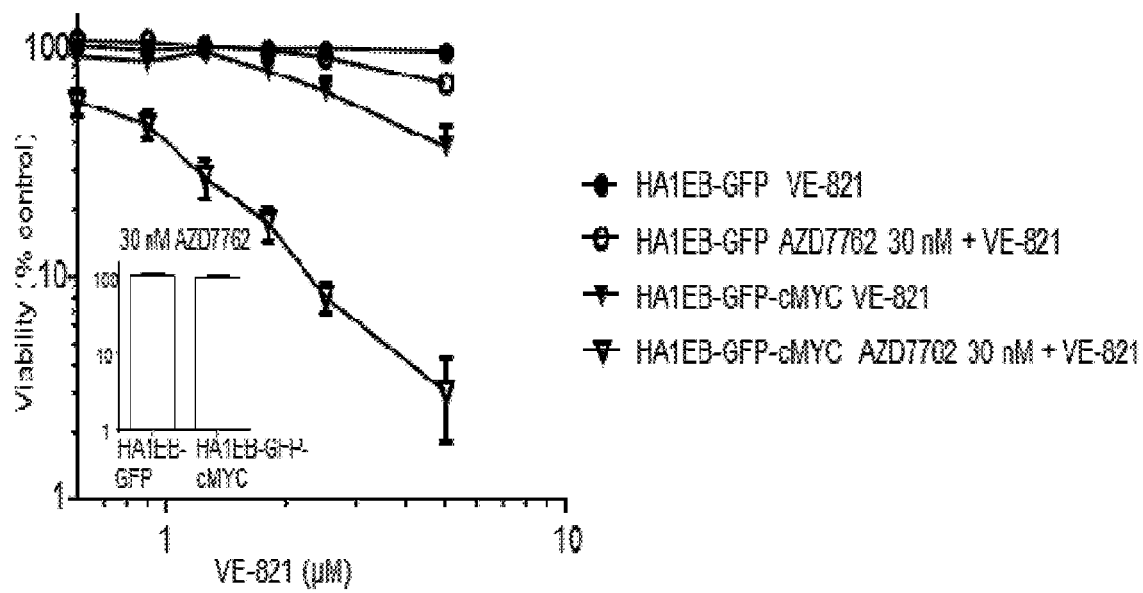
FIG. 2C: graph evaluating the clonogenic survival of a panel of cells overexpressing the cMYC oncogene following treatment alone and in combination with AZD7762 and VE-821.

Expression of the cMYC Oncogene Sensitizes Cells to the Combination of ATR and Chk1 Inhibition Referring to FIG. 2C, an isogenic cell line pair differing only in the expression of the oncogene cMYC (HA1EB-GFP parental and cMYC transformed cells, HA1EB-GFP-cMYC) were treated with either VE-821 alone (at concentrations up to 5 μM), AZD7762 alone (30 nM) or the combination of VE-821 and AZD7762 for 72 hours. Cell viability was assessed by resazurin staining. Neither VE-821 nor AZD7762 had a marked effect on viability of the parental cells. Additionally, AZD7762 alone did not impact the viability of the cMYC transformed cells. In contrast, VE-821 reduced the viability of cMYC transformed cells (~40% viable cells remaining) and the combination markedly reduced cell viability of the cMYC transformed cells (<5% viable cells remaining).

Example 2c

Figure 2D:
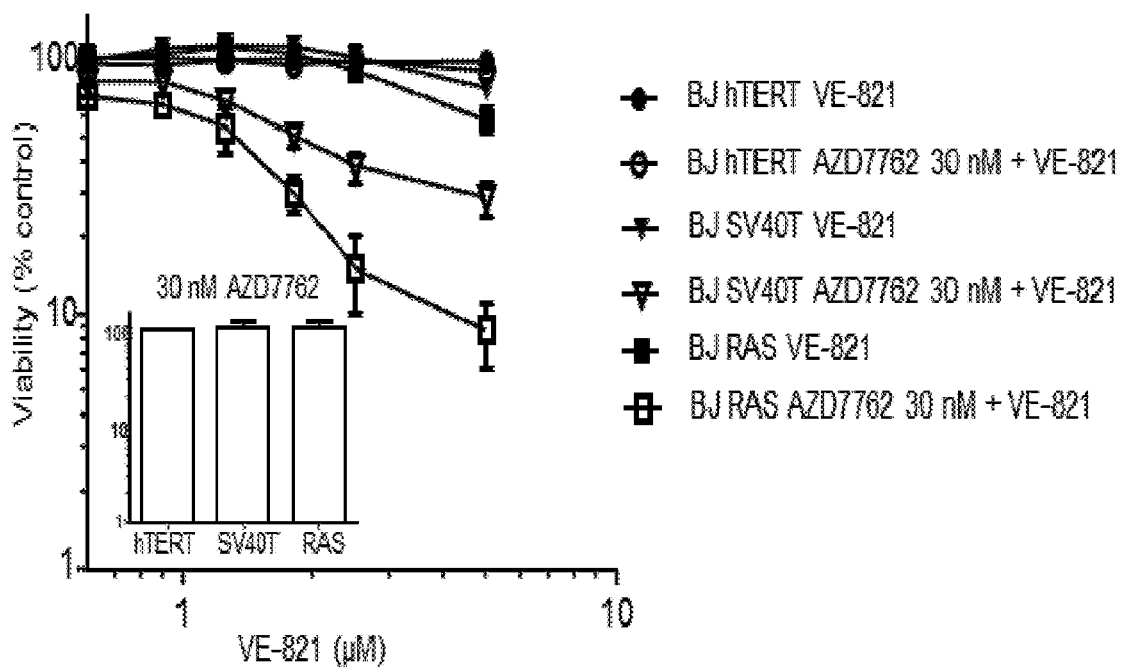
FIG. 2D: graph evaluating the clonogenic survival of a panel of cells with inactive p53 and RB, and overexpressing the H-RAS oncogene following treatment alone and in combination with AZD7762 and VE-821.

Loss of Function of p53 and RB and Expression of the Oncogene H-RAS Sensitize Cells to the Combination of ATR and Chk1 Inhibition Referring to FIG. 2D, an isogenic cell pair was used to assess the impact of loss of p53 and RB on cell sensitivity to the combination of VE-821 and AZD7762 (BJ-hTERT parental cells vs BJ-SV40T cells expressing the Large Tumor Antigen which inactivates p53 and RB function). In addition, the impact of expression of the H-RAS oncogene was assessed in the BJ-SV40T cells transformed with activated H-RAS(G12V) (BJ RAS). Cells were treated with either VE-821 alone (at concentrations up to 5 μM), AZD7762 alone (30 nM) or the combination of VE-821 and AZD7762 for 72 hours. Cell viability was assessed by resazurin staining AZD7762 alone did not have a marked effect on the viability of any of the cell lines. VE-821 alone reduced the viability of the H-RAS transformed cells (~60% viable cells remaining). In contrast, the combination of both VE-821 and AZD7762 markedly reduced the viability of both the p53 and RB inactivated cells (~30% viable cells remaining) and the H-RAS transformed (<10% viable cells remaining).

Example 3

Inhibition of Chk1 Sensitises Tumors to ATR Inhibition

Figure 3A:
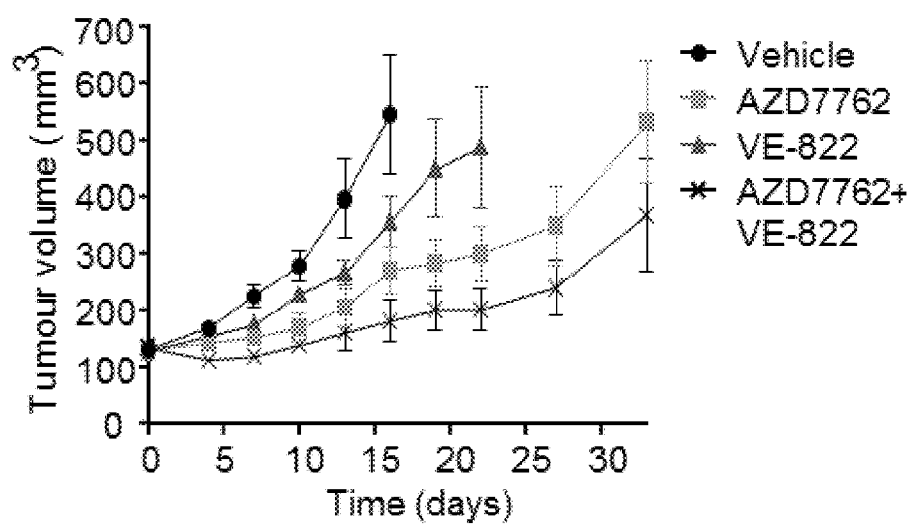
FIG. 3A: graph showing tumour volume of MX1 xenografted mice treated alone and in combination with AZD7762 and VE-822.
Figure 3B:
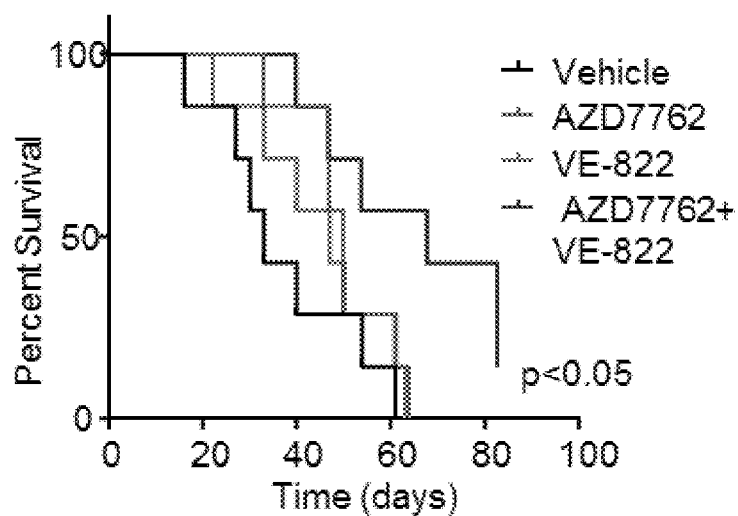
FIG. 3B: graph showing a survival curve for MX1 xenografted mice treated alone and in combination with AZD7762 and VE-822.
Figure 4A:
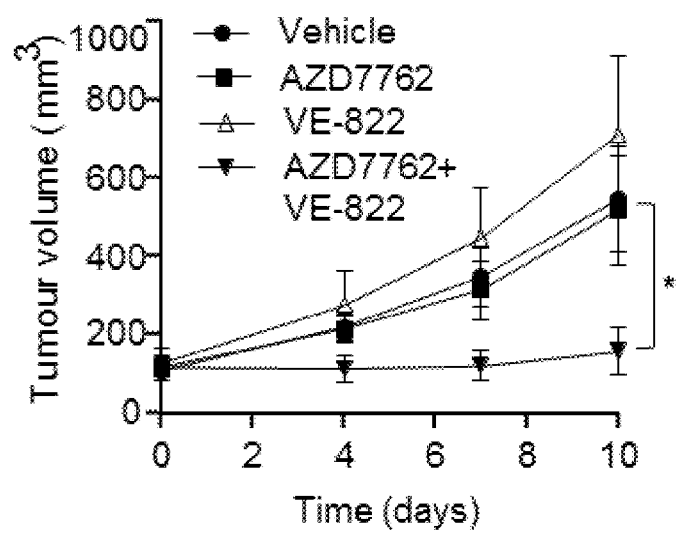
FIG. 4A: graph showing tumour volume of H460 xenografted mice treated alone and in combination with AZD7762 and VE-822.
Figure 4B:
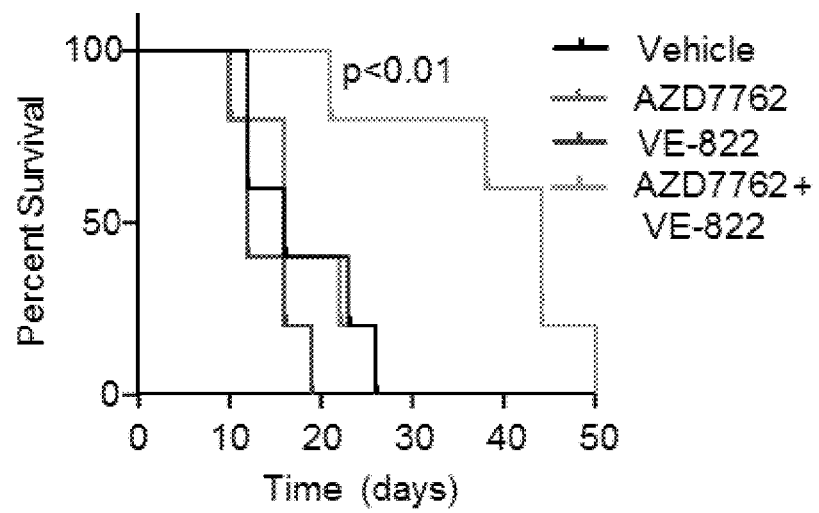
FIG. 4B: graph showing a survival curve for H460 xenografted mice treated alone and in combination with AZD7762 and VE-822.

The impact of Chk1 inhibition on tumor response to the ATR inhibitor VE-821 was assessed in two different mouse xenograft models in Balb/C nude mice using the MX-1 breast cancer cell line (FIG. 3A and FIG. 3B) and the H460 lung cancer cell line (FIG. 4A and FIG. 4B). In the case of the MX-1 model, 2 million cells in 50% matrigel were injected in nude mice and for the H460 model 5 million cells in PBS were injected in nude mice. After 8-9 days of implantation animals were divided into 4 groups of 5 animals based on tumor size; with mean tumor volume of 130 mm$^3$. The 1st group were dosed Vehicle (10% D-α-Tocopherol polyethylene glycol 1000 succinate (sigma) in water by oral gavage and 11.3% (2-Hydroxy propyl)-β cyclodextrin in normal saline by intraperitoneal injection. The 2nd group received 25 mg/kg body weight of the Chk1 inhibitor, AZD7762, dissolved in 11.3% (2-Hydroxy propyl)-β cyclodextrin in normal saline by intraperitoneal injection. The 3rd group received 60 mg/kg body weight of the ATR inhibitor, VE-822, dissolved in 10% D-α-Tocopherol polyethylene glycol 1000 succinate in water by oral gavage. The 4th group received both; 25 mg/kg body weight of AZD7762 dissolved in 11.3% (2-Hydroxy propyl)-β cyclodextrin in normal saline by intraperitoneal injection and 60 mg/kg body weight of VE-822 dissolved in 10% D-α-Tocopherol polyethylene glycol 1000 succinate in water by oral gavage. Body weight and tumor volume were measured twice a week. Tumor volume was measured with caliper and shown as mean±S.E.M (length×width×width×0.52).

In the MX-1 mouse xenograft model, treatment with the ATR inhibitor VE-822 had minimal impact on tumor size (FIG. 3A) or survival (FIG. 3B). Treatment with the Chk1 inhibitor, AZD7762 reduced tumor growth but had no impact on survival. Treatment with both agents together led to improved tumor growth inhibition, when compared with either agent alone, and to a statistically significant improvement in survival (P<0.05). In the H460 mouse xenograft model, treatment with either the ATR inhibitor VE-822 or the Chk1 inhibitor AZD7762 alone had minimal impact on tumor size (FIG. 4A) or survival (FIG. 4B). In contrast, the combination of both agents resulted in almost complete tumor growth inhibition and extended survival. For tumor growth the difference between the combination treated group and either monotherapy treated groups reached statistical significance (P<0.05). Similarly for survival the difference between the combination group and either monotherapy treated groups reached statistical significance (P<0.01). In both models the combination was well tolerated with no body weight loss observed. This data supports that combination of Chk1 inhibitors and ATR inhibitors can provide beneficial anti-tumor activity in vivo.

Example 4

Figure 5:
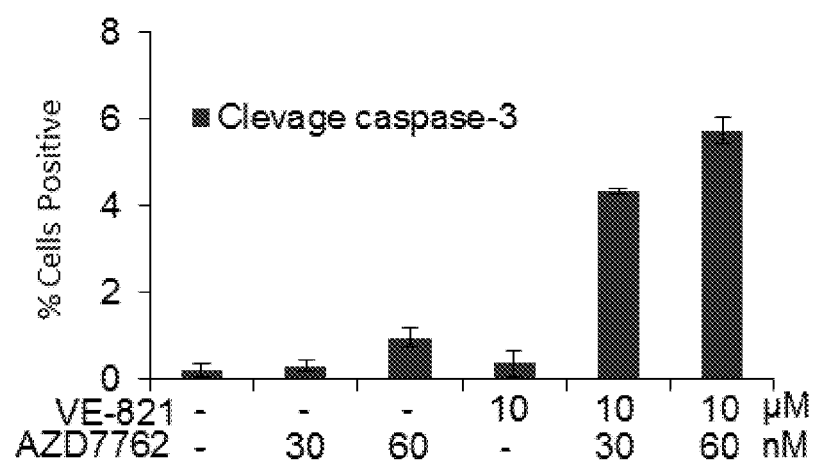
FIG. 5: graph showing the levels of cleaved Caspase-3 in U2OS cells treated alone and in combination with AZD7762 and VE-821.

Inhibition of Chk1 Sensitises Cancer Cells to the Combined Treatment of an ATR Inhibitor and a Representative DNA Damaging Agent Referring to FIG. 5, the impact of Chk1 inhibition by AZD7762 on cell apoptosis from treatment with the ATR inhibitor VE-821 and a representative DNA damaging agent, hydroxyl urea (2 mM), was assessed by measuring levels of cleaved caspase-3, a widely used marker of apoptosis. U2OS cells were treated for 24 hr. with the DNA damaging agent hydroxyurea and varied doses of AZD7762 and/or VE-821. Cells were subsequently stained with anti-cleavage caspase 3 and β actin antibodies and confocal microscopy used to take and quantify images. Data are presented as % cells positive for cleaved capsae-3. Treatment with hydroxyurea alone led to minimal activation of caspase-3 (<0.5% cells positive). The addition of either the Chk1 inhibitor, AZD7762 or the ATR inhibitor VE-821 had minimal impact on caspase-3 cleavage when compared with hydroxyl urea treatment alone (<1% cells positive). In contrast the combination of both agents led to increased caspase-3 cleavage (>4% cells positive). This data supports that combined treatment with a Chk1 and ATR inhibitor can sensitise cells to a DNA damaging agent.

Example 5

Figure 6A:
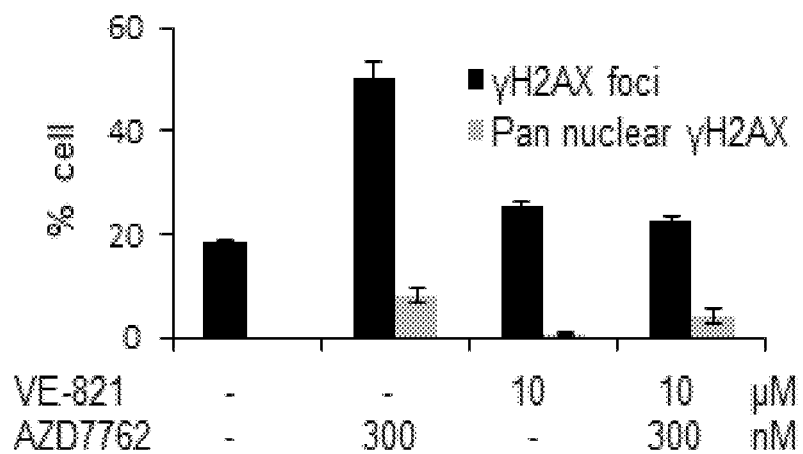
FIG. 6A: graph showing the impact of Chk1 inhibition and ATR inhibition on DNA damage levels in U2OS cancer cells by measuring the accumulation of pan-nuclear γH2AX.
Figure 6B:
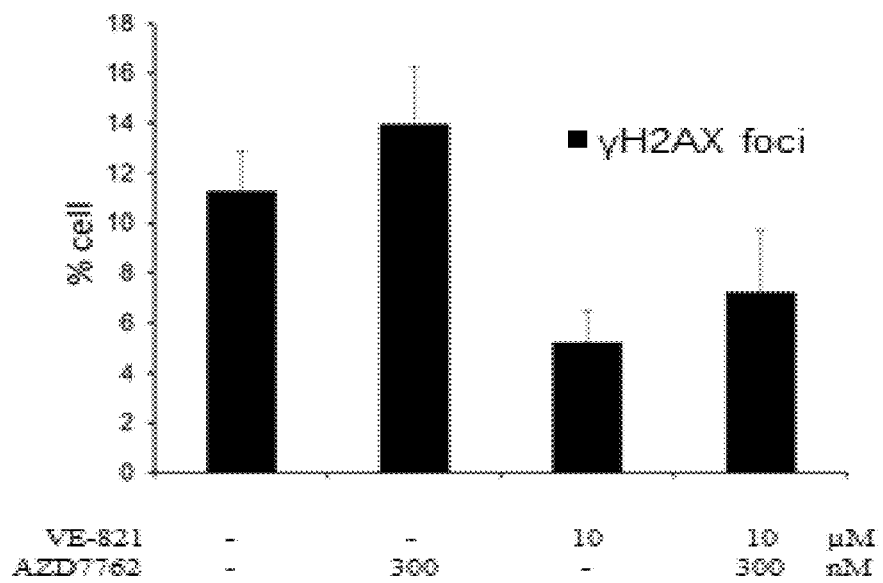
FIG. 6B: graph showing the impact of Chk1 inhibition and ATR inhibition on DNA damage levels in VH-10 normal fibroblast cells by measuring the accumulation of pannuclear γH2AX.

Activation of ATR by a Chk-1 Inhibitor is High in Cancer Cells, but not in Normal Cells As shown in FIG. 6A and FIG. 6B, U2OS cancer cells (FIG. 6A) and VH-10 normal fibroblast cells (FIG. 6B) were treated for 3 hr with DMSO, AZD7762 (300 nM), ATR inhibitor VE-821 (20 µM) and its combination. Cells were fixed in 4% PFA and stained with anti phospho(serine 139) histone H2AX antibody (primary antibody) and Alexa 555 (secondary antibody). A reading of more than 9 foci of γH2AX per cell was considered a positive cell. Histograms show mean±S.E.M. (n=3). This shows that Chk1 inhibition can lead to activation of ATR substrates in cancer but not non-cancer cells.

Figure 6C:
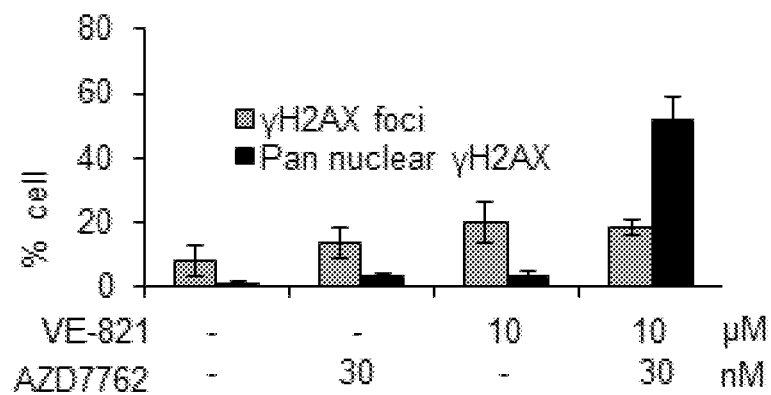
FIG. 6C: graph showing the impact of Chk1 inhibition and ATR inhibition on DNA damage levels in U2OS cancer cells by measuring the accumulation of pan-nuclear γH2AX.
Figure 6D:
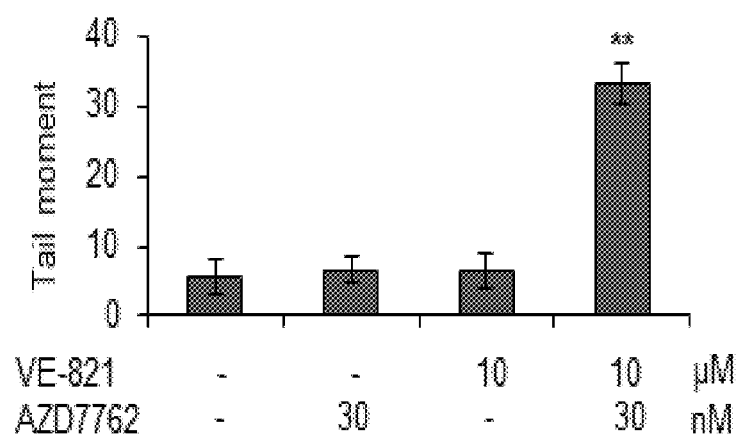
FIG. 6D: graph showing the impact of Chk1 inhibition and ATR inhibition on DNA damage levels in U2OS cancer cells using an alkaline comet assay.

In another example, shown in FIG. 6C and FIG. 6D, the impact of Chk1 inhibition by AZD-7762 and ATR inhibition by VE-821 on DNA damage levels in cancer cells was again assessed by measuring the accumulation of pan-nuclear γH2AX, a widely used indicator of high levels of DNA damage (FIG. 6C) and by alkaline comet assay, which measures DNA breaks (FIG. 6D). U2OS cancer cells were treated for 24 hr with DMSO, AZD-7762 (30 nM) and/or VE-821 (10 uM). For assessment of γH2AX, cells were then stained with antiphospho (serine 139) histone H2AX antibody as primary antibody and a fluorescent secondary antibody, and the Operetta fluorescence microscope was used to take images which were analyzed using Columbus software. Cells with nine or more γH2AX foci were considered γH2AX positive. Cells with smeared γH2AX and no distinguishable foci were considered pan-nuclear γH2AX cell positive. For assessment of DNA breaks by comet assay, the cells were processed by agarose gel electrophoresis under alkaline denaturing conditions and the DNA was stained with YOYO-1 dye. The Operetta fluorescence microscope was used to take images which were analyzed using Cometscore software. Data are presented as mean±S.E.M.

Treatment of U2OS cancer cells with either the ATR inhibitor VE-821 or the Chk1 inhibitor AZD-7762 alone, or treatment with both agents, had minimal impact on the percentage of cells γH2AX positive at this time point (24 hr). Treatment with either VE-821 or AZD-7762 alone had minimal impact on the percentage of cells positive for pan-nuclear γH2AX (<5% cells positive) or displaying comet tail moments indicative of DNA breaks (<10% cells positive). In contrast treatment with both agents led to >50% cells staining positive for pan-nuclear γH2AX (FIG. 6C) and >30% cells displaying comet tails (FIG. 6D). These results indicate that the combination of Chk1 inhibitors and ATR inhibitors can lead to increased DNA damage in cancer cells.

Example 6

Figure 7A:
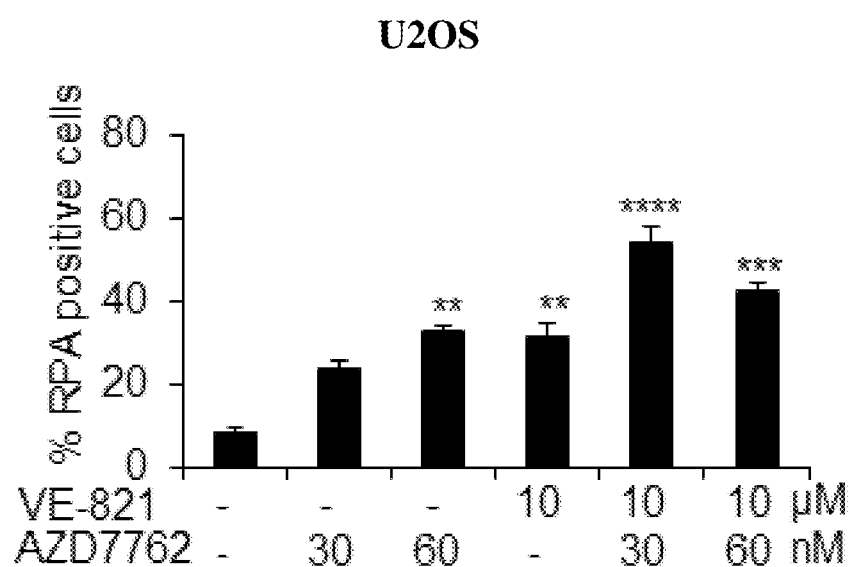
FIG. 7A: graph showing levels of ssDNA in U2OS cancer cells following treatment with a Chk1 inhibitor and ATR inhibitor, alone and in combination.
Figure 7B:
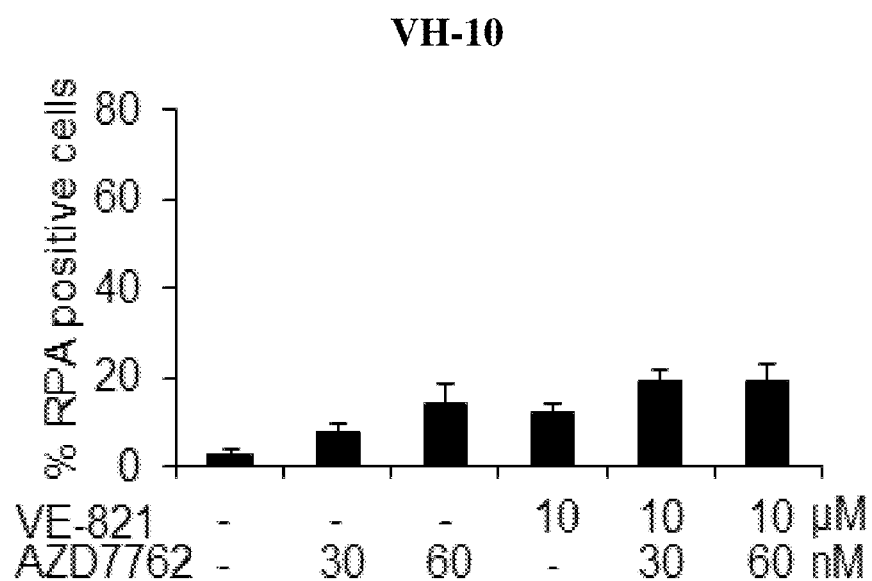
FIG. 7B: graph showing levels of ssDNA in VH-10 normal fibroblast cells following treatment with a Chk1 inhibitor and ATR inhibitor, alone and in combination.
Figure 8A:
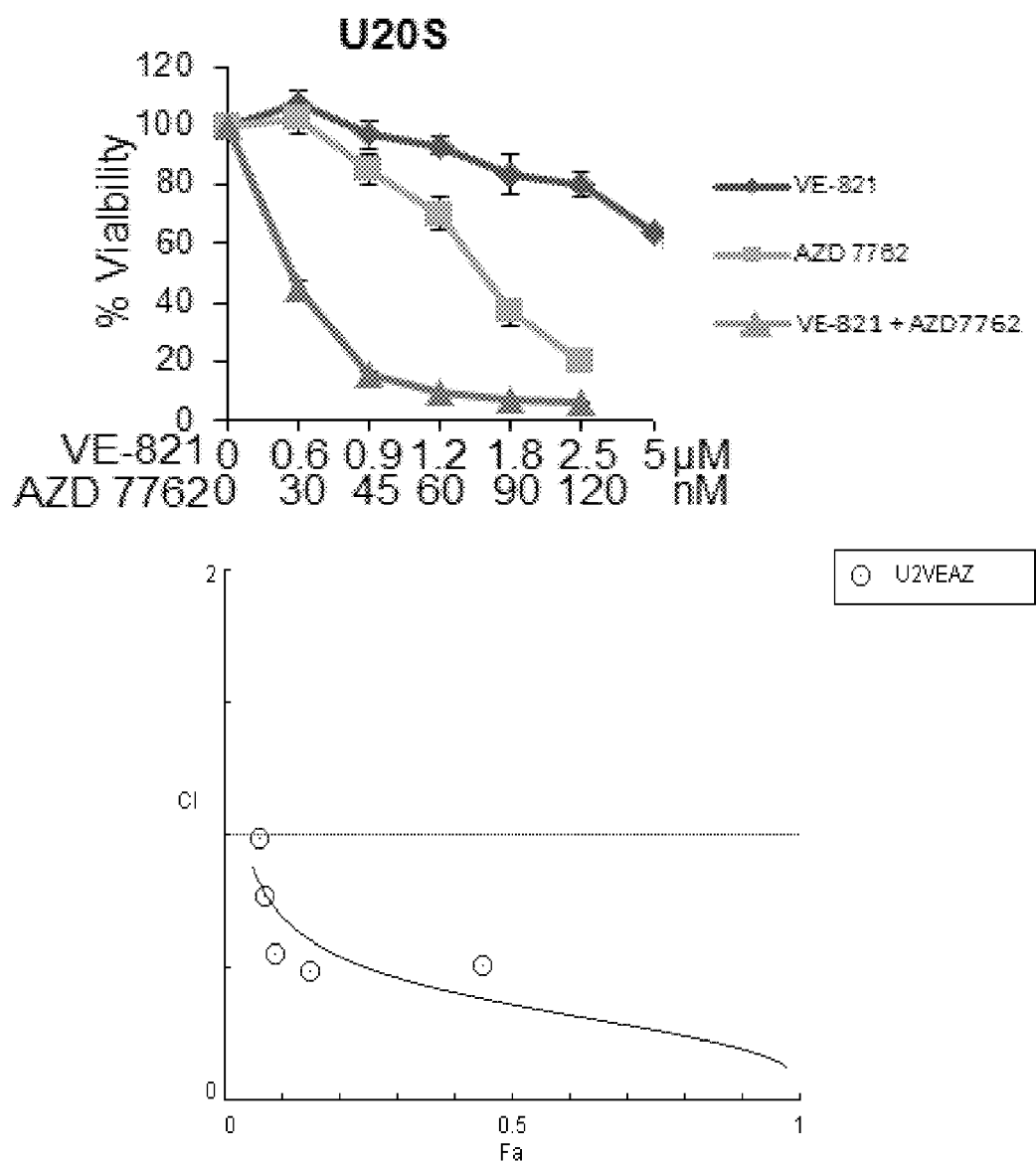
FIG. 8A: graph showing cell viability of U2OS cancer cells following combination treatment with a Chk1 inhibitor and ATR inhibitor.
Figure 8B:
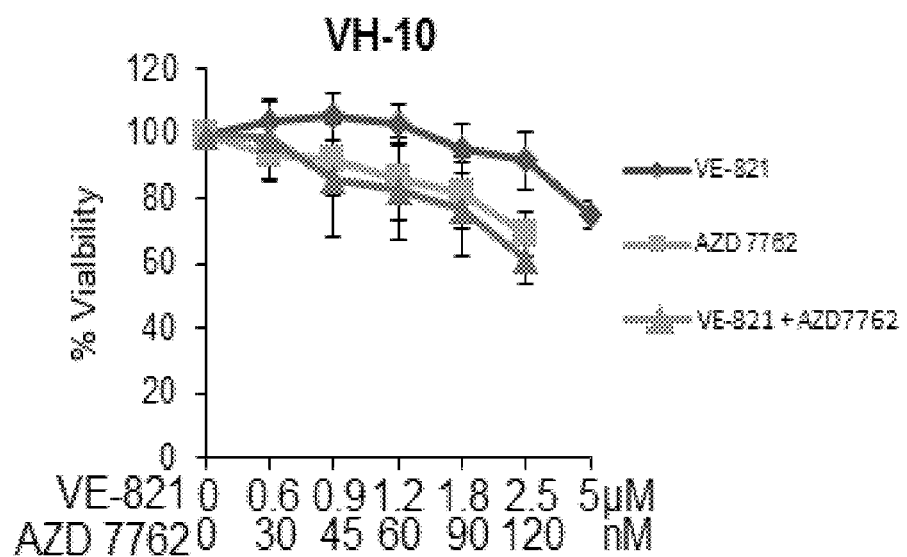
FIG. 8B: graph showing cell viability of VH-10 normal fibroblast cells following combination treatment with a Chk1 inhibitor and ATR inhibitor.
Figure 8B:
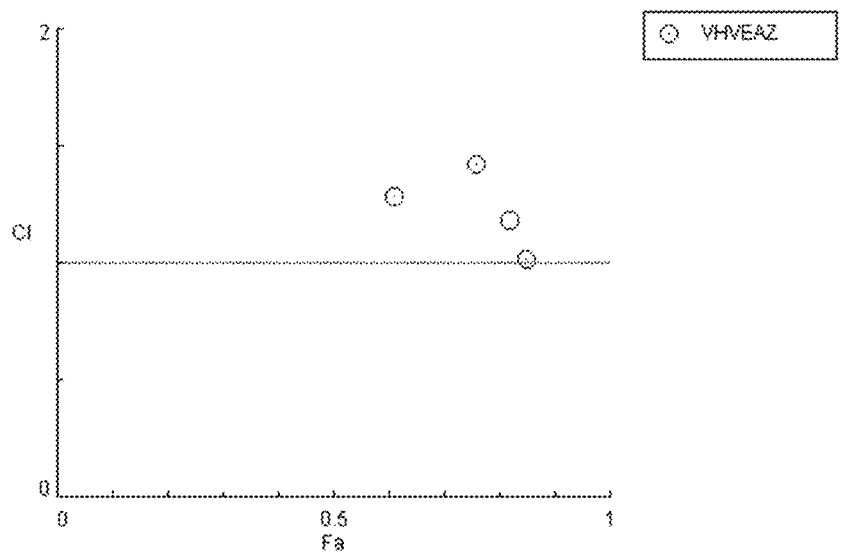
Figure 8C:
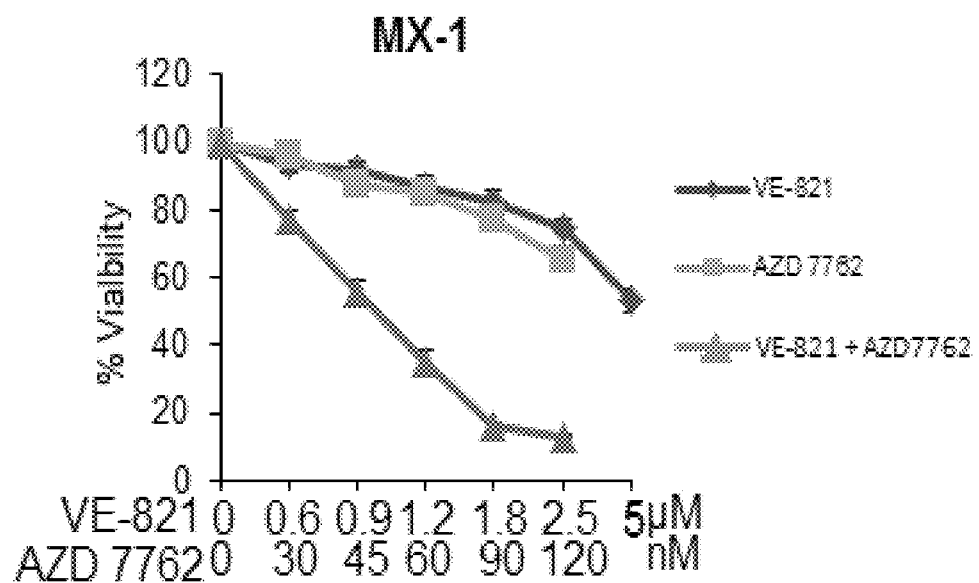
FIG. 8C: graph showing cell viability of H460 cancer cells following combination treatment with a Chk1 inhibitor and ATR inhibitor.
Figure 8C:
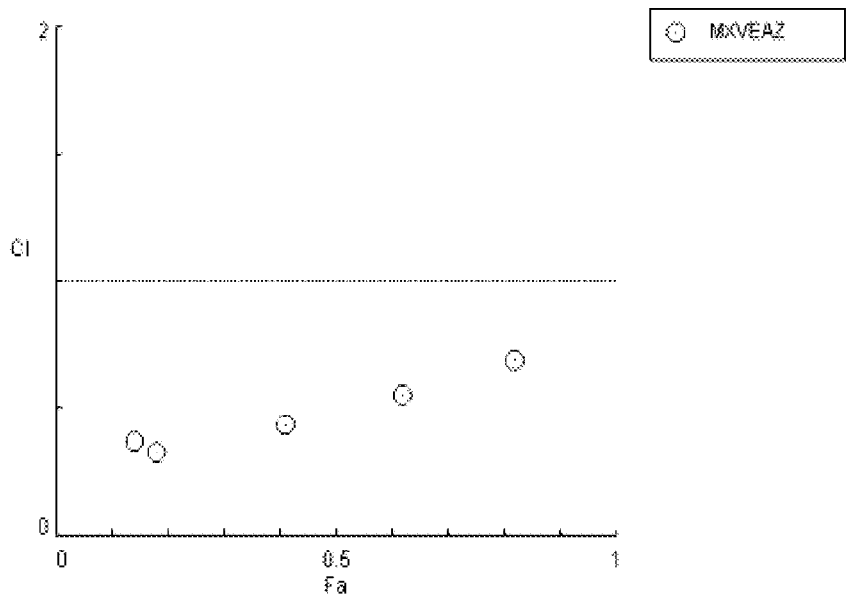
Figure 8D:
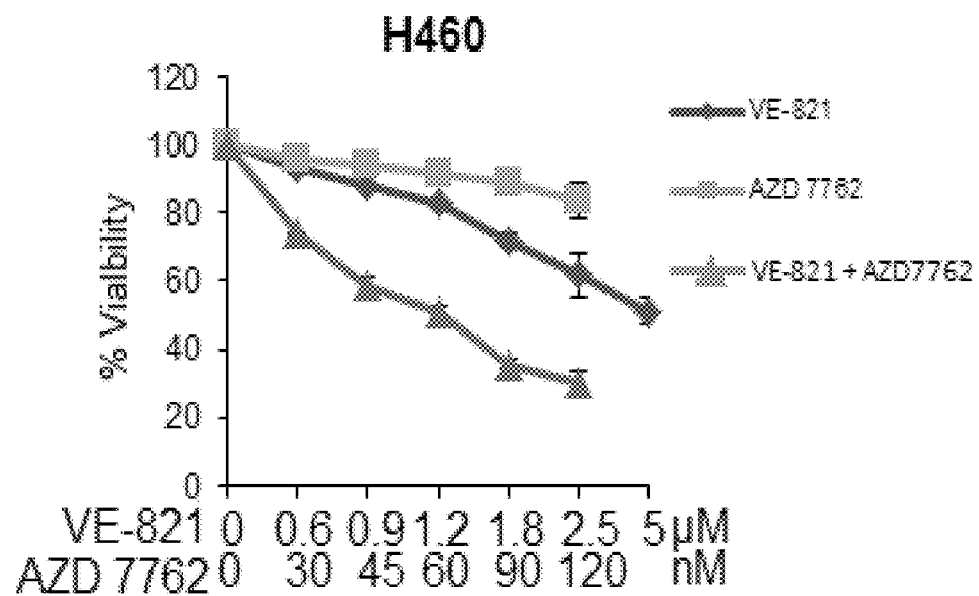
FIG. 8D: graph showing cell viability of MX-1 cancer cells following combination treatment with a Chk1 inhibitor and ATR inhibitor.
Figure 8D:
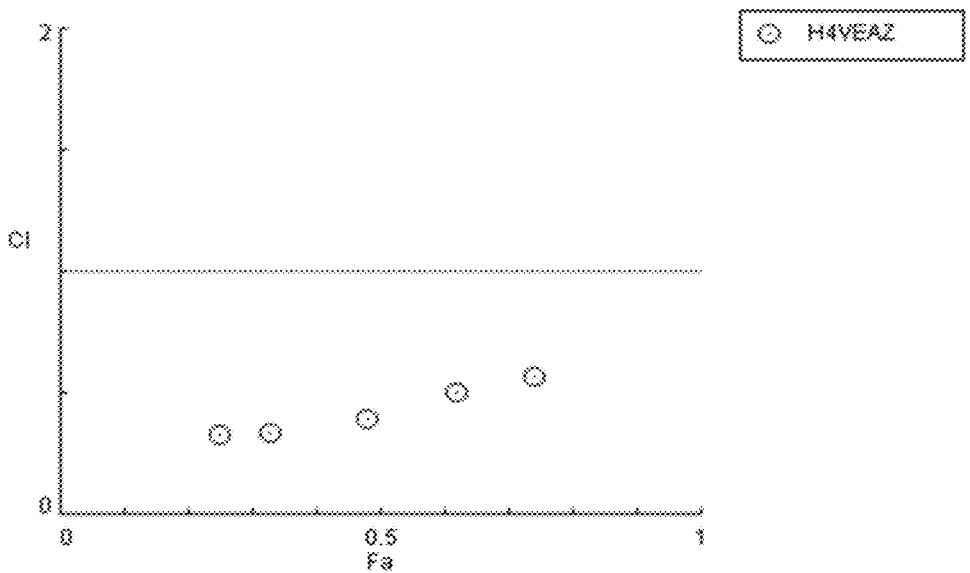
Figure 8E:
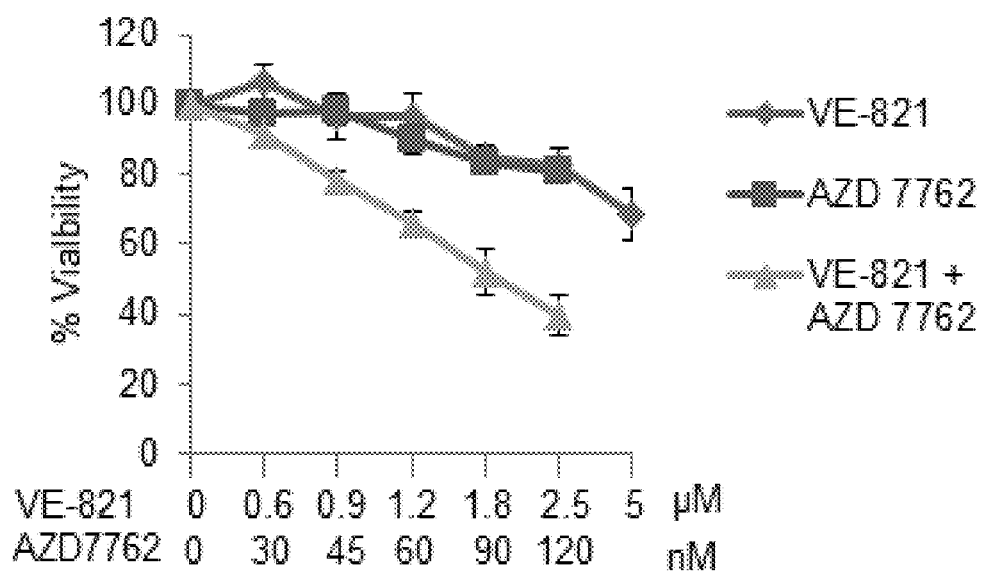
FIG. 8E: graph showing cell viability of HCT-116 cancer cells following combination treatment with a Chk1 inhibitor and ATR inhibitor.
Figure 8E:
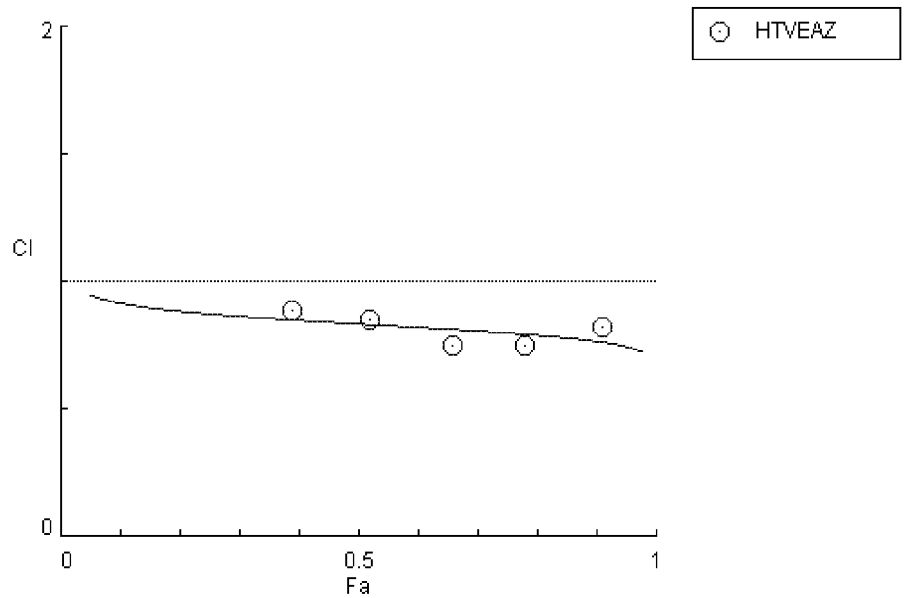
Figure 8F:
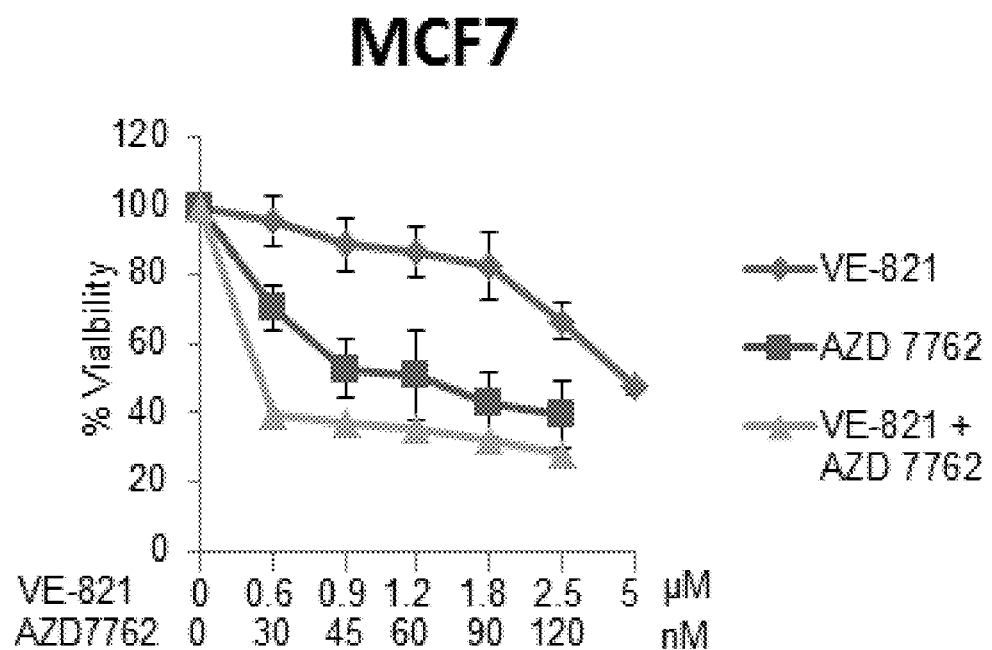
FIG. 8F: graph showing cell viability of MCF7 cancer cells following combination treatment with a Chk1 inhibitor and ATR inhibitor.
Figure 8F:
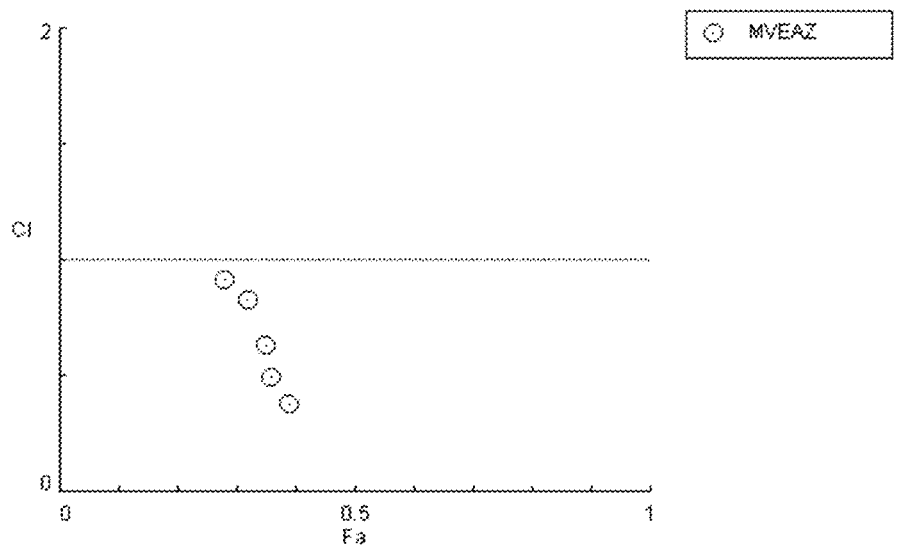
Figure 8G:
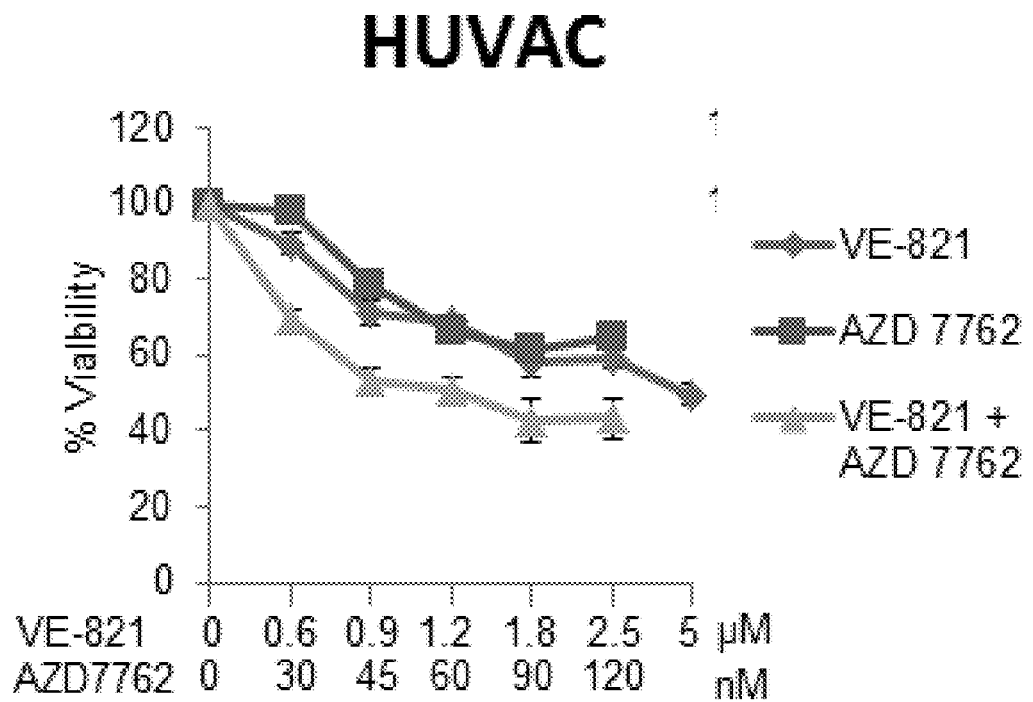
FIG. 8G: graph showing cell viability of HUVAC normal endothelial cells following combination treatment with a Chk1 inhibitor and ATR inhibitor.
Figure 8G:
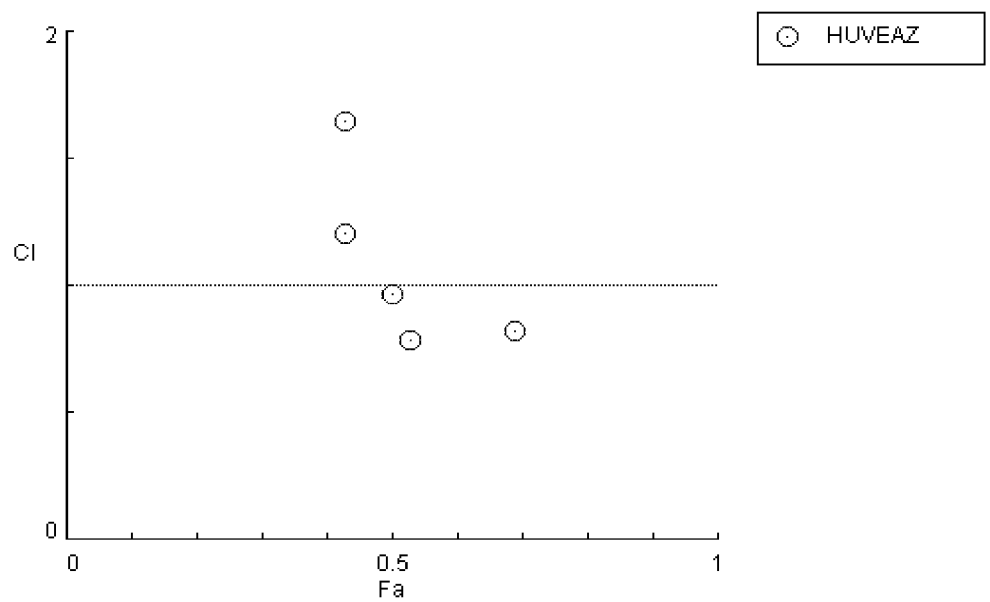
Figure 8H:
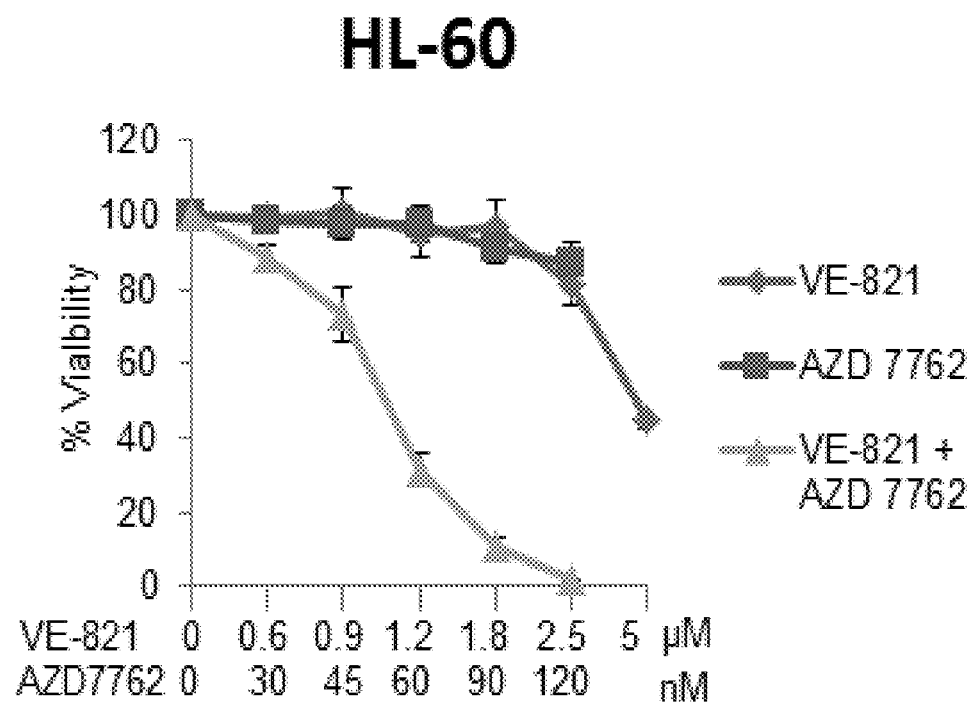
FIG. 8H: graph showing cell viability of HL60 cancer cells following combination treatment with a Chk1 inhibitor and ATR inhibitor.
Figure 8H:
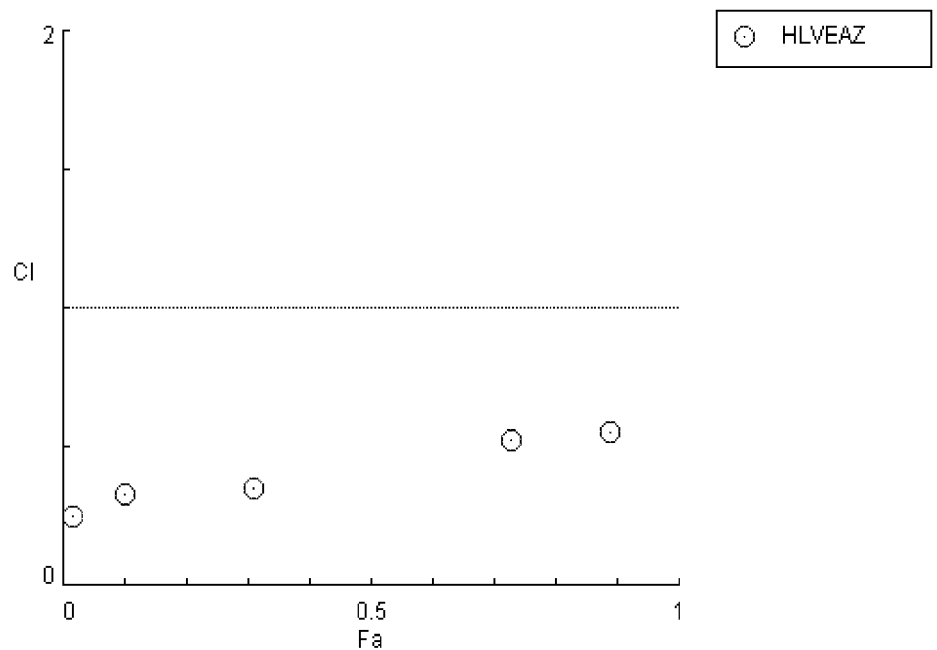

Combination of an ATR Inhibitor and a Chk-1 Inhibitor Induces Single Strand DNA Formation Referring to FIG. 7A and FIG. 7B, U2OS cancer cells and VH-10 normal fibroblast cells were treated for 24 h with doses shown in the figures. Post treatment the cells were pre-extracted to wash off non-chromatin bound RPA fraction and fixed in 4% PFA. Cells were stained with anti RPA 32 antibody; images were taken using confocal microscope and were analysed using Image J software. Mean Intensity ≥70 AU per cell was consider as positive cell. Quantitative data of U2OS and VH-10 respectively, n=3, mean±S.E.M. This shows inhibition of Chk1 leads to elevated ssDNA (a marker of replication stress), which is enhanced by inhibition of ATR, in cancer but not non-cancer cells.

Example 7

Combination of an ATR Inhibitor and a Chk1 Inhibitor Synergistically Kills Cancer Cells, but not Normal Cells As shown in FIGS. 8A-8G, multiple cancer cell lines (U2OS (A), H460 (C), MX-1 (D), HCT-116 (E), MCF7 (F), and HL60 (H) cancer cells), as well as normal fibroblast and endothelial cells (VH-10 (B) and HUVAC (G)), were seeded in 96 well plates and treated for 72 h with the doses indicated in the figures. Resazurin based assay was used to measure viability of cells after introduction of VE-821 and AZD7762 either alone or in combination. Drug interaction was analyzed by using Compusyn software. CI index below 1 to be consider as Synergistic interaction. Quantitative data n=3, mean±S.E.M. The figures show the viability of particular cell lines against the inhibitors alone or in combination. Referring again to FIGS. 8A-8G, the accompanying drug interaction plot is also provided for each cell line after administering both VE-821 and AZD7762. As shown in both the cell viability and the drug interaction plots, the combination of ATR and Chk1 inhibitors has synergistic cytotoxicity in all cancer cell lines tested but not non-cancer cells. This suggests that the combination of ATR and Chk1 inhibitors could be used to kill tumor cells while sparing normal tissue.

Example 8

Figure 9:
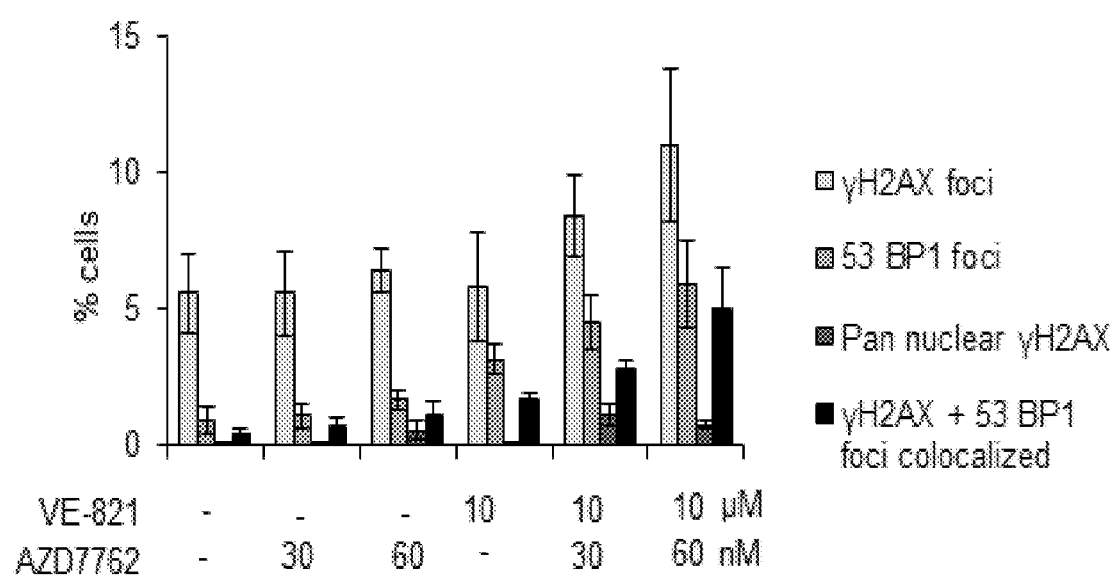
FIG. 9: graph showing the impact of Chk1 inhibition and ATR inhibition on DNA damage levels in VH-10 normal fibroblast cells by measuring the accumulation of pan-nuclear γH2AX and by measuring the accumulation of discrete foci of γH2AX and 53BP1.
Figure 10A:
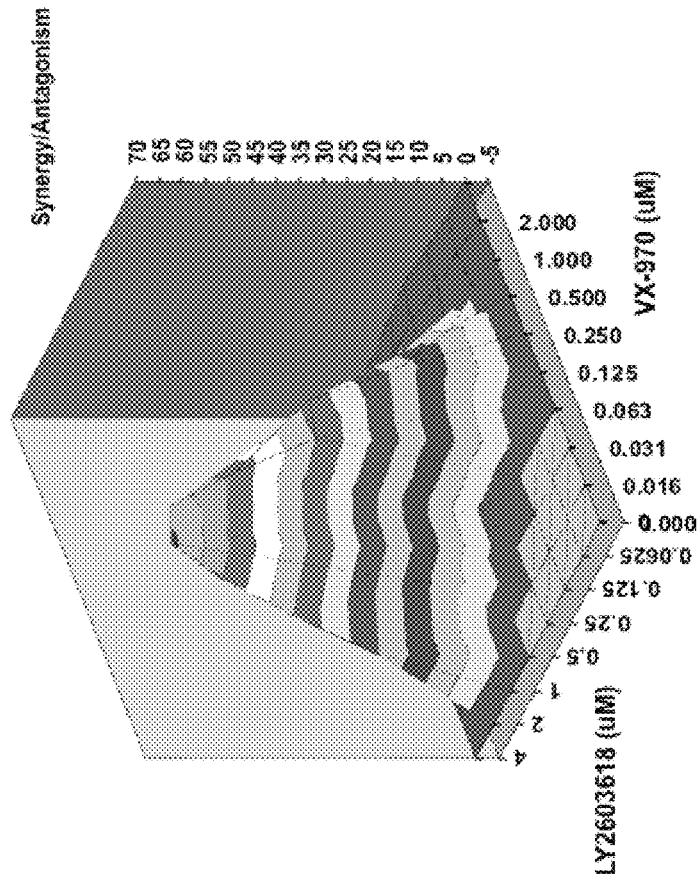
FIG. 10A: graph showing cell viability of HT-29 cancer cells after combination treatment with ATR inhibitor VE-822 and Chk1 inhibitor AZD-7762.
Figure 10B:
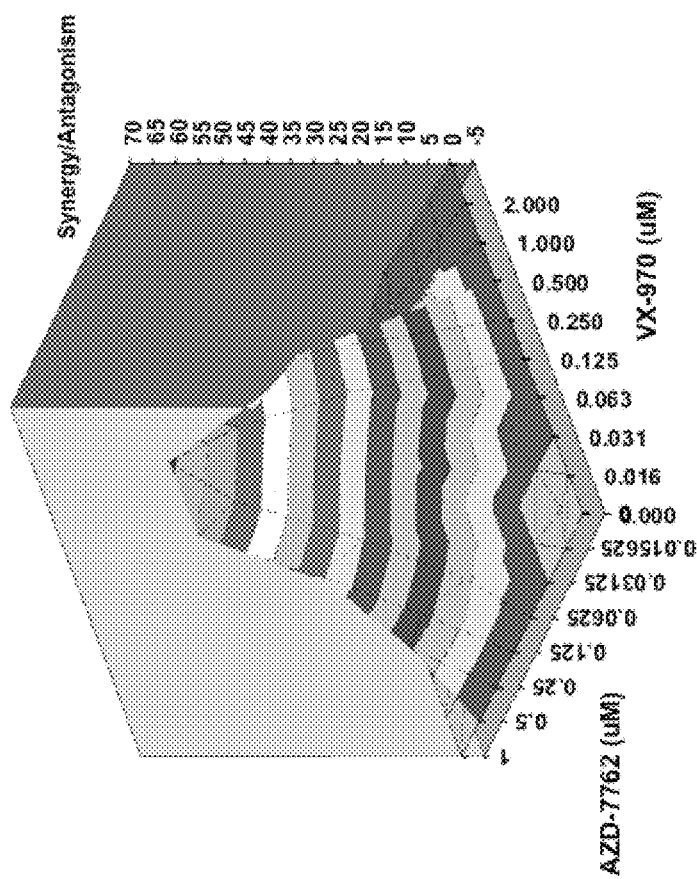
FIG. 10B: graph showing cell viability of HT-29 cancer cells after combination treatment with ATR inhibitor VE-822 and Chk1 inhibitor LY-2603618.
Figure 10D:
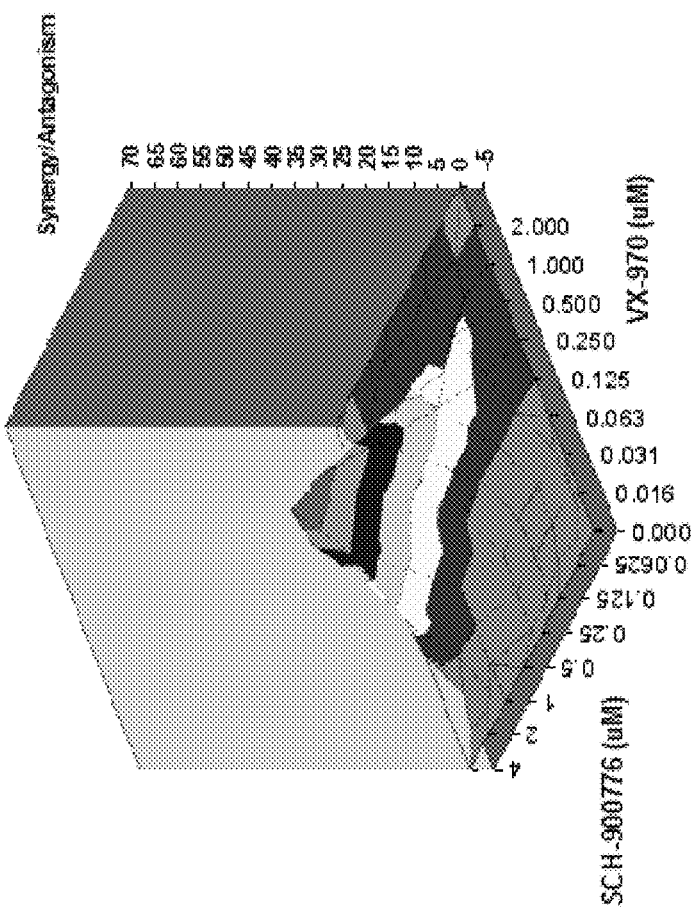
FIG. 10D: graph showing cell viability of HT-29 cancer cells after combination treatment with ATR inhibitor VE-822 and Chk1 inhibitor SCH-900776.
Figure 10C:
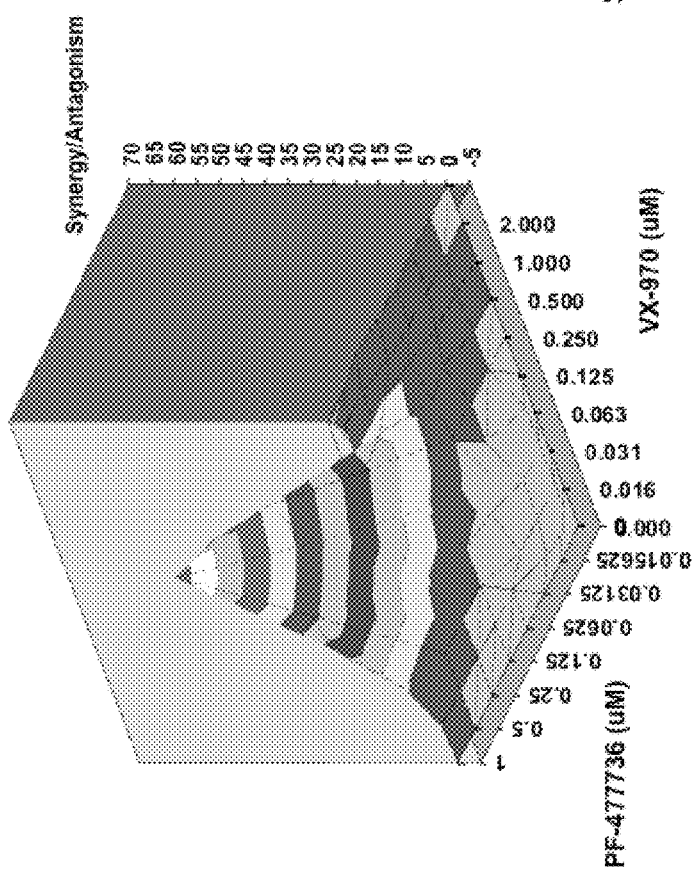
FIG. 10C: graph showing cell viability of HT-29 cancer cells after combination treatment with ATR inhibitor VE-822 and Chk1 inhibitor PF-477736.

Inhibition of Chk1 and ATR does not Lead to High Levels of DNA Damage in Normal Cells As shown in FIG. 9, the impact of Chk1 inhibition by AZD-7762 and ATR inhibition by VE-821 on DNA damage levels in normal cells was assessed by measuring the accumulation of pan-nuclear γH2AX, a widely used indicator of high levels of DNA damage, and by measuring the accumulation of discrete foci of γH2AX and 53BP1, which are markers of lower levels of DNA damage. VH-10 normal fibroblasts were treated for 24 hr with DMSO, AZD-7762 (30 nM or 60 nM) and/or VE-821 (10 uM). Cells were then stained with anti-phospho (serine 139) histone H2AX and anti-53BP1 antibody as primary antibodies, and fluorescent secondary antibodies, and the Operetta fluorescence microscope was used to take images which were analyzed using Columbus software. Cells with nine or more γH2AX or 53BP1 foci were considered γH2AX or 53BP1 foci positive. Cells with smeared γH2AX and no distinguishable foci were considered pan-nuclear γH2AX cell positive. Data are presented as mean±S.E.M.

Treatment of VH10 normal cells with either the ATR inhibitor VE-821 or the Chk1 inhibitor AZD-7762 alone, or treatment with both agents, had minimal impact on the percentage of cells staining γH2AX focus positive, 53BP1 focus positive or pan-nuclear γH2AX positive. Specifically, treatment with both agents led to <2% cells staining positive for pan-nuclear γH2AX (FIG. 5B). These results suggest that the combination of Chk1 inhibitors and ATR inhibitors does not lead to increased DNA damage in normal cells.

Example 9

ATR Inhibitor VE-822 Synergizes with Various Chk Inhibitors

As shown in FIGS. 10 A-D, HT29 cancer cells were treated in triplicate with VX-970 and the indicated Chk inhibitors for 96 h, when cell viability was measured by MTS assay. Synergy was analyzed at the 95% interval using MacSynergy II software.

All tested Chk inhibitors displayed synergistic cytotoxicity in combination with the ATR inhibitor VE-822, including the dual Chk1 and Chk2 inhibitor AZD-7762 (A) and the Chk1 selective inhibitor SCH-900776 (D). These results suggest that an ATR inhibitor can effectively synergize with different clinical Chk1 inhibitors on cancer cells.

Assays

Example 10

Cellular ATR Inhibition Assay

Compounds can be screened for their ability to inhibit intracellular ATR using an immunofluorescence microscopy assay to detect phosphorylation of the ATR substrate histone H2AX in hydroxyurea treated cells. HT29 cells are plated at 14,000 cells per well in 96-well black imaging plates (BD 353219) in McCoy's 5A media (Sigma M8403) supplemented with 10% foetal bovine serum (JRH Biosciences 12003), Penicillin/Streptomycin solution diluted 1:100 (Sigma P7539), and 2 mM L-glumtamine (Sigma G7513), and allowed to adhere overnight at 37° C. in 5% $CO_2$. Compounds are then added to the cell media from a final concentration of 25 µM in 3-fold serial dilutions and the cells are incubated at 37° C. in 5% $CO_2$. After 15 min, hydroxyurea (Sigma H8627) is added to a final concentration of 2 mM.

After 45 min of treatment with hydroxyurea, the cells are washed in PBS, fixed for 10 min in 4% formaldehyde diluted in PBS (Polysciences Inc 18814), washed in 0.2% Tween-20 in PBS (wash buffer), and permeabilised for 10 min in 0.5% Triton X-100 in PBS, all at room temperature. The cells are then washed once in wash buffer and blocked for 30 min at room temperature in 10% goat serum (Sigma G9023) diluted in wash buffer (block buffer). To detect H2AX phosphorylation levels, the cells are then incubated for 1 h at room temperature in primary antibody (mouse monoclonal anti-phosphorylated histone H2AX Ser139 antibody; Upstate 05-636) diluted 1:250 in block buffer. The cells are then washed five times in wash buffer before incubation for 1 h at room temperature in the dark in a mixture of secondary antibody (goat anti-mouse Alexa Fluor 488 conjugated antibody; Invitrogen A11029) and Hoechst stain (Invitrogen H3570); diluted 1:500 and 1:5000, respectively, in wash buffer. The cells are then washed five times in wash buffer and finally 100 ul PBS is added to each well before imaging.

Cells are imaged for Alexa Fluor 488 and Hoechst intensity using the BD Pathway 855 Bioimager and Attovision software (BD Biosciences, Version 1.6/855) to quantify phosphorylated H2AX Ser139 and DNA staining, respectively. The percentage of phosphorylated H2AX-positive nuclei in a montage of 9 images at 20× magnification is then calculated for each well using BD Image Data Explorer software (BD Biosciences Version 2.2.15). Phosphorylated H2AX-positive nuclei are defined as Hoechst-positive regions of interest containing Alexa Fluor 488 intensity at 1.75-fold the average Alexa Fluor 488 intensity in cells not treated with hydroxyurea. The percentage of H2AX positive nuclei is finally plotted against concentration for each compound and IC50s for intracellular ATR inhibition are determined using Prism software (GraphPad Prism version 3.0cx for Macintosh, GraphPad Software, San Diego Calif., USA).

The compounds described herein can also be tested according to other methods known in the art (see Sarkaria et al, "Inhibition of ATM and ATR Kinase Activities by the Radiosensitizing Agent, Caffeine: *Cancer Research* 59: 4375-5382 (1999); Hickson et al, "Identification and Characterization of a Novel and Specific Inhibitor of the Ataxia-Telangiectasia Mutated Kinase ATM" *Cancer Research* 64: 9152-9159 (2004); Kim et al, "Substrate Specificities and Identification of Putative Substrates of ATM Kinase Family Members" *The Journal of Biological Chemistry*, 274(53): 37538-37543 (1999); and Chiang et al, "Determination of the catalytic activities of mTOR and other members of the phosphoinositide-3-kinase-related kinase family" *Methods Mol. Biol.* 281:125-41 (2004)).

Example 11

ATR Inhibition Assay

Compounds can be screened for their ability to inhibit ATR kinase using a radioactive-phosphate incorporation assay. Assays are carried out in a mixture of 50 mM Tris/HCl (pH 7.5), 10 mM $MgCl_2$ and 1 mM DTT. Final substrate concentrations are 10 µM [γ-33P]ATP (3mCi 33P ATP/mmol ATP, Perkin Elmer) and 800 µM target peptide (ASEL-PASQPQPFSAKKK).

Assays are carried out at 25° C. in the presence of 5 nM full-length ATR. An assay stock buffer solution is prepared containing all of the reagents listed above, with the exception of ATP and the test compound of interest. 13.5 µL of the stock solution is placed in a 96 well plate followed by addition of 2 µL of DMSO stock containing serial dilutions of the test compound (typically starting from a final concentration of 15 µM with 3-fold serial dilutions) in duplicate (final DMSO concentration 7%). The plate is pre-incubated for 10 minutes at 25° C. and the reaction initiated by addition of 15 µL [γ-33P]ATP (final concentration 10 µM).

The reaction is stopped after 24 hours by the addition of 30 µL 0.1M phosphoric acid containing 2 mM ATP. A multiscreen phosphocellulose filter 96-well plate (Millipore, Cat no. MAPHN0B50) is pretreated with 100 µL 0.2M phosphoric acid prior to the addition of 45 µL of the stopped assay mixture. The plate is washed with 5×200 µL 0.2M phosphoric acid. After drying, 100 µL Optiphase 'SuperMix' liquid scintillation cocktail (Perkin Elmer) is added to the well prior to scintillation counting (1450 Microbeta Liquid Scintillation Counter, Wallac).

After removing mean background values for all of the data points, Ki(app) data are calculated from non-linear regression analysis of the initial rate data using the Prism software package (GraphPad Prism version 3.0cx for Macintosh, GraphPad Software, San Diego Calif., USA).

Example 12

Cisplatin Sensitization Assay

Compounds can be screened for their ability to sensitize HCT116 colorectal cancer cells to Cisplatin using a 96 h cell viability (MTS) assay. HCT116 cells, which possess a defect in ATM signaling to Cisplatin (see, Kim et al.; *Oncogene* 21:3864 (2002); see also, Takemura et al.; *JBC* 281:30814 (2006)) are plated at 470 cells per well in 96-well polystyrene plates (Costar 3596) in 150 µl of McCoy's 5A media (Sigma M8403) supplemented with 10% foetal bovine serum (JRH Biosciences 12003), Penicillin/Streptomycin solution diluted 1:100 (Sigma P7539), and 2 mM L-glumtamine (Sigma G7513), and allowed to adhere overnight at 37° C. in 5% $CO_2$. Compounds and Cisplatin are then both added simultaneously to the cell media in 2-fold serial dilutions from a top final concentration of 10 µM as a full matrix of concentrations in a final cell volume of 200 µl, and the cells are then incubated at 37° C. in 5% $CO_2$. After 96 h, 40 µl of MTS reagent (Promega G358a) is added to each well and the cells are incubated for 1 h at 37° C. in 5% $CO_2$. Finally, absorbance is measured at 490 nm using a SpectraMax Plus 384 reader (Molecular Devices) and the concentration of compound required to reduce the IC50 of Cisplatin alone by at least 3-fold (to 1 decimal place) can be reported.

Example 13

Single Agent HCT116 Activity

Compounds can be screened for single agent activity against HCT116 colorectal cancer cells using a 96 h cell viability (MTS) assay. HCT116 are plated at 470 cells per well in 96-well polystyrene plates (Costar 3596) in 150 µl of McCoy's 5A media (Sigma M8403) supplemented with 10% foetal bovine serum (JRH Biosciences 12003), Penicillin/Streptomycin solution diluted 1:100 (Sigma P7539), and 2 mM L-glumtamine (Sigma G7513), and allowed to adhere overnight at 37° C. in 5% $CO_2$. Compounds are then added to the cell media in 2-fold serial dilutions from a top final concentration of 10 µM as a full matrix of concentrations in a final cell volume of 200 µl, and the cells are then incubated at 37° C. in 5% $CO_2$. After 96 h, 40 µl of MTS reagent (Promega G358a) is added to each well and the cells are incubated for 1 h at 37° C. in 5% $CO_2$. Finally, absorbance is measured at 490 nm using a SpectraMax Plus 384 reader (Molecular Devices) and IC50 values can be calculated.

Example 14

ATR-Complex Inhibition Assay

Compounds were screened for their ability to inhibit ATR kinase, in the presence of partner proteins ATRIP, CLK2 and TopBP1, using a radioactive-phosphate incorporation assay. Assays were carried out in a mixture of 50 mM Tris/HCl (pH 7.5), 10 mM $MgCl_2$ and 1 mM DTT. Final substrate concentrations were 10 µM [g-33P]ATP (3.5 µCi 33P ATP/nmol ATP, Perkin Elmer, Massachusetts, USA) and 800 µM target peptide (ASELPASQPQPFSAKKK, Isca Biochemicals, Cambridgeshire, UK).

Assays were carried out at 25° C. in the presence of 4 nM full-length ATR, 40 nM full-length ATRIP, 40 nM full-length CLK2 and 600 nM TopBP1(A891-S1105). An enzyme stock buffer solution was prepared containing all of the reagents listed above, with the exception of target peptide, ATP and the test compound of interest. This enzyme stock was pre-incubated for 30 minutes at 25° C. 8.5 µL of the enzyme stock solution was placed in a 96-well plate followed by addition of 5 µl of target peptide and 2 µL of DMSO stock containing serial dilutions of the test compound (typically starting from a final concentration of 1.5 µM with 2.5-fold serial dilutions) in duplicate (final DMSO concentration 7%). The plate was pre-incubated for 10 minutes at 25° C. and the reaction initiated by addition of 15 µL [g-33P]ATP (final concentration 10 µM).

The reaction was stopped after 20 hours by the addition of 30 µL 0.3 M phosphoric acid containing 2 mM ATP. A phosphocellulose filter 96-well plate (Multiscreen HTS MAPHNOB50, Merck-Millipore, Massachusetts, USA) was pretreated with 100 µL 0.1 M phosphoric acid prior to the addition of 45 µL of the stopped assay mixture. The plate was washed with 5×200 µL 0.1 M phosphoric acid. After drying, 50 µL Optiphase 'SuperMix' liquid scintillation cocktail (Perkin Elmer, Massachusetts, USA) was added to the well prior to scintillation counting (Wallac 1450 Microbeta Liquid Scintillation Counter, Perkin Elmer, Massachusetts, USA).

After removing mean background values for all of the data points, Ki(app) data were calculated from non-linear regression analysis of the initial rate data using the Prism software package (GraphPad Prism version 6.0c for Macintosh, GraphPad Software Inc., San Diego, USA).

While we have described a number of embodiments of this invention, it is apparent that our basic examples may be altered to provide other embodiments that utilize the compounds, methods, and processes of this invention. Therefore, it will be appreciated that the scope of this invention is to be defined by the appended claims rather than by the specific embodiments that have been represented by way of example herein.

The invention claimed is:

1. A method of treating a cancer in a patient in need thereof comprising administering to the patient:
an effective amount of a compound which inhibits ATR protein kinase, wherein the compound which inhibits ATR protein kinase is:

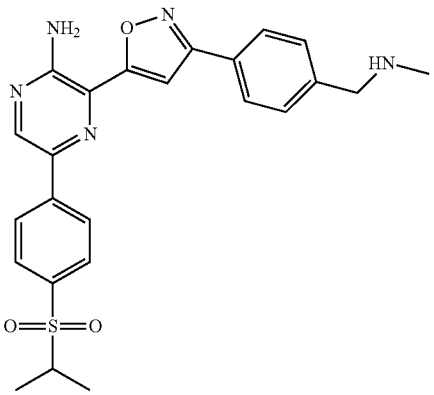

VE-822 or a pharmaceutically acceptable salt thereof; and
an effective amount of a compound which inhibits Chk1 protein kinase, wherein the compound which inhibits Chk1 protein kinase is AZD7762;
wherein the cancer is selected from the group consisting of breast cancer and lung cancer.

2. The method of claim 1, further comprising administering to said patient an effective amount of a DNA-damaging agent.

3. The method of claim 2, wherein the DNA-damaging agent is administered together with the compound which inhibits ATR protein kinase as a single dosage form or separately from the compound which inhibits ATR protein kinase as part of a multiple dosage form.

4. The method of claim 2, wherein said DNA-damaging agent is a chemotherapeutic agent or ionizing radiation.

5. The method of claim 4, wherein said DNA-damaging agent comprises ionizing radiation, radiomimetic neocarzinostatin, a platinating agent, a Topo I inhibitor, a Topo II inhibitor, an antimetabolite, an alkylating agent, an alkyl sulphonate, or an antibiotic.

6. The method of claim 1, further comprising administering to said patient an effective amount of an inhibitor of PARP1 or PARP2.

7. The method of claim 6, further comprising administering to said patient an effective amount of a DNA-damaging agent.

8. The method of claim 7, wherein said DNA-damaging agent is a chemotherapeutic agent or ionizing radiation.

9. The method of claim 8, wherein said DNA-damaging agent comprises ionizing radiation, radiomimetic neocarzinostatin, a platinating agent, a Topo I inhibitor, a Topo II inhibitor, an antimetabolite, an alkylating agent, an alkyl sulphonate, or an antibiotic.

10. The method of claim 1, wherein said cancer is non-small cell lung cancer, small cell lung cancer, or triple negative breast cancer.

11. The method of claim 2, wherein the DNA damaging agent is gemcitabine or cisplatin and the cancer is squamous subtype of non-small cell lung cancer.

12. The method of claim 6, wherein the cancer has a determined defect in a base excision repair protein.

13. The method of claim 12, wherein the base excision repair protein is UNG, SMUG1, MBD4, TDG, OGG1, MYH, NTH1, MPG, NEIL1, NEIL2, NEIL3, APE1, APEX2, LIG1, LIG3, XRCC1, PNK, PNKP, PARP1, PARP2, PolB, PolG, FEN1, or Aprataxin.

14. The method of claim 1, wherein the cancer has a determined defect in ATM signaling cascade.

15. The method of claim 14, wherein the defect in ATM signaling cascade is altered expression or activity of one or more of the following: ATM, p53, CHK2, MRE11, RAD50, NBS1, 53BP1, MDC1, H2AX, MCPH1/BRIT1, CTIP, and SMC1.

16. The method of claim 1, wherein the cancer is determined to express a DNA damaging oncogene.

17. The method of claim 16, wherein said cancer has altered expression or activity of one or more of the following: K-Ras, N-Ras, H-Ras, Raf, Myc, Mos, E2F, Cdc25A, CDC4, CDK2, Cyclin E, Cyclin A and Rb.

* * * * *